US009913890B2

(12) United States Patent
Andrianov et al.

(10) Patent No.: US 9,913,890 B2
(45) Date of Patent: Mar. 13, 2018

(54) METHODS AND COMPOSITIONS FOR EMERGENCY POST-INFECTION TREATMENT OF ANTHRAX

(71) Applicant: Pharma Green LLC, Feasterville-Trevose, PA (US)

(72) Inventors: Vyacheslav Andrianov, Warrington, PA (US); Maxim Golovkin, Huntingdon Valley, PA (US)

(73) Assignee: PHARMA GREEN LLC, Feasterville-Trevose, PA (US)

( * ) Notice: Subject to any disclaimer, the term of this patent is extended or adjusted under 35 U.S.C. 154(b) by 858 days.

(21) Appl. No.: 13/922,719

(22) Filed: Jun. 20, 2013

(65) Prior Publication Data
US 2015/0033410 A1 Jan. 29, 2015

Related U.S. Application Data

(60) Provisional application No. 61/663,271, filed on Jun. 22, 2012.

(51) Int. Cl.
*A61K 39/07* (2006.01)
*C07K 14/32* (2006.01)
*C12N 15/32* (2006.01)
*C12N 15/82* (2006.01)
*A61K 39/40* (2006.01)

(52) U.S. Cl.
CPC .............. *A61K 39/07* (2013.01); *A61K 39/40* (2013.01); *C07K 14/32* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,316,931 A | 5/1994 | Donson et al. | |
| 5,589,367 A | 12/1996 | Donson et al. | |
| 5,889,190 A | 3/1999 | Donson et al. | |
| 5,889,191 A | 3/1999 | Turpen | |
| 6,010,883 A * | 1/2000 | Nagai .................. | C07K 14/4716 435/252.3 |
| 7,667,092 B2 | 2/2010 | Klimyuk et al. | |
| 7,670,801 B2 | 3/2010 | Gleba et al. | |
| 7,763,458 B2 | 7/2010 | Gleba et al. | |
| 8,003,381 B2 | 8/2011 | Klimyuk et al. | |
| 8,093,458 B2 | 1/2012 | Marillonnet et al. | |
| 8,173,408 B2 | 5/2012 | Yusibov et al. | |
| 2003/0228612 A1* | 12/2003 | Kenward ........... | C12N 15/8257 435/6.13 |
| 2007/0118934 A1* | 5/2007 | Yu .................... | C07K 14/705 800/288 |

OTHER PUBLICATIONS

GQ478119 (published 2009; see alignment appended in the Office action).*
GenBank AY233452AAP04016.1 (published 2003; see alignment appended in the Office action).*
GenBank AAG00909.1 (2001, see alignment appended in the Office action).*
GenBank NM_144646 (Mar. 13, 2011; see alignment appended in the Office action).*
Wycoff et al (Antimicrob. Agents. Chemother., Jan. 2011, 55(1):132-139; cited on IDS).*
GenBank AF237583 (2001; see sequence in Office action).*
Christensen et al (The Plant Cell, 2005, 17(10): 2805-2816).*
Ronnmark et al (Journal of Immunological Methods, 2002, 261: 199-211).*
Andrianov et al., "Production of recombinant anthrax toxin receptor (ATR/CMG2) fused with human Fc in planta," Protein Expression and Purification 70:158-162 (2010).
Bennetzen et al. "Codon Selection in Yeast," J Mol Chem 257: 302 (1982).
Bradley et al., "Identification of the cellular receptor for anthrax toxin," Nature 414:225-229 (2001).
Golovkin et al., "Smallpox subunit vaccine produced in planta confers protection in mice," Proc. Natl. Acad. Sci., 104:6864-6869 (2007).
Golovkin Maxim, "Plant-Derived vaccines: Plant biotechnology for production of recombinant pharmaceuticals," Human Vaccines 7(3): 1-2 (2011).
Golovkin Maxim, "Production of recombinant pharmaceuticals using plant biotechnology," In: Bioprocess Science and Technology, Series Biochemistry Research Trends Ed. Min-Tze Liong. Nova Sci. Publ., Inc., USA. (2011).
Hassouneh et al., "Elastin-like Polypeptides as a Purification Tag for Recombinant Proteins," Curr Protocol Protein Sci 6:6:11 (2010).
Itakura et al. "Expression in *Escherichia coli* of a Chemically Synthesized gene for the Hormone Somatostatin," Science 198:1056-1063 (1977).
Lacy et al., "Crystal structure of the von Willebrand factor A domain of human capillary morphogenesis protein 2: an anthrax toxin receptor," Proc Natl Acad Sci USA, 101: 6367-6372 (2004).
Komari et al., "Binary Vectors and Super Binary Vectors," Methods in Mol. Biol. vol. 343, Agrobacterium Protocols, Ed. K.Wang, Humana Press 2006.
Manayani et al., "A viral nanoparticle with dual function as an anthrax antitoxin and vaccine," PLoS Pathog 3:e142 (2007).
McLean et al., "Purification of the therapeutic antibody trastuzumab from genetically modified plants using safflower Protein A-oleosin oilbody technology," Transgenic Res, 21:1291-1301 (2012).
Meyer and Chilcoti, "Purification of Recombinant Proteins by Fusion with with thermally-Responsive Peptides," Nat Rev. Immunol 5:905-916 (1999).

(Continued)

*Primary Examiner* — Stephen Uyeno
(74) *Attorney, Agent, or Firm* — Volpe and Koenig, P.C.

(57) ABSTRACT

Compositions effective for treating or preventing an anthrax infection in a subject in need thereof and recombinant proteins included in the compositions are provided. Methods for producing recombinant proteins in plants are described. Transgenic plants engineered to produce recombinant proteins as well as genetic constructs comprising nucleic acids encoding recombinant proteins thereof are also described. Methods of protecting subjects against anthrax infection with plant-derived compositions are provided.

16 Claims, 17 Drawing Sheets

(56) References Cited

OTHER PUBLICATIONS

Nakamura et al. "Codon Usage Tabulated from International DNA Sequence Databases: Status for the Year 2000," Nucl Acid Res 28: 292 (2000).
Rainey and Young, "Antitoxins: novel strategies to target agents of bioterrorism," Nat. Rev. Microbiol., 2: 721-726 (2004).
Schroder et al., "Nasal and Parenteral Immunizations with Diphtheria Toxoid Using Monoglyceride/Fatty Acid Lipid Suspensions as Adjuvants," 1999 Vaccine 17:2096.
Scobie et al., "A soluble receptor decoy protects rats against anthrax lethal toxin challenge," The Journal of Infectious Diseases, 192: 1047-51 (2005).
Scobie et al.,"Human capillary morphogenesis protein 2 functions as an anthrax toxin receptor," Proc Natl Acad Sci USA, 100: 5170-74 (2003).
Spitsin et al., "Immunological assessment of plant-derived avian flu H5/HA1 variants," Vaccine, 27:1289-1292 (2009).
Thomas et al., "Delayed toxicity associated with soluble anthrax toxin receptor decoy-Ig fusion protein treatment," PLoS ONE, 7:e34611 (2012).
Van Engelen et al., "PBINPLUS; an Improved Plant Transformation Vector Based pn pBIN19," Transgenic Research 4: 288-290 (1995).
Vuyisich et al., "A dual-purpose protein ligand for effective therapy and sensitive diagnosis of anthrax," Protein J 27:292-302 (2008).
Vajdy et al., "Mucosal Adjuvants and delivery Systems for Protein-, DNA- and RNA-based Vaccines," Imm and Cell Biol 82:617 (2004).
Wycoff et al., "Recombinant Anthrax Toxin Receptor-Fc Fusion Proteins Produced in Plants Protect Rabbits against Inhalational Anthrax," Antimicrobial Agents and Chemotherapy 55:132-139 (2011).
Young and Collier, "Anthrax Toxin: Receptor Binding, Internalization, Pore Formation, and Translocation," Annu. Rev. Biochem. 76:243-265 (2007).

* cited by examiner

Post-infection neutralization of anthrax toxin

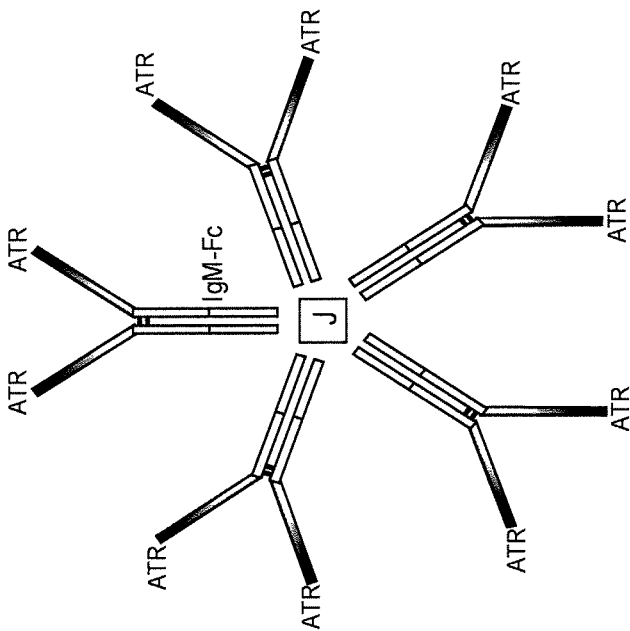
Component A1-B3
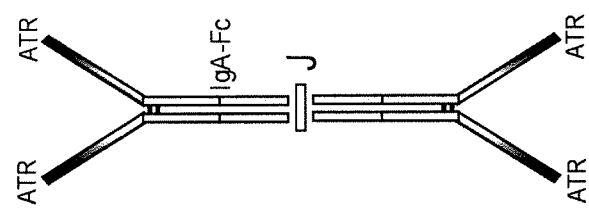
Component A1-B2
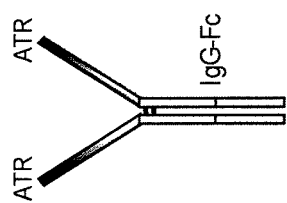
Component A1-B1
FIG. 2B

```
                    ┌─────────────────────────┐
                    │  Introducing a vector into │
                    │         plant            │
                    └─────────────┬───────────┘
                                  │
                    ┌─────────────┴───────────┐
                    │ Generation of a plant poducing │
                    │   recombinant ATR protein │
                    └──────┬───────────┬──────┘
                           │           │
              ┌────────────┘           └────────────┐
              │                                     │
       ┌──────┴──────┐                       ┌──────┴──────┐
       │  Crop plant │                       │ Medicinal plant │
       └──────┬──────┘                       └──────┬──────┘
              │                                     │
       ┌──────┴──────┐                  ┌──────────┴──────────┐
       │  Extraction │                  │ Extract @ direct application │
       └──────┬──────┘                  └──────────┬──────────┘
              │                                     │
┌─────────────┴───────────────┐                    │
│ Purification on a)protein A agarose │            │
│   or with b)His/c-myc tag   │                    │
└─────────────┬───────────────┘                    │
              │                                     │
              └──────────────┬──────────────────────┘
                             │
   ┌──────────────────────┐  │  ┌──────────────────────────┐
   │ Pharmaceutically acceptable │─┤ Plant derived composition with │
   │       carrier        │     │   recombinant ATR protein │
   └──────────────────────┘     └──────────────┬───────────┘
                                               │
   ┌──────────────────────┐                    │
   │ Enchancers and/or adjuvants │─────────────┤
   └──────────────────────┘     ┌──────────────┴───────────┐
                                │  Therapeutic composition │
                                └──────────────┬───────────┘
   ┌──────────────────────┐                    │
   │  Needle-free infusion │                   │
   │  Transdermal patches │    ┌───────────────┴──────────┐
   │  Pulmonary delivery  │────│ Delivery of composition in │
   │  Intranasal spray    │    │    object bloodstream     │
   └──────────────────────┘    └──────────────────────────┘
```

FIG.8

METHODS AND COMPOSITIONS FOR EMERGENCY POST-INFECTION TREATMENT OF ANTHRAX

CROSS REFERENCE TO RELATED APPLICATION

This application claims the benefit of U.S. Provisional Application No. 61/663,271, filed Jun. 22, 2012, which is incorporated by reference as if fully set forth.

The sequence listing electronically filed with this application titled "Sequence Listing," created on Jun. 20, 2013, and having a file size of 92,586 bytes is incorporated herein by reference as if fully set forth. The substitute sequence listing electronically filed Oct. 17, 2014 titled "Substitute Sequence Listing," created on Oct. 17, 2014, and having a file size of 92,931 bytes is incorporated herein by reference as if fully set forth.

FIELD OF INVENTION

The invention relates to methods and compositions to produce recombinant proteins in plants for the post-infection treatment or prophylaxis of the anthrax disease to neutralize the action of the anthrax toxin in the infected subjects. In particular the invention provides recombinant proteins, genetic constructs comprising polynucleotides encoding the proteins thereof, vectors and transgenic plants that include the genetic constructs. Methods for producing recombinant proteins, preparing compositions that include recombinant proteins and methods of protecting subjects by administering the compositions are also provided.

BACKGROUND

Despite the progress in studying mechanisms of anthrax, a zoonotic disease caused by the Gram-positive bacterium *Bacillus anthracia*, a problem remains concerning the prevention and/or post-exposure treatment of the infection, especially with bio-terrorism threats. Although conventional vaccines against anthrax exist, induction and maintenance of adequate protection requires multiple immunizations followed by yearly boosters which frequently cause dangerous side effects (Rainy, Young, 2004). These side effects often inhibit the use of preventive vaccines among the human population.

SUMMARY

An aspect of the invention relates to a recombinant protein. The recombinant protein includes a first protein fused to a second protein. The first protein is a toxin binding ligand. The second protein is a carrier-protein. The carrier-protein is selected from the group consisting of: Fc-IgA, Fc-IgG, Fc-IgM, oleosin, and VP2 coat protein.

An aspect of the invention relates to a genetic construct. The genetic construct includes a first polynucleotide and a second polynucleotide. The first polynucleotide encodes a toxin binding ligand. The second polynucleotide encodes a carrier-protein. The carrier-protein is selected from the group consisting of: Fc-IgA, Fc-IgG, Fc-IgM, oleosin, and VP2 coat protein.

An aspect of the invention relates to a genetic construct. The genetic construct includes a sequence with at least 90% identity to a reference sequence selected from the group consisting of: SEQ ID NO: 16 (PgA1-3:B1-3), SEQ ID NO: 17 (PgA1-4:B1-4), SEQ ID NO: 18 (PgA1-3:B2-4), SEQ ID NO: 19 (PgA1-4:B2-14), SEQ ID NO: 20 (PgA1-3:B3-3), SEQ ID NO:21 (PgA1-4:B3-4), SEQ ID NO: 22 (PgA1-3:B4-2), SEQ ID NO: 23 (PgA1-3:B5-2), SEQ ID NO: 37 (PgA2-4:B1-5), and SEQ ID NO: 38 (PgA1-5:B1-5).

An aspect of the invention relates to a transgenic plant. The transgenic plant comprises a genetic construct. The genetic construct includes a first polynucleotide and a second polynucleotide. The first polynucleotide encodes a toxin binding ligand. The second polynucleotide encodes a carrier-protein. The carrier-protein is selected from the group consisting of: Fc-IgA, Fc-IgG, Fc-IgM, oleosin, and VP2 coat protein.

An aspect of the invention relates to a method for producing a recombinant protein in a plant. The method includes contacting a plant with a genetic construct. The genetic construct includes a nucleic acid encoding the recombinant protein. The recombinant protein includes a toxin binding ligand fused to a carrier-protein. The carrier-protein is selected from the group consisting of: Fc-IgA, Fc-IgG, Fc-IgM, oleosin, and VP2 coat protein. The method also includes obtaining a plant including the genetic construct and expressing the recombinant protein.

An aspect of the invention relates to a method for preparing a composition effective for treating or preventing an anthrax infection in a subject. The method includes providing a recombinant protein produced by any method described herein.

An aspect of the invention relates to a method of protecting a subject against anthrax infection. The method includes providing a composition that includes a recombinant protein. The recombinant protein includes a toxin binding ligand fused to a carrier-protein. The carrier-protein is a protein selected from the group consisting of: Fc-IgA, Fc-IgG, Fc-IgM, oleosin, and VP2 coat protein. The composition is effective in preventing or reducing at least one symptom of an anthrax infection in a subject. The method also includes administering the composition to the subject in need thereof.

BRIEF DESCRIPTION OF THE DRAWINGS

The following detailed description of the preferred embodiments will be better understood when read in conjunction with the appended drawings. For the purpose of illustration, there are shown in the drawings embodiments which are presently preferred. It is understood, however, that the invention is not limited to the precise arrangements and instrumentalities shown. In the drawings:

Figure 1A:
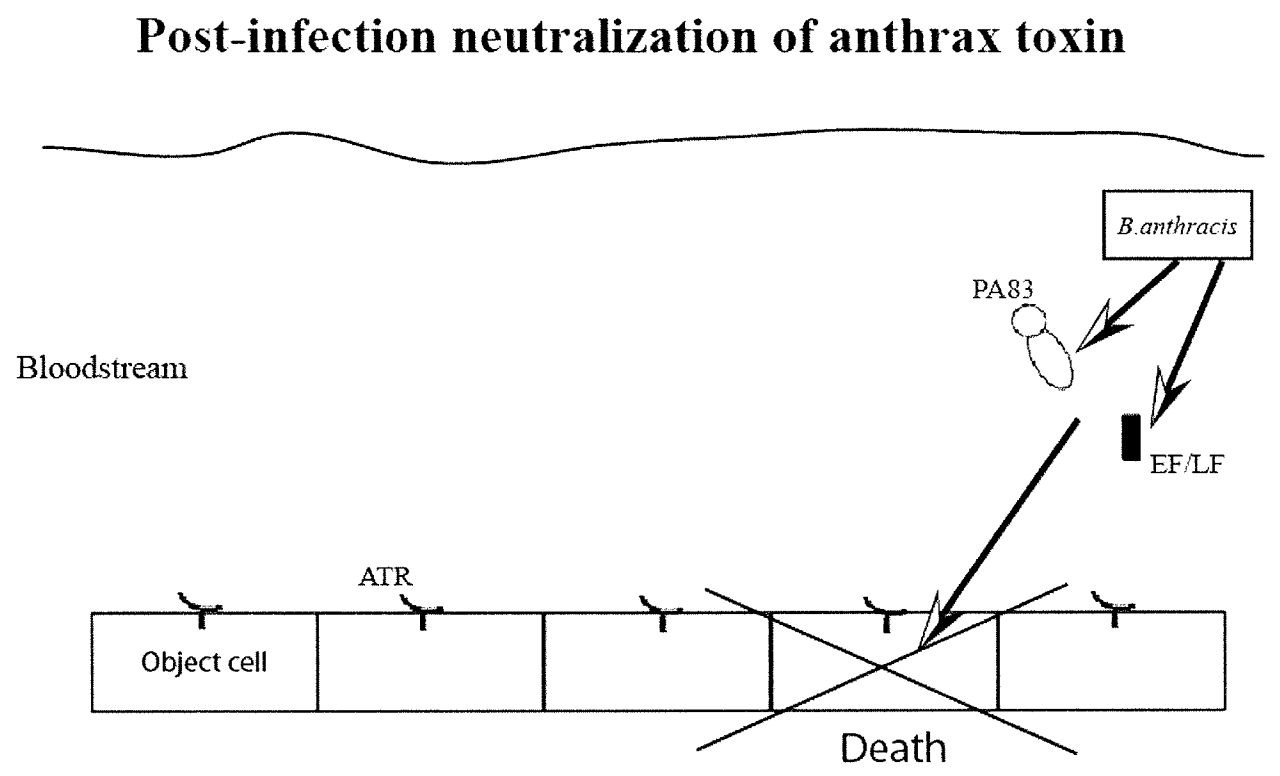

FIG. 1A is a schematic drawing illustrating the formation of anthrax toxin complexes and their entry into cells.

FIG. 2A illustrates a comparison of a native antibody with a recombinant protein that includes an anthrax toxin receptor fused (TBL) to the Fc-region of the immunoglobulin.

FIG. 2B illustrates possible configurations (quaternary structures) of self-assembling A1-B recombinant proteins.

FIG. 5A illustrates formation of transgenic tobacco shoots on the medium supplemented with to 50 mg/L of kanamycin.

FIG. 5B illustrates development of the transgenic tobacco shoots on selection medium.

FIG. 5C illustrates the rooted transgenic tobacco plant grown in a Magenta box.

FIG. 5D illustrates a transgenic tobacco plant grown on in soil.

FIG. 5E illustrates PCR analysis of the transgenic tobacco plants using nptII-specific primers.

FIG. 5F illustrates Western blot analysis of the transgenic tobacco lines using c-myc tag-specific antibodies.

FIG. 6A illustrates formation of the transgenic *Echinaceia angustifolia* shoot on the medium supplemented with to 50 mg/L of kanamycin.

FIG. 6B illustrates mass-propagation of the transgenic *Echinaceia angustifolia* plants.

FIG. 6C illustrates the rooted transgenic *Echinaceia angustifolia* plant grown in a Magenta box.

FIG. 6D illustrates a transgenic *Echinacea angustifolia* plant growing on the selection medium supplemented with kanamycin.

FIG. 6E illustrates Western blot analysis of the transgenic *Echinacea angustifolia* using c-myc tag-specific antibodies.

FIG. 7A illustrates formation of the transgenic *Kalanchoe pinnata* shoot on the medium supplemented with to 50 mg/L of kanamycin.

FIG. 7B illustrates propagation of the transgenic transgenic *Kalanchoe pinnata* shoots on the kanamycin selection medium.

FIG. 7C shows rooting of *Kalanchoe pinnata* shoots on the kanamycin selection medium.

FIG. 8 illustrates steps of the method for producing and administering plant-derived compositions effective to prevent anthrax infection in a subject.

FIG. 9A illustrates Western blot analysis of transgenic plants expressing PgA1-B1 proteins.

FIG. 9B illustrates Western blot analysis of a total and soluble protein extracted from transgenic tobacco plants.

FIG. 9C illustrates extraction and purification of the plant PgA1-B1 recombinant protein from tobacco leaf tissue.

FIG. 10A illustrates an analysis of the PA binding by the recombinant protein PgA1-B1.

FIG. 10B illustrates neutralization of the lethal toxin activity by the recombinant protein PgA1-B1.

DETAILED DESCRIPTION OF THE PREFERRED EMBODIMENTS

Figure 1B:
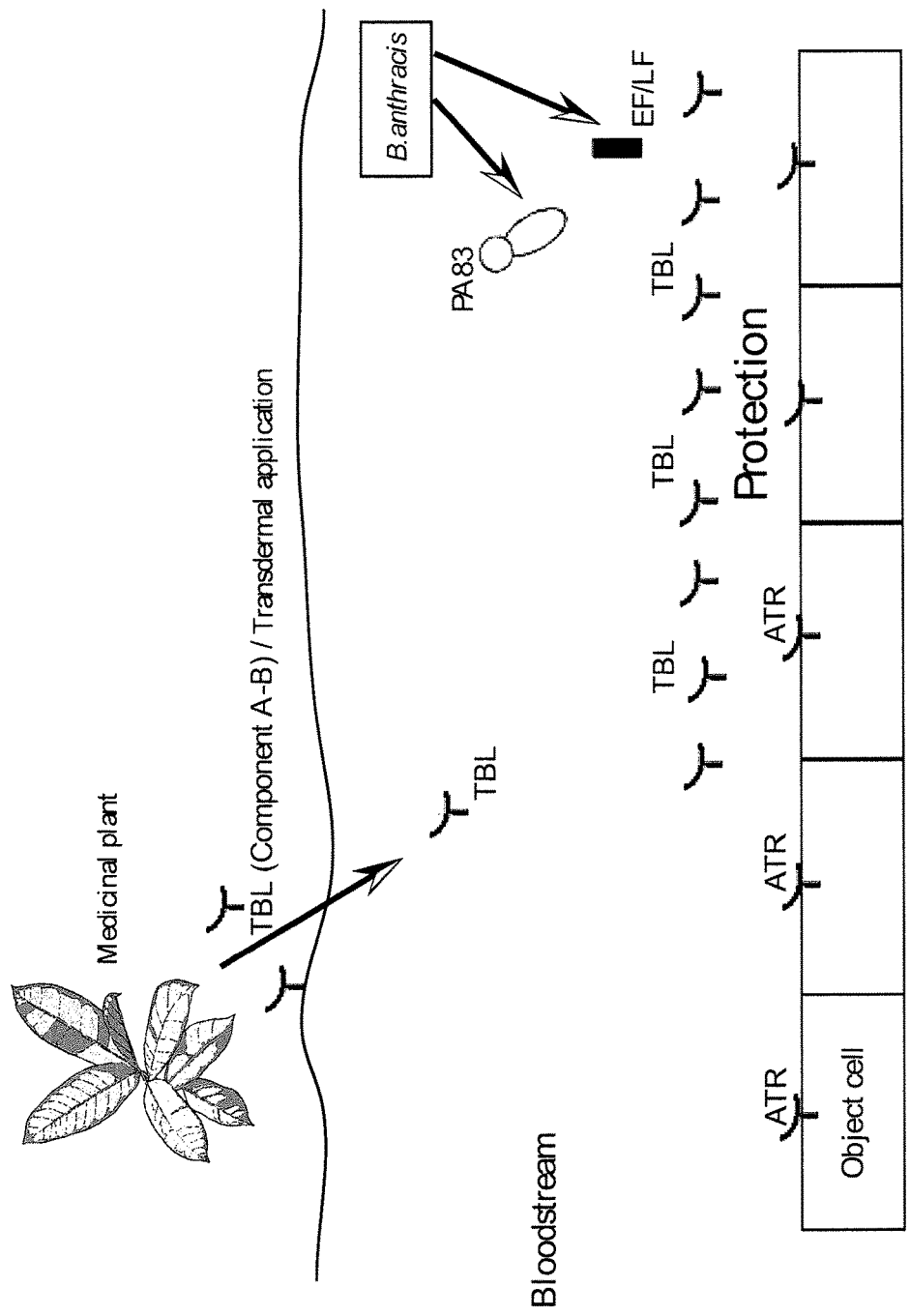
FIG. 1B illustrates an infusion of a recombinant protein that includes an anthrax toxin binding ligand and a carrier protein (component A-B) into the bloodstream of the infected human or animal.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

The onset of acute symptoms of the anthrax disease occurs due to the effects of bacterial toxin consisting of non-lethal components: protective antigen (PA) combined with lethal factor (LF) or edema factor (EF) (FIG. 1A; see Young, Collier, 2007). $PA_{83}$ binds to cellular receptors where it is cleaved by a furin protease to $PA_{63}$, which assembles into a heptameric pore. The pore can binds up to three units of LF, EF or both. Endocytosys of this structure leads to the entry of LF and/or EF into cytosol, where each factor causes its toxic effects. Neutralizing anthrax toxin activity could provide time for antibacterial agents or the immune system to clear up infection. Therefore, early post-infection treatment of anthrax infection with effective anti-toxins that can block the action of toxin in vivo is important (Rainy, Young, 2004).

Embodiments herein provide technologies to express the chemically active recombinant anti-anthrax antitoxin in plants. FIG. 1B illustrates an infusion of recombinant proteins (Component A-B) into the bloodstream of the infected human or animal. Component A-B may be capable of binding $PA_{83}$ protein and preventing it from binding to the anthrax toxin receptor on the cell surface, thus protecting cells from translocation of other toxin component, EF or LF, into the cells. Production of active recombinant antitoxin protein in plants may be easily scaled up. The potential to produce large quantities of antitoxin protein may be useful for preindustrial and industrial scale production, during threats of bioterrorism and continuous outbreaks of anthrax infections. The plant-derived compositions may also be produced at a lower cost compared to traditional antibodies. An advantage of plant-derived antitoxin compositions is that these compositions are free of mammalian pathogens.

In an embodiment, a recombinant protein is provided. The recombinant protein may include a first protein fused to a second protein. The first protein may be a toxin binding ligand (referred to herein as "component A"). The toxin binding ligand may be capable of binding anthrax toxin with high affinity.

The toxin binding ligand may be a human or animal anthrax receptor (ATR) protein. The toxin binding ligand may be a capillary morphogenesis protein 2 (CMG-2; component A1). The toxin binding ligand may be a soluble domain of the CMG-2. The toxin binding ligand may be a soluble domain of another ATR protein. The toxin binding ligand may be a soluble domain of another anthrax toxin-binding polypeptide.

The toxin binding ligand may be a polypeptide capable of high affinity binding to a protective antigen (PA) region necessary for PA interaction with a lethal factor (LF) or an edema factor (EF) components of the anthrax toxin. The toxin binding ligand may be a protective antigen binding domain of a lethal factor (PA-LF; component A2).

In an embodiment, the human capillary morphogenesis protein 2 may include, consist essentially of, or consist of a sequence with at least 70, 72, 75, 80, 85, 90, 91, 92, 93, 94, 95, 96, 97, 98, 99, or 100% identity to a reference sequence of: SEQ ID NO: 24 (A1-CMG2) or SEQ ID NO: 60 (PgA1-5).

In an embodiment, the PA-LFn protein may include, consist essentially of, or consist of a sequence with at least 70, 72, 75, 80, 85, 90, 91, 92, 93, 94, 95, 96, 97, 98, 99, or 100% identity to a reference sequence of: SEQ ID NO: 25 (A2/PA-LF).

In an embodiment, the toxin binding ligand alone may be capable of protecting a subject against anthrax toxin.

The second protein may be a carrier protein (referred to herein as "component B"). The carrier-protein may be capable of improving production, stability, solubility, extraction, secondary structure or other characteristics of the recombinant protein. The carrier-protein may be capable of improving translocation of the recombinant protein through biological membranes and its delivery into the bloodstream of an infected subject. The carrier protein may be capable of simplifying purification of the recombinant protein.

Figure 2A:
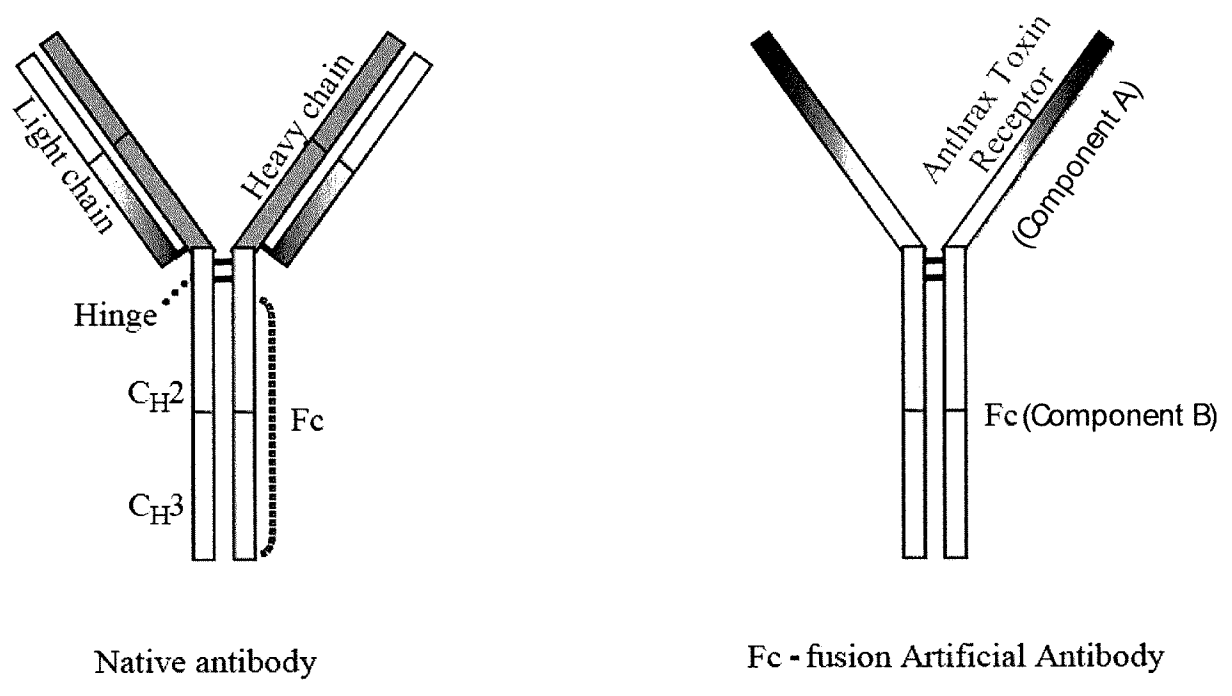

The carrier-protein may be an Fc (fragment crystallizable) region of an antibody capable of interacting with cell surface receptors called Fc receptors. FIG. 2A illustrates a comparison of a native antibody (left) with a recombinant protein that includes the anthrax toxin receptor fused to Fc-region of an immunoglobulin. The Fc-region may be but is not limited to an IgG isotype (component B1), an IgA isotype (component B2), or an IgM isotype (component B3). The Fc region of an antibody may be a single isotype. The Fc region may be a combination of any of IgA, IgG, or IgM isotypes. The Fc-region of an antibody may be combined with elements of several immunoglobulin isotypes that possess properties or have the natural ability of transport across the intestinal epithelium or penetrate higher cell and mucose surfaces. The Fc-regions of recombinant proteins may be capable of assembling into quaternary structures consisting of several similar units. For example, the toxin binding ligand fused to an Fc-region of a human or an animal antibody under native conditions may be capable of forming dimers with another Fc molecule through the formation of disulfide bonds (FIG. 2B). The assembly of the individual Fc-molecules (monomers) into quaternary structures consisting of several similar units (dimers or multimers) may be facilitated by a helper element (referred to herein as "component C"). The helper element may facilitate self-assembly of the Fc-molecules into quaternary structures after bringing them into close proximity with each other, particularly after delivery into a human or a non-human animal organism. The helper element may provide a higher stability in a bloodstream, binding avidity for the anthrax toxin due to its multivalency and ability to induce host immune response to the bound anthrax toxin. The helper element may be an IgJ antibody. The helper element may be a VP1 coat protein of the JC virus. FIG. 2B illustrates possible configurations of self-assembling A1-B recombinant proteins, where the Fc fragment (component B) originates from an antibody (Ab) of different isotypes. FIG. 2B shows that the isotype IgG (B1) may form a bivalent structure (left). The isotype IgA (B2; middle) and the isotype IgM (B3; right) may be capable of binding multiple units together in the presence of "J," a helper element, assisting in self-assembly of separate antibody molecules into dimmer or multimer structures.

The carrier-protein may be of virus origin. The carrier-protein may originate from a polyoma or a papiloma virus proteins capable of self-assembly into quaternary structures resembling virus like particles. The carrier protein may be a virus structural protein. The carrier protein may be a virus coat protein. The carrier protein may be a VP2 coat protein of the JC virus.

The carrier-protein may be capable of targeting itself as well as another covalently fused protein to plant cell oil bodies thus providing accumulation of the target protein in the plant lipid fraction, where it can be easily extracted with cheap available technologies. Particularly, the carrier-protein may be, but is not limited to, a plant oleosin. The oleosin may be capable of targeting the recombinant protein into a lipid fraction of plant cells and accumulating the recombinant protein in an outer surface of plant cell oil bodies, thus providing easy and cheap extraction of the protein from plant biomass. (McLean et al., 2012, *Transgenic Res, March* 2, Epub).

The carrier-protein may be a protein capable of changing solubility under specific temperature condition, thus providing cheap and easy extraction using recently developed technologies available on market. The carrier-protein may be a thermo-stable protein or a thermo-labile protein. The carrier-protein may be a protein from thermophilic bacteria. The carrier-protein from the thermophilic bacteria may be glucuronidase or lichenase B (U.S. Pat. No. 8,173,408, incorporated herein by reference as if fully set forth). The carrier-protein may be an Elastin-Like Polypeptides capable of undergoing a reversible, inverse phase transition and providing technical simplicity, low cost, ease of scale-up of extraction using "inverse transition cycling" technique (Hassouneh et al., 2010, *Curr Protocol Protein Sci* 6:6.11; Meyer, Chilkoti, 1999, *Nat. Rev. Immunol* 5:905-916, all of which are incorporated by reference as if fully set forth).

In an embodiment, the carrier-protein may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 26 (B1), SEQ ID NO: 27 (B2), SEQ ID NO: 28 (B3), SEQ ID NO: 29 (B4) and SEQ ID NO: 30 (B5).

In an embodiment, the helper element may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ NO 35 (C1-protein) and SEQ ID NO: 36 (C-protein).

The first protein or the second protein may be linked to a targeting peptide. The first protein or the second protein may be linked to a peptide tag for detection or purification. The detection or purification tag may be chosen from, but is not limited to, Poly-Arg, Poly-His, FLAG, Strep-tag II, c-myc, S-, HAT-, 3×FLAG, Calmodulin-binding peptide, Cellulose-binding domain, SBP, Chitin-binding domain, Glutation S-transferase, Maltose-binding protein, and Elastin-like peptide.

In an embodiment, the first protein may be fused to the second protein, or the purification tag using a flexible linker. The flexible linker may be a self-cleavable peptide. The flexible linker may be a peptide that is a site for cleaving with a specific protease, available in a composition or naturally present in mammal blood, providing, when necessary, release of the soluble toxin binding ligand from the carrier-protein or the tag during process of extraction or upon delivery of the recombinant protein into a bloodstream of a subject.

In an embodiment, the recombinant protein may include, consist essentially of, or consist of a sequence with at least 70, 72, 75, 80, 85, 90, 91, 92, 93, 94, 95, 96, 97, 98, 99, or 100% identity to a reference sequence of SEQ ID NO: 31 (PgA1-1:B1-1).

In an embodiment, a genetic construct comprising a first polynucleotide and a second polynucleotide is provided. The first polynucleotide may encode a toxin binding ligand. The first polynucleotide may encode a CMG-2 protein. The first polynucleotide may encode a PA-LF protein.

The first polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 1 (PgA1-1), SEQ ID NO: 2 (PgA1-2), SEQ ID NO: 47 (PgA1-3), SEQ ID NO: 49 (PgA1-4) and SEQ ID NO: 58 (PgA1-5). The first polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 3 (PgA2-1), SEQ ID NO: 4 (PgA2-2), SEQ ID NO: 5 (A2-3/PA-LF) and SEQ ID NO: 57 (PgA2-4).

The first polynucleotide may include a sequence capable of hybridizing under conditions of one of low, moderate, or high stringency to a reference sequence selected from the group consisting of: SEQ ID NO: 1 (PgA1-1), SEQ ID NO: 2 (PgA1-2), SEQ ID NO: 47 (PgA1-3), SEQ ID NO: 49 (PgA1-4) and SEQ ID NO: 58 (PgA1-5). The first polynucleotide may include a sequence capable of hybridizing under conditions of one of low, moderate, or high stringency to a reference sequence selected from the group consisting of: SEQ ID NO: 3 (PgA2-1), SEQ ID NO: 4 (PgA2-2), SEQ ID NO: 5 (A2-3/PA-LF) and SEQ ID NO: 57 (PgA2-4).

The second polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO:6 (PgB1-1), SEQ ID NO: 7 (PgB2-1), SEQ ID NO: 8 (PgB3-1), SEQ ID NO: 9 (PgB1-2), SEQ ID NO: 10 (PgB2-2), SEQ ID NO: 11 (PgB3-2), SEQ ID NO: 12 (PgB4-1), SEQ ID NO: 13 (PgB5-1), SEQ ID NO: 48 (PgB1-3), SEQ ID NO: 50 (PgB1-4), SEQ ID NO: 51 (PgB2-3), SEQ ID NO: 52 (PgB2-4), SEQ ID NO: 53 (PgB3-3), SEQ ID NO: 54 (PgB3-4), SEQ ID NO: 55 (PgB4-2), and SEQ ID NO: 56 (PgB5-2).

The second polynucleotide may include a sequence capable of hybridizing under conditions of one of low, moderate, or high stringency to a reference sequence selected from the group consisting of: SEQ ID NO:6 (PgB1-1), SEQ ID NO: 7 (PgB2-1), SEQ ID NO: 8 (PgB3-1), SEQ ID NO: 9 (PgB1-2), SEQ ID NO: 10 (PgB2-2), SEQ ID NO: 11 (PgB3-2), SEQ ID NO: 12 (PgB4-1), SEQ ID NO: 13 (PgB5-1), SEQ ID NO: 48 (PgB1-3), SEQ ID NO: 50 (PgB1-4), SEQ ID NO: 51 (PgB2-3), SEQ ID NO: 52 (PgB2-4), SEQ ID NO: 53 (PgB3-3), SEQ ID NO: 54 (PgB3-4), SEQ ID NO: 55 (PgB4-2), and SEQ ID NO: 56 (PgB5-2).

In an embodiment, the genetic construct may further include a third polynucleotide encoding a helper element. The third polynucleotide may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 14 (PgC1-1), SEQ ID NO: 15 (PgC2-1), SEQ ID NO: 32 (PgC1-2), SEQ ID NO: 33 (PgC1-3), and SEQ ID NO: 34 (PgC2-2). The third polynucleotide may include a sequence capable of hybridizing under conditions of one of low, moderate, or high stringency to a reference sequence selected from the group consisting of: SEQ ID NO: 14 (PgC1-1), SEQ ID NO: 15 (PgC2-1), SEQ ID NO: 32 (PgC1-2), SEQ ID NO: 33 (PgC1-3), and SEQ ID NO: 34 (PgC2-2).

In an embodiment, a genetic construct may include, consist essentially of, or consist of a sequence with at least 70, 72, 75, 80, 85, 90, 91, 92, 93, 94, 95, 96, 97, 98, 99, or 100% to a reference sequence selected from the group consisting of: SEQ ID NO: 16 (PgA1-3:B1-3), SEQ ID NO: 17 (PgA1-4:B1-4), SEQ ID NO: 18 (PgA1-3:B2-4), SEQ ID NO: 19 (PgA1-4:B2-14), SEQ ID NO: 20 (PgA1-3:B3-3), SEQ ID NO:21 (PgA1-4:B3-4), SEQ ID NO: 22 (PgA1-3:B4-2), SEQ ID NO: 23 (PgA1-3:B5-2), SEQ ID NO: 37 (PgA2-4:B1-5), and SEQ ID NO: 38 (PgA1-5:B1-5). The genetic construct may include a sequence capable of hybridizing under conditions of one of low, moderate, or high stringency to a reference sequence selected from the group consisting of: SEQ ID NO: 16 (PgA1-3:B1-3), SEQ ID NO: 17 (PgA1-4:B1-4), SEQ ID NO: 18 (PgA1-3:B2-4), SEQ ID NO: 19 (PgA1-4:B2-14), SEQ ID NO: 20 (PgA1-3:B3-3), SEQ ID NO:21 (PgA1-4:B3-4), SEQ ID NO: 22 (PgA1-3:B4-2), SEQ ID NO: 23 (PgA1-3:B5-2), SEQ ID NO: 37 (PgA2-4:B1-5), and SEQ ID NO: 38 (PgA1-5:B1-5).

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity may be measured by the Basic Local Alignment Search Tool (BLAST; Altschul, S. F., Gish, W., Miller, W., Myers, E. W. & Lipman, D. J, 1990 "Basic local alignment search tool." J. Mol. Biol. 215:403-410, which is incorporated herein by reference as if fully set forth).

In an embodiment, the toxin binding ligand may be a derivative of a human or non-human anthrax toxin receptor protein. The toxin binding ligand may be a derivative of a bacterial protein specifically binding PA protein. The toxin binding ligand may be a variant ATR from a human or a non-human animal. The toxin binding ligand may be a variant of B. anthracis LF and EF proteins. A variant may include an amino acid sequence with at least 70, 75, 80, 85, 90, 91, 92, 93, 94, 95, 96, 97, 98, 99 or 100% identity to an amino acid sequence of native toxin-binding proteins.

Variants may include conservative amino acid substitutions, i.e., substitutions with amino acids having similar properties. Conservative substitutions may be a polar for polar amino acid (Glycine (G), Serine (S), Threonine (T), Tyrosine (Y), Cysteine (C), Asparagine (N) and Glutamine (Q)); a non-polar for non-polar amino acid (Alanine (A), Valine (V), Thyptophan (W), Leucine (L), Proline (P), Methionine (M), Phenilalanine (F)); acidic for acidic amino acid Aspartic acid (D), Glutamic acid (E)); basic for basic amino acid (Arginine (R), Histidine (H), Lysine (K)); charged for charged amino acids (Aspartic acid (D), Glutamic acid (E), Histidine (H), Lysine (K) and Arginine (R)); and a hydrophobic for hydrophobic amino acid (Alanine (A), Leucine (L), Isoleucine (I), Valine (V), Proline (P), Phenilalanine (F), Tryptophan (W) and Methionone (M)). Conservative nucleotide substitutions may be made in a nucleic acid sequence by substituting a codon for an amino acid with a different codon for the same amino acid. Variants may include non-conservative substitutions.

In an embodiment, fragments of a toxin binding ligand, a carrier protein or a helper element are provided. Fragments may include 100, 150, 200, 300, 400, 600, contiguous amino acids or more, such as 700.

In an embodiment, fragments of CMG2 or PA-LF proteins are provided. Fragments may include 100, 150, 200, 300, 400, 500 contiguous amino acids or more, such as 580.

The functionality of a recombinant protein, variants or fragments thereof, may be determined using any methods. The functionality may include conferring ability to bind the components of the anthrax toxin in a solution as determined by immunodetection methods. The functionality may be assessed using protection of cells growing in vitro. The functionality of a protein, or variants, or fragments thereof, may be assessed based on an ability to protect animals after administering of a recombinant antitoxin following of the infection of animals with the causative agent of anthrax.

In an embodiment, polynucleotides are provided having a sequence as set forth in any one of the nucleic acids listed herein or the complement thereof. In an embodiment, polynucleotides having a sequence that hybridizes to a nucleic acid having the sequence of any nucleic acid listed herein or the complement thereof are provided. In an embodiment, the hybridization conditions are low stringency conditions. In an embodiment, the hybridization conditions are moderate stringency conditions. In an embodiment, the hybridization conditions are high stringency conditions. Examples of hybridization protocols and methods for optimization of hybridization protocols are described in the following book: in Green and Sambrook. Molecular Cloning: a Laboratory Manual. 4th ed. Spring Harbor, N.Y.: Cold Spring Harbor Laboratory Press, which is incorporated by reference in as if fully set forth.

Moderate conditions may be as follows: filters loaded with DNA samples are pretreated for 2-4 hours at 68° C. in a solution containing 6× citrate buffered saline (SSC; Amresco, Inc., Solon, Ohio), 0.5% sodium dodecyl sulfate (SDS; Amresco, Inc., Solon, Ohio), S×Denhardt's solution (Amresco, Inc., Solon, Ohio), and denatured salmon sperm (Invitrogen Life Technologies, Inc. Carlsbad, Calif.). Hybridization is carried in the same solution with the following modifications: 0.01 M EDTA (Amresco, Inc., Solon, Ohio), 100 μg/ml salmon sperm DNA, and 5-20×10$^6$ cpm $^{32}$P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.), where:

$$Tm=81.5+16.61 \ Log_{10}([Na^+]/(1.0+0.7[Na^+]))+0.41 \ (\%[G+C])-(500/n)-P-F;$$

[Na+]=Molar concentration of sodium ions;
%[G+C]=percent of G+C bases in DNA sequence;
N=length of DNA sequence in bases;
P=a temperature correction for % mismatched base pairs (~1° C. per 1% mismatch);
F=correction for formamide concentration (=0.63° C. per 1% formamide).

Filters are exposed for development in an imager or by autoradiography.

Low stringency conditions refers to hybridization conditions at low temperatures, for example, between 37° C. and 60° C., and the second wash with higher [Na$^+$] (up to 0.825M) and at a temperature 40° C. to 48° C. below Tm. High stringency refers to hybridization conditions at high temperatures, for example, over 68° C., and the second wash with [Na+]=0.0165 to 0.0330M at a temperature 5° C. to 10° C. below Tm.

In an embodiment, polynucleotides having a sequence that has at least 75, 80, 85, 90, 91, 92, 93, 94, 95, 96, 97, 98, 99 or 100% identity along its length to a contiguous portion of a nucleic acid having any one of the sequences set forth herein or the complements thereof are provided. The contiguous portion may be the entire length of a sequence set forth herein or the complement thereof.

In an embodiment, isolated nucleic acids, polynucleotides, or oligonucleotides are provided having a portion of the sequence as set forth in any one of the nucleic acids listed herein or the complement thereof. These isolated nucleic acids, polynucleotides, or oligonucleotides are not limited to but may have a length in the range from 10 to full length, 10 to 1000, 10 to 900, 10 to 800, 10 to 10 to 600, 10 to 500, 10 to 400, 10 to 300, 10 to 200, 10 to 100, 10 to 90, 10 to 80, 10 to 70, 10 to 60, 10 to 50, 10 to 40, 10 to 35, 10 to 30, 10 to 25, 10 to 20, 10 to 15, or 20 to 30 nucleotides or 10, 15, 20 or 25 nucleotides. An isolated nucleic acid, polynucleotide, or oligonucleotide having a length within one of the above ranges may have any specific length within the range recited, endpoints inclusive. The recited length of nucleotides may start at any single position within a reference sequence (i.e., any one of the nucleic acids herein) where enough nucleotides follow the single position to accommodate the recited length. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a portion of a sequence as set forth in any one of the nucleic acids listed herein. In an embodiment, a hybridization probe or primer hybridizes along its length to a corresponding length of a nucleic acid having the sequence as set forth in any one of the nucleic acids listed herein. In an embodiment, the hybridization conditions are low stringency. In an embodiment, the hybridization conditions are moderate stringency. In an embodiment, the hybridization conditions are high stringency.

The variants or fragments of the polynucleotides encoding the recombinant proteins may be identified, isolated or synthesized by any known methods. For optimal expression in a host cell, a polynucleotide sequence encoding a first and a second protein may be codon-optimized by adapting the codon usage to that most preferred in host genes. In case the host is a plant, codon usage may be optimized to native plant genes (Itakura et al. 1977 Science 198:1056; Bennetzen et al. 1982 J Mol Chem 257: 3026) using codon usage tables. Codon usage table are publicly available for various plant species (Nakamura et al. 2000 Nucl Acid Res 28: 292).

In an embodiment, a genetic construct having a nucleic acid encoding a recombinant protein may be provided in an expression cassette suitable for expression in plant cell, tissues, organs, and/or whole organism.

The expression of any one of the first and the second polynucleotide sequences or the third polynucleotide sequence of the genetic construct included the expression cassette may be under control of a promoter, which provides for transcription of the polynucleotide in a plant. The promoter may be a constitutive promoter, or tissue specific, or an inducible promoter. A constitutive promoter may provide transcription of the polynucleotides throughout most cells and tissues of the plant and during many stages of development but not necessarily all stages. An inducible promoter may initiate transcription of the polynucleotide sequences only when exposed to a particular chemical or environmental stimulus. A tissue specific promoter may be capable of initiating transcription in a particular plant tissue. Plant tissue may be, but is not limited to, a stem, leaves, trichomes, anthers, or seeds. Constitutive promoter may be, but is not limited to, the Cauliflower Mosaic Virus (CaMV) 35S promoter, the Cestrum Yellow Leaf Curling Virus promoter (CMP), or the CMP short version (CMPS), the Rubisco small subunit promoter, or the maize ubiquitin promoter.

An expression cassette may further include a terminator sequence, which terminates transcription of the first and the second polynucleotide sequences or the third polynucleotide sequence and may be included at the 3' end of a transcriptional unit of the expression cassette. The terminator may be derived from a variety of plant genes. The terminator may be derived from the nopaline synthase or octopine synthase genes of *Agrobacterium tumefaciens*.

In an embodiment, an expression cassette is provided in a vector. For stable plant transformation, an expression cassette may be included in a T-DNA binary vector or a co-integrate vector. A vector may include multiple cloning sites to facilitate molecular cloning and selection markers to facilitate selection. A selection marker may be, but is not limited to, a neomycin phosphotransferase (npt) gene conferring resistance to kanamycin, a hygromycin phosphotransferase (hpt) gene conferring resistance to hygromycin, and a bar gene conferring resistance to phosphinothricin.

For transient expression of the toxin binding ligands, carrier proteins, or helper peptides in a plant, an expression cassette may be included in a viral-based vector. A viral-based vector may be obtained from a virus, which is not infectious for a mammalian object and therefore not requiring elimination of the vector components from the compositions herein. A viral-based vector may be, but is not limited to, a tobacco mosaic virus (TMV)-based vector or a potato virus X (PVX)-based vector.

In an embodiment, a transgenic plant is provided. The transgenic plant may include a genetic construct. The genetic construct may include a first polynucleotide and a second polynucleotide. The first polynucleotide may encode a toxin binding ligand. The second polynucleotide may encode a carrier-protein. The carrier-protein may be but is not limited to Fc-IgA, Fc-IgG, Fc-IgM, oleosin, or VP2 coat protein. The toxin binding ligand may be a capillary morphogenesis protein 2. The toxin binding ligand may be a PA-LF protein. The first polynucleotide may encode the capillary morphogenesis protein 2 or a PA-LF protein. The first polynucleotide may include, consist essentially of, or consisting of a sequence with at least 70, 72, 75, 80, 85, 90, 91, 92, 93, 94, 95, 96, 97, 98, 99, or 100% to a reference sequence selected from the group consisting of: SEQ ID NO: 1 (PgA1-1), SEQ ID NO: 2 (PgA1-2), SEQ ID NO: 3 (PgA2-1), SEQ ID NO: 4 (PgA2-2), SEQ ID NO: 5 (A2/PA-LF), SEQ ID NO: 47 (PgA1-3), SEQ ID NO: 49 (PgA1-4), SEQ ID NO: 57 (PgA2-4), and SEQ ID NO: 58 (PgA1-5). The second polynucleotide may include, consists essentially of, or consists of a sequence with at least 70, 72, 75, 80, 85, 90, 91, 92, 93, 94, 95, 96, 97, 98, 99, or 100% to a reference sequence selected from the group consisting of: SEQ ID NO:6 (PgB1-1), SEQ ID NO: 7 (PgB2-1), SEQ ID NO: 8 (PgB3-1), SEQ ID NO: 9 (PgB1-2), SEQ ID NO: 10 (PgB2-2), SEQ ID NO: 11 (PgB3-2), SEQ ID NO: 12 (PgB4-1), SEQ ID NO: 13 (PgB5-1), SEQ ID NO: 48 (PgB1-3), SEQ ID NO: 50 (PgB1-4), SEQ ID NO: 51 (PgB2-3), SEQ ID NO: 52 (PgB2-4), SEQ ID NO: 53 (PgB3-3), SEQ ID NO: 54 (PgB3-4), SEQ ID NO: 55 (PgB4-2), and SEQ ID NO: 56 (PgB5-2).

The transgenic plant may further include a third polynucleotide. The third polynucleotide may encode a helper element. The third polynucleotide may include, consist essentially of, or consist of a sequence with at least 70, 72, 75, 80, 85, 90, 91, 92, 93, 94, 95, 96, 97, 98, 99, or 100% to a reference sequence selected from the group consisting of: SEQ ID NO: 14 (PgC1-1), SEQ ID NO: 15 (PgC2-1), SEQ ID NO: 32 (PgC1-2), SEQ ID NO: 33 (PgC1-3), and SEQ ID NO: 34 (PgC2-2).

The transgenic plant may include a genetic construct that includes, consists essentially of, or consists of a sequence with at least 70, 72, 75, 80, 85, 90, 91, 92, 93, 94, 95, 96, 97, 98, 99, or 100% to a reference sequence selected from the group consisting of: SEQ ID NO: 16 (PgA1-3:B1-3), SEQ ID NO: 17 (PgA1-4:B1-4), SEQ ID NO: 18 (PgA1-3:B2-4), SEQ ID NO: 19 (PgA1-4:B2-14), SEQ ID NO: 20 (PgA1-3:B3-3), SEQ ID NO:21 (PgA1-4:B3-4), SEQ ID NO: 22 (PgA1-3:B4-2), SEQ ID NO: 23 (PgA1-3:B5-2), SEQ ID NO: 37 (PgA2-4:B1-5) and SEQ ID NO: 38 (PgA1-5:B1-5).

The transgenic plant may be any plant, or a part of a plant. The part of a plant may be a stem, a leaf, a flower, a seed, or a callus. The transgenic plant may be a progeny, or descendant of a transgenic plant. The transgenic plant may be obtained through crossing of a transgenic plant and non-transgenic plant as long as it retains the genetic construct as described above. The transgenic plant may be a crop cultivated for purposes of obtaining food, feed or plant derived products including carbohydrates, oil, and medicinal ingredients. A crop plant may be selected from group consisting of: tomato, tobacco, pepper, eggplant, lettuce, sunflower, oilseed rape, broccoli, cauliflower and cabbage crops, cucumber, carrot, melon, watermelon, pumpkin, squash, sugar beet, peanut, chard, swiss chard, soybean, cotton, beans, cassava, potatoes, sweet potato, okra, barley, pearl millet, wheat, rye, buckwheat, sorghum, rice. The transgenic plant may include forage grasses. The transgenic plant may include tree species and fleshy fruit species. The transgenic plants may include grapes, peaches, plums, cherries, strawberries, cranberries, mangos, and bananas.

The transgenic plant may be a medicinal plant. A medicinal plant may be a plant thought to have medicinal property and used in herbalism. A medicinal plant may be selected from a group consisting of, but not limited to: *Arthemis nobilis, Calendula officinalis, Caragana sinica, Codonopsis pilosulae, Echinacea angustifolia, Hedyotis diffusa, Houttuynia cordata, Hydrastis canadensis, Kalanchoe pinnata, Lonicera japonica, Morinda officinalis*, and *Oenothera odorata*.

The transgenic plant may be edible or medicinal plants. Edible or medicinal plants may not contain health-threatening components. Edible or medicinal plants may not require any special purification and may be used similar to conventional biologically active dietary supplements produced from plants.

In an embodiment, a method for producing a recombinant protein in a plant is provided. The method may include steps of contacting a plant with a genetic construct. The genetic construct may include a nucleic acid encoding the recombinant protein. The recombinant protein may include a toxin binding ligand fused to a carrier protein. The carrier protein may be but is not limited to Fc-IgA, Fc-IgG, Fc-IgM, oleosin, or VP2 coat protein. The method may also include obtaining a plant that includes the genetic construct and expressing the recombinant protein.

In an embodiment of the method, the toxin binding ligand may be a capillary morphogenesis protein 2. The toxin binding ligand may be a PA-LF protein.

The step of contacting may include contacting with a vector providing for stable transformation of a plant. The step of contacting may include contacting with a vector providing for transient expression in a plant. The vector may include a first polynucleotide encoding a toxin binding ligand and a second polynucleotide sequence encoding a carrier protein. A method may further include contacting a plant with another vector that includes a third polynucleotide encoding a helper element.

In an embodiment, the step of contacting may include contacting with the nucleic acid that may include a first polynucleotide encoding a toxin binding ligand. The nucleic acid may also include a second polynucleotide encoding a carrier protein. The first polynucleotide may include, consists essentially of, consists of a sequence with at least 70, 72, 75, 80, 85, 90, 91, 92, 93, 94, 95, 96, 97, 98, 99, or 100% to a reference sequence selected from the group consisting of: SEQ ID NO: 1 (PgA1-1), SEQ ID NO: 2 (PgA1-2), SEQ ID NO: 3 (PgA2-1), SEQ ID NO: 4 (PgA2-2), SEQ ID NO: 5 (A2-3/PA-LF), SEQ ID NO: 47 (PgA1-3), SEQ ID NO: 49 (PgA1-4), SEQ ID NO: 57 (PgA2-4) SEQ ID NO: 57 (PgA2-4), and SEQ ID NO: 58 (PgA1-5). The second polynucleotide may include, consists essentially of, consists of a sequence with at least 70, 72, 75, 80, 85, 90, 91, 92, 93, 94, 95, 96, 97, 98, 99, or 100% to a reference sequence selected from the group consisting of: SEQ ID NO:6 (PgB1-1), SEQ ID NO: 7 (PgB2-1), SEQ ID NO: 8 (PgB3-1), SEQ ID NO: 9 (PgB1-2), SEQ ID NO: 10 (PgB2-2), SEQ ID NO: 11 (PgB3-2), SEQ ID NO: 12 (PgB4-1), SEQ ID NO: 13 (PgB5-1), SEQ ID NO: 48 (PgB1-3), SEQ ID NO: 50 (PgB1-4), SEQ ID NO: 51 (PgB2-3), SEQ ID NO: 52 (PgB2-4), SEQ ID NO: 53 (PgB3-3), SEQ ID NO: 54 (PgB3-4), SEQ ID NO: 55 (PgB4-2), and SEQ ID NO: 56 (PgB5-2).

In an embodiment of the method, the nucleic acid may further include a third polynucleotide encoding a helper element. The third polynucleotide may include, consists essentially of, or consists of a sequence with at least 70, 72, 75, 80, 85, 90, 91, 92, 93, 94, 95, 96, 97, 98, 99, or 100% to a reference sequence selected from the group consisting of: SEQ ID NO: 14 (PgC1-1), SEQ ID NO: 15 (PgC2-1), SEQ ID NO: 32 (PgC1-2), SEQ ID NO: 33 (PgC1-3), and SEQ ID NO: 34 (PgC2-2).

In an embodiment of the method, the step of contacting may include contacting with a genetic construct that may include, consists essentially of, or consists of a sequence with at least 70, 72, 75, 80, 85, 90, 91, 92, 93, 94, 95, 96, 97, 98, 99, or 100% to a reference sequence selected from the group consisting of: SEQ ID NO: 16 (PgA1-3:B1-3), SEQ ID NO: 17 (PgA1-4:B1-4), SEQ ID NO: 18 (PgA1-3:B2-4), SEQ ID NO: 19 (PgA1-4:B2-14), SEQ ID NO: 20 (PgA1-3:B3-3), SEQ ID NO:21 (PgA1-4:B3-4), SEQ ID NO: 22 (PgA1-3:B4-2), SEQ ID NO: 23 (PgA1-3:B5-2), SEQ ID NO: 37 (PgA2-4:B1-5), and SEQ ID NO: 38 (PgA1-5:B1-5).

In an embodiment of the method, the recombinant protein including the toxin binding ligand and a carrier-protein that may be capable of protecting a subject against anthrax toxin. The helper element may help to establish secondary structures from the molecules of the recombinant protein consisting of the toxin binding ligand and the carrier protein.

The plant may be created by *Agrobacterium*-mediated transformation using a vector that includes a nucleic acid encoding the recombinant protein herein. The transgenic plant may be created by other methods for modifying plants. The transgenic plant may be created by direct uptake of plasmid DNA. The transformed plant may be stably transformed. The stably transformed plant may incorporate the genetic construct into the genome of the plant.

The plant may be transformed with a viral vector for transient expression of a recombinant protein in a plant. The viral vector may be delivered to a plant by any method. For reference, see U.S. Pat. Nos. 5,889,190; 5,889,191; 5,316,931; 5,589,367; 7,667,092; 7,670,801; 7,763,458; 8,093,458; and 8,003,381, all of which are incorporated by reference herein as if fully set forth. Viral vectors may be T-DNA vectors. Plants may be infiltrated with a diluted *Agrobacterium* suspension carrying T-DNAs encoding viral replicons. The resulting plants may have a high copy number of RNA molecules that encode a recombinant protein. A recombinant protein may be produced in a transgenic plant in a short period of time. A recombinant protein may be produced in the transgenic plant in 1, 2, 3, 4, 5, 6, 7, 8, 9, 10, 11, 12, 13, 14 or more days after transformation. The transgenic plants may have a high copy number of RNA molecules that encode recombinant proteins. Recombinant proteins may be produced in plants rapidly and in increasing volumes of biomass containing recombinant proteins that may not require changes in growing conditions. Features of transient expression system may include non-integration of external genes into plant genome, and thus reducing or eliminating the risk of releasing transgene into environment through pollen, seeds, or other routs. Further, no intact and replication-competent virus may be produced, thus, reducing or eliminating the risk of virus mediated spreading of the recombinant genes. Protein production may be performed in closed indoor settings.

In an embodiment, the method may include obtaining a plant expressing the recombinant antitoxin binding protein. The method may include also obtaining a plant expressing the helper peptide. The method may further include crossing the plant expressing the recombinant protein with the plant expressing the helper element.

An embodiment of any of the method may further include breeding the transgenic plant and obtaining its progeny, or its descendant. The progeny or the descendant may include the genetic construct.

In an embodiment, any of the method further may include obtaining a seed of the transgenic plant. The seed may include the genetic construct that includes the recombinant protein.

The method may further include isolating and purifying the recombinant protein from the plant.

In an embodiment a method for preparing a composition effective for treating or preventing an anthrax infection in a subject is also provided. The method may include providing a recombinant protein produced by any methods described herein. The therapeutic composition may include a toxin binding ligand (component A) alone. The therapeutic composition may include a toxin binding ligand fused to a carrier-protein (components A and B). The therapeutic composition may include a mixture of two or more recombinant antitoxins of different types related to different component B parts. The therapeutic composition may include any composition described herein and a helper element (component C). The plant-derived therapeutic compositions may neutralize, delay, or attenuate the fatal action of the anthrax toxin in a subject.

In an embodiment, a plant-derived therapeutic composition may include active agents. Active agents may include at least one of recombinant antitoxin proteins produced in plants. The therapeutic composition may be therapeutically effective. Therapeutic efficacy may depend on effective amounts of active agents and time of administering necessary to achieve the desired result.

In an embodiment, the therapeutic compositions in a "therapeutically effective amount", i.e., the amount sufficient to protect against accumulation of active deadly toxin in serum, or disappearance of disease symptoms in a subject. Disappearance of disease symptoms may be assessed by decrease of internalization of active LF or EF components of the anthrax toxin by living cells in the subject's body or by increase of a surviving time of the subject after contact with pathogen. The plant-derived compositions may be administered using any amount and any route of administration effective for a protective action.

The exact dosage may be chosen by the physician based on a variety of factors and in view of individual patients. Dosage and administration may be adjusted to provide sufficient levels of the active agent or agents or to maintain the desired effect. For example, factors which may be taken into account include time of potential infection, the type and amount of infection agent and severity of a disease; weight of the patient; availability of other means for treatment or prophylaxis.

Therapeutic efficacy and toxicity of active agents in a composition may be determined by standard pharmaceutical procedures, for example, by determining the therapeutically effective dose of the agent in 50% of the population ($ED_{50}$) and the lethal dose to 50% of the population ($LD_{50}$) with or without therapeutic agent in cells cultured in vitro or experimental animals. Plant-derived therapeutic compositions may be evaluated based on the dose ratio of toxic to therapeutic effects ($LD_{50}/ED_{50}$), called the therapeutic index, the largest value of which may be used for assessment. The data obtained from and animal studies may be used in formulating a dosage for human use.

The therapeutic dose according to currently accepted norm in animal models of anthrax infection may be at least 50 microgram (50 μg) of antitoxin/dose/animal. As plant-based recombinant antitoxin may be readily produced and inexpensively engineered and designed and stored, lesser or greater doses for large animals may be economically feasible.

In an embodiment, the method may also include providing the therapeutic composition that includes a pharmaceutically acceptable carrier. The "pharmaceutically acceptable carrier" refers to solvents, diluents, preservatives, dispersion or suspension aids, isotonic agents, thickening or emulsifying agents, solid binders, and lubricants, appropriate for the particular dosage form. The pharmaceutically acceptable carrier may be any known carrier that may be used in formulating pharmaceutical compositions and knows techniques for the preparation thereof. See *Remington's Pharmaceutical Sciences* Ed. by Gennaro, Mack Publishing, Easton, Pa., 1995. The pharmaceutically acceptable carriers may include, but are not limited to Ringer's solution, isotonic saline, starches, potato starch, sugars, glucose, powdered tragacant, malt, gelatin, talc, cellulose and its derivatives, ethyl cellulose, sodium carboxymethyl cellulose, cellulose acetate excipients, cocoa butter, suppository waxes, agar, alginic acid, oils, cottonseed oil, peanut oil, safflower oil, sesame oil, olive oil, soybean oil, corn oil, glycols, propylene glycol, esters, ethyl laurate, ethyl oleate, buffering agents, aluminum hydroxide, magnesium hydroxide, phosphate buffer solutions, pyrogen-free water, ethyl alcohol, other non-toxic compatible lubricants, sodium lauryl sulfate, magnesium stearate, coloring agents, releasing agents, coating agents, sweetening, flavoring and perfuming agents. Pharmaceutically acceptable carriers may also include preservatives and antioxidants.

In an embodiment, the method includes providing an adjuvant. The adjuvant may be any adjuvant. As used herein, the term "adjuvant" refers to a pharmacological or immunological agent which when administered with an antigen nonspecifically enhances the recipient's response to that antigen. The adjuvant may be but is not limited to Alum, oil-in-water nannoemulsion (MF59™), the glycolipid monophosphoryl lipid A (MPL®), virus-like particles (VLP), the cholera toxin B subunit (CTB), montanides ISA51 and ISA720, saponines Quil-A, ISCOM and QS-21, syntax adjuvant formulation (SAF), muramyl dipeptides (MDP), immunostimulatory oligonucleotides, TLR ligands, *Escherichia coli* heat-labile exotoxin, or lipid-based adjuvants (Vajdy et al., 2004 Imm and Cell Biol 82:617; Schroder et al., 1999 Vaccine 17:2096, all of which are incorporated by reference herein as if fully set forth).

In an embodiment, a method of protecting a subject against anthrax infection is provided. The method may include providing a composition that includes a recombinant protein. The recombinant protein may include a toxin binding ligand fused to a carrier-protein. The carrier protein may be a protein selected from the group consisting of: Fc-IgA, Fc-IgG, Fc-IgM, oleosin, and VP2 coat protein. The composition may effective in preventing or reducing at least one symptom of an anthrax infection in a subject. The method may also include administering the composition to the subject in need thereof.

In an embodiment of the method, the toxin binding ligand may be a capillary morphogenesis protein 2. The toxin binding ligand may be a PA-LF protein. The toxin binding ligand may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 24 (A1-CMG2), SEQ ID NO: 25 (A2/PA-LF) and SEQ ID NO: 60 (PgA1-5).

In an embodiment of the method, the carrier-protein may include, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 26 (B1), SEQ ID NO: 27 (B2), SEQ ID NO: 28 (B3), SEQ ID NO: 29 (B4) and SEQ ID NO: 30 (B5).

In an embodiment of the method, the recombinant protein may include, consist essentially of, or consist of a sequence with at least 70, 72, 75, 80, 85, 90, 91, 92, 93, 94, 95, 96, 97, 98, 99, or 100% identity to a reference sequence of SEQ ID NO: 31 (PgA1-1:B1-1).

In an embodiment, the subject may be a mammal. The mammal may be but is not limited to an agricultural animal, an equine, a high value zoo animal, or a research animal. The mammal may be a human.

In an embodiment, the step of administering the composition may include a route selected from the group consisting of: intravenous, intramuscular, intraperitoneal, intradermal, mucosal, cutaneous, and subcutaneous. The step of administering may be achieved through intranasal administration. The intranasal administration may include inhalation or nasal drops. A therapeutic composition may be administered to a recipient by any routes. A therapeutic composition may be introduced by injection, inhalation, oral, or intranasal route of administration. A therapeutic composition may be introduced by a parenteral or mucosal route of administration. Routes may include administering a composition orally, intrapulmonaryl), transdermally, rectally, intravaginally, intraperitoneally, intracisternally, and or ectopically. A mucosal route may include administering a therapeutic composition to any mucosal surface of the body of the recipient. Mucosal administration differs from "systemic" or "parenteral" administration. Systemic administration may include administering compositions to a non-mucosal surface, e.g., intraperitoneal, intramuscular, sub-, or transcutaneous, intra- or transdermal, or intravenous administration.

In an embodiment, the step of administering may be achieved by using a formulation with an appropriate pharmaceutically acceptable carrier in a desired dosage. A therapeutic composition may be administered in liquid dosage forms. Liquid dosage forms may be prepared for oral, nasal, inhalation, or transdermal administration. Liquid dosage forms may include, but not limited to, pharmaceutically acceptable emulsions, microemulsions, solutions, and suspensions. Liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters or sorbitan, and mixtures of thereof. Besides inert diluents, the compositions may also include ingredients stimulating protein translocation via mucosal tissues and/or absorption/permeability enhancers including but not limited to bile salts, surfactants, fusidic acid derivates, phosphatidylcholines, cyclodextrines, alcohols, low molecular weight polyethylene glycol etc. Liquid dosage forms may be available in forms optimal for use with inhalator devices.

Dosage forms for topical or transdermal administration of a therapeutical composition may include ointments, pastes, creams, lotions, gels, powders, solutions, sprays, inhalant, or patches. Powders and sprays may content therapeutic proteins admixed with excipients such as talc, silicic acid, aluminum hydroxide, calcium silicates, polyamide powder, or mixture of these substances. Sprays may additionally contain customary propellants, for example, chlorofluorohydrocarbons. The therapeutic proteins may be admixed under sterile conditions with a pharmaceutically acceptable carrier and any needed preservatives or buffers as may be appropriate.

In an embodiment, administering the compositions may include a direct needle-free infusion of the raw, concentrated or partially purified extract of plants containing recombinant protein into human or non-human animal bloodstream. The step of administering may be achieved with the help of existing conventional devices and techniques enhancing absorption/permeability of biological surfaces. These devices or techniques may include but not limited to transdermal patches adapted to the purposes of this invention, or pulmonary delivery through an immunoglobulin transport pathway using conventional inhalators, intranasal spraying, or feeding the subject plant extract.

In an embodiment, administering of a plant-derived therapeutic composition may be a preventive treatment of subjects to promote emergency post-infection prophylaxis of a contact with the infectious agent. Administering of a plant-derived composition may be a therapeutic measure for neutralization anthrax toxin produced by bacterial pathogen Bacillus anthracis and minimizing complications associated with accumulation of deadly toxin in patients infected with the pathogen bacteria. Administering the plant-derived composition may be used for treatment of a variety of, symptoms and consequences of various forms of anthrax disease arising from infection with pathogenic bacteria Bacillus anthracis. Plant-derived therapeutic compositions may be useful to treat patients being in contact with anthrax toxin, pathogen, infected animal or human, belonging to a group of risk of biological weapon attack.

In an embodiment, the method may further include measuring cell viability in the presence of different concentrations of the anthrax toxin, wherein cell viability is a percentage of surviving cells protected by the antitoxin in comparison to the complete lysis in the control.

In an embodiment, the method may further include measuring survival of animals after challenging with lethal concentration of the anthrax toxin or B. anthracis spores, followed by administration of protective amounts of the recombinant antitoxin. The survival may be a percentage of live animals protected by the antitoxin in comparison to unprotected objects in the control.

A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. The present application mentions various patents, scientific articles, and other publications, each of which is hereby incorporated in its entirety by reference.

Further embodiments herein may be formed by supplementing an embodiment with one or more element from any one or more other embodiment herein, and/or substituting one or more element from one embodiment with one or more element from one or more other embodiment herein. Further embodiments herein may be described by reference to any one of the appended claims following claim 1 and reading the chosen claim to depend from any one or more preceding claim.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1. Recombinant Antitoxin Proteins Optimized for Expression in Plants

A soluble extracellular domain (aa 35-220) of the human CMG2 protein, sCMG2 (component A1), capable of binding PA protein and neutralization of the anthrax toxin (Scobie et al., 2005) or a fusion of the component A1 with the human IgG1 Fc-fragment (component B1), resulting in a component A1-B1 recombinant antitoxin, were chosen to first to test in a transient plant expression system. Expression cassettes were designed with or without ER targeting and retention signals and two commercial affinity tags (c-myc and 6×His). All cassettes were sub-cloned into a plant transformation vector suitable for transient expression together with commercially available helper plasmids.

Further optimization of the human CMG2 extracellular domain (amino acids 35-220) included the removal of a native signal peptide, the transmembrane domain and the cytoplasmic tail and resulted in Component A1 (PgA1). Fusion of a human CMG2 soluble extracellular domain (aa 35-220) with a human IgG1 Fc-fragment (Component B1, PgB1) resulted in Component A1-B1 (PgA1-B1) constructs. All sequences were optimized in a stepwise fashion as described in Table 1 using ELISA and Western blots for experimental quantitative confirmation.

TABLE 1

Stepwise optimization of therapeutic proteins for expression in plants

| Variable parameter | Outcome |
|---|---|
| 1. Sequence analysis and genus/species-specific optimization to improve overall yields of recombinant protein | Analysis of codon usage, mRNA thermostability, cryptic intron splice sites, and polyA signals Evaluation and correction of sequences |
| 2. Optimal days post-infiltration (transient transformation only) | Expression at different time points post infiltration |
| 3. ER localization signal choice | Expression with and without targeting signal sequences |
| 4. ER retention signal presence | Expression with and without C-terminal HDEL (SEQ ID NO: 64)/ KDEL (SEQ ID NO: 65) peptide |
| 5. Affinity tags selection | Expression and recovery with commercially available tags (c-Myc and 6xHis) |
| 6. *N. benthamiana* glycosylation in knock-out mutants (transient transformation only) | Expression and functionality in a model wild type plant and glycosylation knockout mutants that confer mammalian type glycans |

Using the strategies outlined in Table 1 the nucleic acid sequences encoding the sCMG2-based recombinant subunit antitoxin and the recombinant Fc-fusion antitoxin were optimized for a better plant-specific production.

Each of the expression cassettes encoding the recombinant polypeptides also contained specific restriction/ligation sites required for direct subcloning into the plasmid carrier. The 5' terminal region positioned at the NcoI site CCATGG was introduced in frame with the Kawasaki motif or Kozak-like sequence immediately before the initiation translation ATG codon 5'-gacaccATGG (SEQ ID NO: 39). The respective BglII and SacI sites were identified before and after the stop codon at the 3' terminal region AGATCTccaataaGAGCTC-3' (SEQ ID NO: 40) in both constructs. Additionally, the NotI site as follows: 5'-tcttGCGGCCGCagga-3' (SEQ ID NO: 41), was identified between Components A1 and B1 in the PgA1-B1 construct. These cloning sites were eliminated from the rest of the sequence body during the process of optimization.

PgA1 and PgA1-B1 expression cassettes were synthesized. These cassettes contained the synthetic anthrax toxin receptor sCMG2 or synthetic sCMG2 fused with the Fc fragment inserted into expression cassettes. The expression cassettes also contained C-terminus-specific tags, such as c-Myc and/or 6xHis tags, and N-terminus plant-specific intracellular targeting signals. Two targeting signal sequences included the plant BAA gene encoding the amino acid sequence MANKHLSLSLFLVLLGLSASLASG (SEQ ID NO: 42) and the plant APBP1 gene, encoding the amino acid sequence MIVLSVGSASSSPIVVVFSVALLLFYFSETSLG (SEQ ID NO: 43). A flexible linker was introduced into the PgA1-B1 construct between the synthetic sCMG2 and the Fc fragment GGGSGNS (SEQ ID NO: 44). A short peptide was also introduced in front of the flexible linker to facilitate cleavage by a mammal serum protease, such as Thrombin LVPRGS (SEQ ID NO: 45), or Factor Xa protease IEGR (SEQ ID NO: 46).

The synthetic expression cassettes were introduced into plant transformation vectors harboring compatible cloning sites for NcoI (harbors ATG, first codon and without targeting signal peptide) and SacI. At the C-terminus of the expression cassettes, affinity tags such as c-Myc and/or 6xHis were linked to endoplasmic reticulum (ER) retention signal HDEL (SEQ ID NO: 64) and inserted into the expression cassette immediately prior the stop codon. An Invitrogene/Geneart optimization with Gene with GeneOptimizer® sequence processing included the following parameters:

(i) Identification of the optimal sequence elements, such as restriction/ligation sites.

(ii) Elimination of cryptic splice sites and RNA destabilizing sequence elements for increased RNA stability.

(iii) Addition of RNA stabilizing sequence elements.

(iv) Codon optimization and G/C content adaptation for plant expression system.

(v) Intron removal.

(vi) Avoidance of templates compromising RNA secondary structures.

Additionally, regions with very high (>80%) or very low (<30%) GC content were avoided. For expression in plants, an average GC content of 58% was desirable. During the optimization process the following cis-acting sequence motifs were avoided: internal TATA-boxes, chi-sites and ribosomal entry sites. At-rich or GC-rich sequence stretches in codons, other RNA instability motifs, repeat sequences and RNAs secondary structures, cryptic splice donor and acceptor sites in eukaryotes. In some cases, negative cis-acting motifs were not removed.

The optimization considered successful if negative cis-acting sites which may negatively influence expression were eliminated, and GC content was adjusted to prolong mRNA half-life.

The expression cassettes included nucleic acid sequences encoding the soluble form of extracellular domain (aa 35-220) of human CMG2 protein (sCMG2, component A1) capable of binding PA protein and neutralization of the anthrax toxin; a fusion of the component A1 with human IgG1 Fc-fragment (component B1), resulting in a recombinant antitoxin, a component A1-B1. Expression cassettes were designed and tested in commercial plasmids for stable transformation/expression PgA1 Expression Cassettes.

PgA1 included a soluble extracellular domain of human CMG2 protein, sCMG2 (component A1), capable of binding PA protein and neutralization of the anthrax toxin that has no native signal peptide (amino acids 35-220), transmembrane domain and cytoplasmic tail. These elements were optimized for expression in plants and named sCMG2. PgA1 was designed for transient and stable plant transformation/expression. A 581 bp nucleic acid sequence of PgA1-1 (SEQ ID NO: 1) encoding the PgA protein (190 aa) designed for cloning in the MagnICON expression vectors is as follows:

(SEQ ID NO: 1)
CCATGGAACAACCTTCTTGTCGTCGAGCTTTTGATCTTTATTTTGT

TCTTGATAAATCTGGTTCTGTTGCTAATAATTGGATTGAAATTTATAAT

TTTGTTCAACAACTTGCTGAAAGATTTGTTTCTCCTGAAATGAGACTTT

CTTTTATTGTTTTTTCTTCTCAAGCTACTATTATTCTTCCTCTTACTGG

TGATAGAGGAAAAATTTCTAAAGGACTTGAGGATTTGAAAAGAGTTTCT

CCTGTTGGTGAAACTTATATTCATGAGGGACTTAAACTTGCTAATGAAC

AAATTCAAAAAGCTGGTGGTCTTAAAACTTCTTCTATTATTATTGCTCT

TACTGATGGAAAACTTGATGGTCTTGTTCCTTCTTATGCTGAAAAAGAA

GCTAAAATTTCAAGATCACTTGGTGCTTCTGTTTATTGTGTTGGTGTTC

TTGATTTTGAACAAGCTCAACTTGAAAGAATTGCTGATTCTAAAGAACA

AGTTTTTCCTGTTAAGGGTGGATTTCAAGCTCTTAAAGGAATTATTAAT

TCTATTCTTGCTCAATCTTGTACTGAAGATCTCCAATAAGAGCTC

A 575 bp nucleic acid sequence of PgA1-2 (SEQ ID NO: 2) encoding the PgA1 protein (190 aa) designed for stable expression is as follows:

(SEQ ID NO: 2)
CCATGGAACAACCTTCTTGTCGTCGAGCTTTTGATCTTTATTTTGT

TCTTGATAAATCTGGTTCTGTTGCTAATAATTGGATTGAAATTTATAAT

TTTGTTCAACAACTTGCTGAAAGATTTGTTTCTCCTGAAATGAGACTTT

CTTTTATTGTTTTTCTTCTCAAGCTACTATTATTCTTCCTCTTACTGG

TGATAGAGGAAAAATTTCTAAAGGACTTGAGGATTTGAAAAGAGTTTCT

CCTGTTGGTGAAACTTATATTCATGAGGGACTTAAACTTGCTAATGAAC

AAATTCAAAAAGCTGGTGGTCTTAAAACTTCTTCTATTATTATTGCTCT

TACTGATGGAAAACTTGATGGTCTTGTTCCTTCTTATGCTGAAAAAGAA

GCTAAAATTTCAAGATCACTTGGTGCTTCTGTTTATTGTGTTGGTGTTC

TTGATTTTGAACAAGCTCAACTTGAAAGAATTGCTGATTCTAAAGAACA

AGTTTTTCCTGTTAAGGGTGGATTTCAAGCTCTTAAAGGAATTATTAAT

TCTATTCTTGCTCAATCTTGTACTGAAGATCTCCAATAA

PgA1-B1 Expression Cassettes.

A soluble extracellular domain of human CMG2 protein, component A1 as described above, fused with human IgG1 Fc-fragment (component B1), resulting in a component A1-B1 recombinant antitoxin optimized for expression in plants. PgA1-B1 expression cassettes were designed for transient and stable plant transformation.

A 1286 bp nucleic acid sequence of PgA1-3:B1-3 (SEQ ID NO: 16) encoding the PgA1-B1 protein (425 aa) designed for transient expression vectors is as follows:

(SEQ ID NO: 16)
CCATGGAACAACCTTCTTGTCGTCGAGCTTTTGATCTTTATTTTGT

TCTTGATAAATCTGGTTCTGTTGCTAATAATTGGATTGAAATTTATAAT

TTTGTTCAACAACTTGCTGAAAGATTTGTTTCTCCTGAAATGAGACTTT

CTTTTATTGTTTTTCTTCTCAAGCTACTATTATTCTTCCTCTTACTGG

TGATAGAGGAAAAATTTCTAAAGGACTTGAGGATTTGAAAAGAGTTTCT

CCTGTTGGTGAAACTTATATTCATGAGGGACTTAAACTTGCTAATGAAC

AAATTCAAAAAGCTGGTGGTCTTAAAACTTCTTCTATTATTATTGCTCT

TACTGATGGAAAACTTGATGGTCTTGTTCCTTCTTATGCTGAAAAAGAA

GCTAAAATTTCAAGATCACTTGGTGCTTCTGTTTATTGTGTTGGTGTTC

TTGATTTTGAACAAGCTCAACTTGAAAGAATTGCTGATTCTAAAGAACA

AGTTTTTCCTGTTAAGGGTGGATTTCAAGCTCTTAAAGGAATTATTAAT

TCTATTCTTGCTCAATCTTGTACTGCGGCCGCAGGAGGTGGATCTGGAA

ATTCTGACAAGACCCACACCTGCCCTCCTTGCCCTGCTCCTGAGCTCCT

CGGTGGTCCTTCTGTCTTCCTCTTCCCTCCTAAGCCTAAGGACACCCTC

ATGATCTCTCGTACCCCTGAGGTCACCTGCGTCGTCGTCGACGTCTCTC

ACGAGGACCCTGAGGTCAAGTTCAACTGGTACGTCGACGGTGTCGAGGT

CCACAACGCTAAGACCAAGCCTCGTGAGGAGCAGTACAACTCTACCTAC

CGTGTCGTCTCTGTCCTCACCGTCCTCCACCAGGACTGGCTCAACGGTA

AGGAGTACAAGTGCAAGGTCTCTAACAAGGCTCTCCCTGCTCCTATCGA

GAAGACCATCTCTAAGGCTAAGGGTCAGCCTCGTGAGCCTCAGGTCTAC

ACCCTCCCTCCTTCTCGTGAGGAGATGACCAAGAACCAGGTCTCTCTCA

CCTGCCTCGTCAAGGGTTTCTACCCTTCTGACATCGCTGTCGAGTGGGA

GTCTAACGGTCAGCCTGAGAACAACTACAAGACCACCCCTCCTGTCCTC

GACTCTGACGGTTCTTTCTTCCTCTACTCTAAGCTCACCGTCGACAAGT

CTCGTTGGCAGCAGGGTAACGTCTTCTCTTGCTCTGTCATGCACGAGGC

TCTCCACAACCACTACACCCAGAAGTCTCTCTCTCTCTCTCCTGGTAAG

GACCTCTAAGAGCTC

A 1283 bp nucleic acid sequence of PgA1-4:B1-4 (SEQ ID NO: 17) encoding the PgA1-B1 protein (442 aa) designed for stable transformation is as follows:

(SEQ ID NO: 17)
CCATGGAACAACCTTCTTGTCGTCGAGCTTTTGATCTTTATTTTGT

TCTTGATAAATCTGGTTCTGTTGCTAATAATTGGATTGAAATTTATAAT

TTTGTTCAACAACTTGCTGAAAGATTTGTTTCTCCTGAAATGAGACTTT

CTTTTATTGTTTTTCTTCTCAAGCTACTATTATTCTTCCTCTTACTGG

TGATAGAGGAAAAATTTCTAAAGGACTTGAGGATTTGAAAAGAGTTTCT

CCTGTTGGTGAAACTTATATTCATGAGGGACTTAAACTTGCTAATGAAC

AAATTCAAAAAGCTGGTGGTCTTAAAACTTCTTCTATTATTATTGCTCT

TACTGATGGAAAACTTGATGGTCTTGTTCCTTCTTATGCTGAAAAAGAA

GCTAAAATTTCAAGATCACTTGGTGCTTCTGTTTATTGTGTTGGTGTTC

TTGATTTTGAACAAGCTCAACTTGAAAGAATTGCTGATTCTAAAGAACA

AGTTTTTCCTGTTAAGGGTGGATTTCAAGCTCTTAAAGGAATTATTAAT

TCTATTCTTGCTCAATCTTGTACTGCGGCCGCAGGAGGTGGATCTGGAA

ATTCTGACAAGACCCACACCTGCCCTCCTTGCCCTGCTCCTGAGCTCCT

CGGTGGTCCTTCTGTCTTCCTCTTCCCTCCTAAGCCTAAGGACACCCTC

ATGATCTCTCGTACCCCTGAGGTCACCTGCGTCGTCGTCGACGTCTCTC

ACGAGGACCCTGAGGTCAAGTTCAACTGGTACGTCGACGGTGTCGAGGT

CCACAACGCTAAGACCAAGCCTCGTGAGGAGCAGTACAACTCTACCTAC

CGTGTCGTCTCTGTCCTCACCGTCCTCCACCAGGACTGGCTCAACGGTA

AGGAGTACAAGTGCAAGGTCTCTAACAAGGCTCTCCCTGCTCCTATCGA

GAAGACCATCTCTAAGGCTAAGGGTCAGCCTCGTGAGCCTCAGGTCTAC

```
ACCCTCCCTCCTTCTCGTGAGGAGATGACCAAGAACCAGGTCTCTCTCA

CCTGCCTCGTCAAGGGTTTCTACCCTTCTGACATCGCTGTCGAGTGGGA

GTCTAACGGTCAGCCTGAGAACAACTACAAGACCACCCCTCCTGTCCTC

GACTCTGACGGTTCTTTCTTCCTCTACTCTAAGCTCACCGTCGACAAGT

CTCGTTGGCAGCAGGGTAACGTCTTCTCTTGCTCTGTCATGCACGAGGC

TCTCCACAACCACTACACCCAGAAGTCTCTCTCTCTCTCTCCTGGTAAG

GACCTCGATCTCCAAAAGCTTATTAGCGAGGAGGATCTTCATCACCATC

ACCATCACTAAGAGCTC
```

PgA1-B2 Expression Cassettes.

A soluble extracellular domain of human CMG2 protein, component A1 as described above, fused with human IgA1 Fc-fragment (component B2), resulting in a component A1-B2 recombinant antitoxin optimized for expression in plants. PgA1-B2 expression cassettes were designed for transient and stable plant transformation/expression.

A 1377 bp nucleic acid sequence of PgA1-3:B2-3 (SEQ ID NO: 18) encoding the PgA1-B2$_{Nt}$ protein (458 aa) designed for transient expression vectors is as follows:

```
                                          (SEQ ID NO: 18)
CCATGGAACAACCTTCTTGTCGTCGAGCTTTTGATCTTTATTTTGTTC

TTGATAAATCTGGTTCTGTTGCTAATAATTGGATTGAAATTTATAATTT

TGTTCAACAACTTGCTGAAAGATTTGTTTCTCCTGAAATGAGACTTTCT

TTTATTGTTTTTCTTCTCAAGCTACTATTATTCTTCCTCTTACTGGTG

ATAGAGGAAAAATTTCTAAAGGACTTGAGGATTTGAAAAGAGTTTCTCC

TGTTGGTGAAACTTATATTCATGAGGGACTTAAACTTGCTAATGAACAA

ATTCAAAAGCTGGTGGTCTTAAAACTTCTTCTATTATTATTGCTCTTA

CTGATGGAAAACTTGATGGTCTTGTTCCTTCTTATGCTGAAAAGAAGC

TAAAATTTCAAGATCACTTGGTGCTTCTGTTTATTGTGTTGGTGTTCTT

GATTTTGAACAAGCTCAACTTGAAAGAATTGCTGATTCTAAAGAACAAG

TTTTTCCTGTTAAGGGTGGATTTCAAGCTCTTAAAGGAATTATTAATTC

TATTCTTGCTCAATCTTGTACTGCGGCCGCAGGAGGTGGATCTGGAAAT

TCTGACGTCACCGTCCCTTGCCCTGTCCCTTCTACCCCTCCTACCCCTTC

CTCCTTCTACCCCTCCTACCCCTTCTCCTTCTTGCTGCCACCCTCGTCT

CTCTCTCCACCGTCCTGCTCTCGAGGACCTCCTCCTCGGTTCTGAGGCT

AACCTCACCTGCACCCTCACCGGTCTCCGTGACGCTTCTGGTGTCACCT

TCACCTGGACCCCTTCTTCTGGTAAGTCTGCTGTCCAGGGTCCTCCTGA

GCGTGACCTCTGCGGTTGCTACTCTGTCTCTTCTGTCCTCCCTGGTTGC

GCTGAGCCTTGGAACCACGGTAAGACCTTCACCTGCACCGCTGCTTACC

CTGAGTCTAAGACCCCTCTCACCGCTACCCTCTCTAAGTCTGGTAACAC

CTTCCGTCCTGAGGTCCACCTCCTCCCTCCTCCTTCTGAGGAGCTCGCT

CTCAACGAGCTCGTCACCCTCACCTGCCTCGCTCGTGGTTTCTCTCCTA

AGGACGTCCTCGTCCGTTGGCTCCAGGGTTCTCAGGAGCTCCCTCGTGA

GAAGTACCTCACCTGGGCTTCTCGTCAGGAGCCTTCTCAGGGTACCACC

ACCTTCGCTGTCACCTCTATCCTCCGTGTCGCTGCTGAGGACTGGAAGA
```

```
AGGGTGACACCTTCTCTTGCATGGTCGGTCACGAGGCTCTCCCTCTCGC

TTTCACCCAGAAGACCATCGACCGTCTCGCTGGTAAGCCTACCCACGTC

AACGTCTCTGTCGTCATGGCTGAGGTCGACGGTACCTGCTACCCAATAA

GAGCTC
```

A 1273 bp nucleic acid sequence of PgA1-4:B2-4 (SEQ ID NO: 19) encoding the PgA1-B2 protein (454 aa) designed for stable transformation vectors is as follows:

```
                                          (SEQ ID NO: 19)
CCATGGAACAACCTTCTTGTCGTCGAGCTTTTGATCTTTATTTTGTTCT

TGATAAATCTGGTTCTGTTGCTAATAATTGGATTGAAATTTATAATTTT

GTTCAACAACTTGCTGAAAGATTTGTTTCTCCTGAAATGAGACTTTCTT

TTATTGTTTTTCTTCTCAAGCTACTATTATTCTTCCTCTTACTGGTGA

TAGAGGAAAAATTTCTAAAGGACTTGAGGATTTGAAAAGAGTTTCTCCT

GTTGGTGAAACTTATATTCATGAGGGACTTAAACTTGCTAATGAACAAA

TTCAAAAGCTGGTGGTCTTAAAACTTCTTCTATTATTATTGCTCTTAC

TGATGGAAAACTTGATGGTCTTGTTCCTTCTTATGCTGAAAAGAAGCT

AAAATTTCAAGATCACTTGGTGCTTCTGTTTATTGTGTTGGTGTTCTTG

ATTTTGAACAAGCTCAACTTGAAAGAATTGCTGATTCTAAAGAACAAGT

TTTTCCTGTTAAGGGTGGATTTCAAGCTCTTAAAGGAATTATTAATTCT

ATTCTTGCTCAATCTTGTACTGCGGCCGCAGGAGGTGGATCTGGAAATT

CTGACGTCACCGTCCCTTGCCCTGTCCCTTCTACCCCTCCTACCCCTTC

TCCTTCTACCCCTCCTACCCCTTCTCCTTCTTGCTGCCACCCTCGTCTC

TCTCTCCACCGTCCTGCTCTCGAGGACCTCCTCCTCGGTTCTGAGGCTA

ACCTCACCTGCACCCTCACCGGTCTCCGTGACGCTTCTGGTGTCACCTT

CACCTGGACCCCTTCTTCTGGTAAGTCTGCTGTCCAGGGTCCTCCTGAG

CGTGACCTCTGCGGTTGCTACTCTGTCTCTTCTGTCCTCCCTGGTTGCG

CTGAGCCTTGGAACCACGGTAAGACCTTCACCTGCACCGCTGCTTACCC

TGAGTCTAAGACCCCTCTCACCGCTACCCTCTCTAAGTCTGGTAACACC

TTCCGTCCTGAGGTCCACCTCCTCCCTCCTCCTTCTGAGGAGCTCGCTC

TCAACGAGCTCGTCACCCTCACCTGCCTCGCTCGTGGTTTCTCTCCTAA

GGACGTCCTCGTCCGTTGGCTCCAGGGTTCTCAGGAGCTCCCTCGTGAG

AAGTACCTCACCTGGGCTTCTCGTCAGGAGCCTTCTCAGGGTACCACCA

CCTTCGCTGTCACCTCTATCCTCCGTGTCGCTGCTGAGGACTGGAAGAA

GGGTGACACCTTCTCTTGCATGGTCGGTCACGAGGCTCTCCCTCTCGCT

TTCACCCAGAAGACCATCGACCGTCTCGCTGGTAAGCCTACCCACGTCA

ACGTCTCTGTCGTCATGGCTGAGGTCGACGGTACCTGCTACTAAAGATCT
```

PgA1-B3 Expression Cassettes.

A soluble extracellular domain of human CMG2 protein, component A1 as above, fused with human IgM Fc-fragment (component B3), resulting in a component A1-B3 recombinant antitoxin optimized for expression in plants. PgA1-B3 expression cassettes were designed for transient and stable plant transformation and expression.

A 1662 bp nucleic acid sequence of PgA1-3:B3-3 (SEQ ID NO: 20) encoding the PgA1-B3 protein (553 aa) for transient expression vectors is as follows:

(SEQ ID NO: 20)

```
CCATGGAACAACCTTCTTGTCGTCGAGCTTTTGATCTTTATTTTGTTCT

TGATAAATCTGGTTCTGTTGCTAATAATTGGATTGAAATTTATAATTTT

GTTCAACAACTTGCTGAAAGATTTGTTTCTCCTGAAATGAGACTTTCTT

TTATTGTTTTTTCTTCTCAAGCTACTATTATTCTTCCTCTTACTGGTGA

TAGAGGAAAAATTTCTAAAGGACTTGAGGATTTGAAAAGAGTTTCTCCT

GTTGGTGAAACTTATATTCATGAGGGACTTAAACTTGCTAATGAACAAA

TTCAAAAAGCTGGTGGTCTTAAAACTTCTTCTATTATTATTGCTCTTAC

TGATGGAAAACTTGATGGTCTTGTTCCTTCTTATGCTGAAAAAGAAGCT

AAAATTTCAAGATCACTTGGTGCTTCTGTTTATTGTGTTGGTGTTCTTG

ATTTTGAACAAGCTCAACTTGAAAGAATTGCTGATTCTAAAGAACAAGT

TTTTCCTGTTAAGGGTGGATTTCAAGCTCTTAAAGGAATTATTAATTCT

ATTCTTGCTCAATCTTGTACTGCGGCCGCAGGAGGTGGATCTGGAAATT

CTGTCCCTCTCCCTGTCATCGCTGAGCTCCCTCCTAAGGTCTCTGTCTT

CGTCCCTCCTCGTGACGGTTTCTTCGGTAACCCTCGTAAGTCTAAGCTC

ATCTGCCAGGCTACCGGTTTCTCTCCTCGTCAGATCCAGGTCTCTTGGC

TCCGTGAGGGTAAGCAGGTCGGTTCTGGTGTCACCACCGACCAGGTCCA

GGCTGAGGCTAAGGAGTCTGGTCCTACCACCTACAAGGTCACCTCTACC

CTCACCATCAAGGAGTCTGACTGGCTCTCTCAGTCTATGTTCACCTGCC

GTGTCGACCACCGTGGTCTCACCTTCCAGCAGAACGCTTCTTCTATGTG

CGTCCCTGACCAGGACACCGCTATCCGTGTCTTCGCTATCCCTCCTTCT

TTCGCTTCTATCTTCCTCACCAAGTCTACCAAGCTCACCTGCCTCGTCA

CCGACCTCACCACCTACGACTCTGTCACCATCTCTTGGACCCGTCAGAA

CGGTGAGGCTGTCAAGACCCACACCAACATCTCTGAGTCTCACCCTAAC

GCTACCTTCTCTGCTGTCGGTGAGGCTTCTATCTGCGAGGACGACTGGA

ACTCTGGTGAGCGTTTCACCTGCACCGTCACCCACACCGACCTCCCTTC

TCCTCTCAAGCAGACCATCTCTCGTCCTAAGGGTGTCGCTCTCCACCGT

CCTGACGTCTACCTCCTCCCTCCTGCTCGTGAGCAGCTCAACCTCCGTG

AGTCTGCTACCATCACCTGCCTCGTCACCGGTTTCTCTCCTGCTGACGT

CTTCGTCCAGTGGATGCAGCGTGGTCAGCCTCTCTCTCCTGAGAAGTAC

GTCACCTCTGCTCCTATGCCTGAGCCTCAGGCTCCTGGTCGTTACTTCG

CTCACTCTATCCTCACCGTCTCTGAGGAGGAGTGGAACACCGGTGAGAC

CTACACCTGCGTCGTCGCTCACGAGGCTCTCCCTAACCGTGTCACCGAG

CGTACCGTCGACAAGTCTACCGGTAAGCCTACCCTCTACAACGTCTCTC

TCGTCATGTCTGACACCGCTGGTACCTGCTACCCAATAAGAGCTC
```

A 1658 bp nucleic acid sequence of PgA-4:B3-4 (SEQ ID NO: 21) encoding the PgA1-B3 protein (549 aa) for stable transformation vectors is as follows:

(SEQ ID NO: 21)

```
CCATGGAACAACCTTCTTGTCGTCGAGCTTTTGATCTTTATTTTGTTCT

TGATAAATCTGGTTCTGTTGCTAATAATTGGATTGAAATTTATAATTTT

GTTCAACAACTTGCTGAAAGATTTGTTTCTCCTGAAATGAGACTTTCTT

TTATTGTTTTTTCTTCTCAAGCTACTATTATTCTTCCTCTTACTGGTGA

TAGAGGAAAAATTTCTAAAGGACTTGAGGATTTGAAAAGAGTTTCTCCT

GTTGGTGAAACTTATATTCATGAGGGACTTAAACTTGCTAATGAACAAA

TTCAAAAAGCTGGTGGTCTTAAAACTTCTTCTATTATTATTGCTCTTAC

TGATGGAAAACTTGATGGTCTTGTTCCTTCTTATGCTGAAAAAGAAGCT

AAAATTTCAAGATCACTTGGTGCTTCTGTTTATTGTGTTGGTGTTCTTG

ATTTTGAACAAGCTCAACTTGAAAGAATTGCTGATTCTAAAGAACAAGT

TTTTCCTGTTAAGGGTGGATTTCAAGCTCTTAAAGGAATTATTAATTCT

ATTCTTGCTCAATCTTGTACTGCGGCCGCAGGAGGTGGATCTGGAAATT

CTGTCCCTCTCCCTGTCATCGCTGAGCTCCCTCCTAAGGTCTCTGTCTT

CGTCCCTCCTCGTGACGGTTTCTTCGGTAACCCTCGTAAGTCTAAGCTC

ATCTGCCAGGCTACCGGTTTCTCTCCTCGTCAGATCCAGGTCTCTTGGC

TCCGTGAGGGTAAGCAGGTCGGTTCTGGTGTCACCACCGACCAGGTCCA

GGCTGAGGCTAAGGAGTCTGGTCCTACCACCTACAAGGTCACCTCTACC

CTCACCATCAAGGAGTCTGACTGGCTCTCTCAGTCTATGTTCACCTGCC

GTGTCGACCACCGTGGTCTCACCTTCCAGCAGAACGCTTCTTCTATGTG

CGTCCCTGACCAGGACACCGCTATCCGTGTCTTCGCTATCCCTCCTTCT

TTCGCTTCTATCTTCCTCACCAAGTCTACCAAGCTCACCTGCCTCGTCA

CCGACCTCACCACCTACGACTCTGTCACCATCTCTTGGACCCGTCAGAA

CGGTGAGGCTGTCAAGACCCACACCAACATCTCTGAGTCTCACCCTAAC

GCTACCTTCTCTGCTGTCGGTGAGGCTTCTATCTGCGAGGACGACTGGA

ACTCTGGTGAGCGTTTCACCTGCACCGTCACCCACACCGACCTCCCTTC

TCCTCTCAAGCAGACCATCTCTCGTCCTAAGGGTGTCGCTCTCCACCGT

CCTGACGTCTACCTCCTCCCTCCTGCTCGTGAGCAGCTCAACCTCCGTG

AGTCTGCTACCATCACCTGCCTCGTCACCGGTTTCTCTCCTGCTGACGT

CTTCGTCCAGTGGATGCAGCGTGGTCAGCCTCTCTCTCCTGAGAAGTAC

GTCACCTCTGCTCCTATGCCTGAGCCTCAGGCTCCTGGTCGTTACTTCG

CTCACTCTATCCTCACCGTCTCTGAGGAGGAGTGGAACACCGGTGAGAC

CTACACCTGCGTCGTCGCTCACGAGGCTCTCCCTAACCGTGTCACCGAG

CGTACCGTCGACAAGTCTACCGGTAAGCCTACCCTCTACAACGTCTCTC

TCGTCATGTCTGACACCGCTGGTACCTGCTACTAAAGATCT
```

PgB4-A1 Expression Cassettes.

A coat protein VP2 of the human polyoma virus (JC virus) capable of self-assembly into VLPs (component B4) was fused with the soluble extracellular domain of human CMG2 protein, (component A1), resulting in a component B4-A1 recombinant antitoxin. PgB4-A1 expression cassettes were optimized for transient and stable plant transformation and expression.

A 1064 bp nucleic acid sequence of PgB4-2: A1-3 (SEQ ID NO: 22) encoding the PgB4-A1 protein (354 aa) for transient or stable plant transformation/expression vectors is as follows:

```
                                        (SEQ ID NO: 22)
CCATGGGTGCTGCTCTCGCTCTCCTCGGTGACCTCGTCGCTACCGTCT

CTGAGGCTGCTGCTGCTACCGGTTTCTCTGTCGCTGAGATCGCTGCTGG

TGAGGCTGCTGCTACCATCGAGGTCGAGATCGCTTCTCTCGCTACCGTC

GAGGGTATCACCTCTACCTCTGAGGCTATCGCTGCTATCGGTCTCACCC

CTGAGACCTACGCTGTCATCACCGGTGCTCCTGGTGCTGTCGCTGGTTT

CGCTGCTCTCGTCCAGACCGTCACCGGTGGTTCTGCTATCGCTCAGCTC

GGTTACCGTTTCTTCGCTGACTGGGACCACAAGGTCTCTACCGTCGGTC

TCTTCCAGCAGCCTGCTATGGCTCTCCAGCTCTTCAACCCTGAGGACTA

CTACGACATCCTCTTCCCTGGTGTCAACGCTTTCGTCAACAACATCCAC

TACCTCGACCCTCGTCACTGGGGTCCTTCTCTCTTCTCTACCATCTCTC

AGGCTTTCTGGAACCTCGTCCGTGACGACCTCCCTGCTCTCACCTCTCA

GGAGATCCAGCGTCGTACCCAGAAGCTCTTCGTCGAGTCTCTCGCTCGT

TTCCTCGAGGAGACCACCTGGGCTATCGTCAACTCTCCTGCTAACCTCT

ACAACTACATCTCTGACTACTACTCTCGTCTCTCTCCTGTCCGTCCTTC

TATGGTCCGTCAGGTCGCTCAGCGTGAGGGTACCTACATCTCTTTCGGT

CACTCTTACACCCAGTCTATCGACGACGCTGACTCTATCCAGGAGGTCA

CCCAGCGTCTCGACCTCAAGACCCCTAACGTCCAGTCTGGTGAGTTCAT

CGAGCGTTCTATCGCTCCTGGTGGTGCTAACCAGCGTTCTGCTCCTCAG

TGGATGCTCCCTCTCCTCCTCGGTCTCTACGGTACCGTCACCCCTGCTC

TCGAGGCTTACGAGGACGGTCCTAACAAGAAGAAGCGTCGTAAGGAGGG

TCCTCGTGCTTCTTCTAAGACCTCTTACAAGCGTCGTTCTCGTTCTTCT

CGTTCTGGAGGTGGATCTGGAAATTCTGCGGCCGCA
```

PgB5-A1 Expression Cassettes.

*Arabidopsis thaliana* oleosin (OLE) protein is capable of targeting itself, as well as, another covalently fused protein to plant cell oil bodies, thus providing accumulation of the target protein in plant lipid fraction making it easily extractable ("component B5"). OLE protein was used for cloning as a fusion with CMG2 ("component A1"), resulting in "component B5-A1" recombinant antitoxin, and named PgB5-A1. PgB5-A1 constructs were optimized for transient and stable plant transformation/expression.

A 530 bp nucleic acid sequence PgB5-2: A1-3 (SEQ ID NO: 23) encoding the PgB5 protein (176 aa) for cloning as a fusion with the ATR-encoding DNA fragment in transient or stable plant transformation/expression vectors is as follows:

```
                                        (SEQ ID NO: 23)
CCATGGCCGACACGGCCAGGGGCACGCACCACGACATCATCGGCAGG

GACCAGTACCCGATGATGGGCAGGGACAGGGACCAGTACCAGATGTCCG

GCAGGGGCTCCGACTACTCCAAGTCCAGGCAGATCGCCAAGGCCGCCAC

GGCCGTGACGGCCGGCGGCTCCCTCCTCGTGCTCTCCTCCCTCACGCTC
```

```
-continued
GTGGGCACGGTGATCGCCCTCACGGTGGCCACGCCGCTCCTCGTGATCT

TCTCCCCGATCCTCGTGCCGGCCCTCATCACGGTGGCCCTCCTCATCAC

GGGCTTCCTCTCCTCCGGCGGCTTCGGCATCGCCGCCATCACGGTGTTC

TCCTGGATCTACAAGTACGCCACGGGCGAGCACCCGCAGGGCTCCGACA

AGCTCGACTCCGCCAGGATGAAGCTCGGCTCCAAGGCCCAGGACCTCAA

GGACAGGGCCCAGTACTACGGCCAGCAGCACACGGGCGGCGAGCACGAC

AGGGACAGGACGAGGGGCGGCCAGCACACGACGGCGGCCGCA
```

PgA2 Expression Cassettes.

PA-binding domain of LF (LFn, amino acids 28-263) of the *B. anthracis* three-component anthrax toxin (component A2), capable of binding the PA region was optimized for expression in plants. PgA2 designs for transient and stable plant transformation/expression are shown as follows.

A 722 bp nucleic acid sequence of PgA2-1 (SEQ ID NO: 3) encoding the PgA2 protein (237 aa) for cloning in transient expression vector is as follows:

```
                                        (SEQ ID NO: 3)
CCATGGGTGACGTCGGTATGCACGTCAAGGAGAAGGAGAAGAACAAGG

ACGAGAACAAGCGTAAGGACGAGGAGCGTAACAAGACCCAGGAGGAGC

ACCTCAAGGAGATCATGAAGCACATCGTCAAGATCGAGGTCAAGGGTGA

GGAGGCTGTCAAGAAGGAGGCTGCTGAGAAGCTCCTCGAGAAGGTCCCT

TCTGACGTCCTCGAGATGTACAAGGCTATCGGTGGTAAGATCTACATCG

TCGACGGTGACATCACCAAGCACATCTCTCTCGAGGCTCTCTCTGAGGA

CAAGAAGAAGATCAAGGACATCTACGGTAAGGACGCTCTCCTCCACGAG

CACTACGTCTACGCTAAGGAGGGTTACGAGCCTGTCCTCGTCATCCAGT

CTTCTGAGGACTACGTCGAGAACACCGAGAAGGCTCTCAACGTCTACTA

CGAGATCGGTAAGATCCTCTCTCGTGACATCCTCTCTAAGATCAACCAG

CCTTACCAGAAGTTCCTCGACGTCCTCAACACCATCAAGAACGCTTCTG

ACTCTGACGGTCAGGACCTCCTCTTCACCAACCAGCTCAAGGAGCACCC

TACCGACTTCTCTGTCGAGTTCCTCGAGCAGAACTCTAACGAGGTCCAG

GAGGTCTTCGCTAAGGCTTTCGCTTACTACATCGAGCCTCAGCACCGTG

ACGTCCTCCAGCTCTACGCTCCTGAGGCTTAAGAGCTC
```

A 728 bp nucleic acid sequence of PgA2-2 (SEQ ID NO: 4) encoding the PgA2 protein (241 aa) for stable plant transformation vectors is as follows:

```
                                        (SEQ ID NO: 4)
CCATGGGTGACGTCGGTATGCACGTCAAGGAGAAGGAGAAGAACAAGG

ACGAGAACAAGCGTAAGGACGAGGAGCGTAACAAGACCCAGGAGGAGC

ACCTCAAGGAGATCATGAAGCACATCGTCAAGATCGAGGTCAAGGGTGA

GGAGGCTGTCAAGAAGGAGGCTGCTGAGAAGCTCCTCGAGAAGGTCCCT

TCTGACGTCCTCGAGATGTACAAGGCTATCGGTGGTAAGATCTACATCG

TCGACGGTGACATCACCAAGCACATCTCTCTCGAGGCTCTCTCTGAGGA

CAAGAAGAAGATCAAGGACATCTACGGTAAGGACGCTCTCCTCCACGAG

CACTACGTCTACGCTAAGGAGGGTTACGAGCCTGTCCTCGTCATCCAGT
```

-continued

```
CTTCTGAGGACTACGTCGAGAACACCGAGAAGGCTCTCAACGTCTACTA

CGAGATCGGTAAGATCCTCTCTCGTGACATCCTCTCTAAGATCAACCAG

CCTTACCAGAAGTTCCTCGACGTCCTCAACACCATCAAGAACGCTTCTG

ACTCTGACGGTCAGGACCTCCTCTTCACCAACCAGCTCAAGGAGCACCC

TACCGACTTCTCTGTCGAGTTCCTCGAGCAGAACTCTAACGAGGTCCAG

GAGGTCTTCGCTAAGGCTTTCGCTTACTACATCGAGCCTCAGCACCGTG

ACGTCCTCCAGCTCTACGCTCCTGAGGCTGGAGATCTCCAATAA
```

PgA2-B1 Expression Cassettes.

PA-binding domain of LF (LF, amino acids 28-263) of the B. anthracis three-component anthrax toxin (component A2), capable of binding the PA region was optimized for expression in plants as fusion with human IgG1 Fc-fragment (component B1), resulting in a component A2-B1 recombinant antitoxin. PgA2-B1 designs for transient and stable plant transformation/expression are shown as follows.

A 721 bp nucleic acid sequence encoding PgA2-4: B1-3 (SEQ ID NO: 37) the PgA2 protein (239 aa) for cloning as a fusion with the Fc-encoding DNA fragment in the transient (as in SEQ ID NO: 16) or stable transformation/expression vectors (as in SEQ ID NO: 17):

```
                                    (SEQ ID NO: 37)
CCATGGGTGACGTCGGTATGCACGTCAAGGAGAAGGAGAAGAACAAGG

ACGAGAACAAGCGTAAGGACGAGGAGCGTAACAAGACCCAGGAGGAGC

ACCTCAAGGAGATCATGAAGCACATCGTCAAGATCGAGGTCAAGGGTGA

GGAGGCTGTCAAGAAGGAGGCTGCTGAGAAGCTCCTCGAGAAGGTCCCT

TCTGACGTCCTCGAGATGTACAAGGCTATCGGTGGTAAGATCTACATCG

TCGACGGTGACATCACCAAGCACATCTCTCTCGAGGCTCTCTCTGAGGA

CAAGAAGAAGATCAAGGACATCTACGGTAAGGACGCTCTCCTCCACGAG

CACTACGTCTACGCTAAGGAGGGTTACGAGCCTGTCCTCGTCATCCAGT

CTTCTGAGGACTACGTCGAGAACACCGAGAAGGCTCTCAACGTCTACTA

CGAGATCGGTAAGATCCTCTCTCGTGACATCCTCTCTAAGATCAACCAG

CCTTACCAGAAGTTCCTCGACGTCCTCAACACCATCAAGAACGCTTCTG

ACTCTGACGGTCAGGACCTCCTCTTCACCAACCAGCTCAAGGAGCACCC

TACCGACTTCTCTGTCGAGTTCCTCGAGCAGAACTCTAACGAGGTCCAG

GAGGTCTTCGCTAAGGCTTTCGCTTACTACATCGAGCCTCAGCACCGTG

ACGTCCTCCAGCTCTACGCTCCTGAGGCTGCGGCCGC
```

Helper Element (Component C)/PgC1 Expression Cassettes.

Human immunoglobulin J polypeptide, linker protein for immunoglobulin Alpha and Mu polypeptides (IgJ, amino acids 34-159) (component C1), that has no native signal peptide (amino acids 1-33), was optimized for expression in plants. IgJ is capable of helping IgA and/or IgM subunits to self-assemble into quaternary structure. PgC1 cassettes were designed for transient and stable plant transformation/expression.

A 395 bp nucleic acid sequence of PgC1-2 (SEQ ID NO: 32) encoding the PgC1 protein (128 aa) for transient expression vectors is as follows:

```
                                    (SEQ ID NO: 32)
CCATGGGAAAGTGCAAGTGCGCTCGTATCACCTCTCGTATCATCCGTTC

TTCTGAGGACCCTAACGAGGACATCGTCGAGCGTAACATCCGTATCATC

GTCCCTCTCAACAACCGTGAGAACATCTCTGACCCTACCTCTCCTCTCC

GTACCCGTTTCGTCTACCACCTCTCTGACCTCTGCAAGAAGTGCGACCC

TACCGAGGTCGAGCTCGACAACCAGATCGTCACCGCTACCCAGTCTAAC

ATCTGCGACGAGGACTCTGCTACCGAGACCTGCTACACCTACGACCGTA

ACAAGTGCTACACCGCTGTCGTCCCTCTCGTCTACGGTGGTGAGACCA

AGATGGTCGAGACCGCTCTCACCCCTGACGCTTGCTACCCTGACTAAGA

GCTC
```

A 401 bp nucleic acid sequence of PgC1-3 (SEQ ID NO: 33) encoding the PgC1$_{Nt}$ protein (132 aa) for stable transformation vectors is as follows:

```
                                    (SEQ ID NO: 33)
CCATGGGAAAGTGCAAGTGCGCTCGTATCACCTCTCGTATCATCCGTTC

TTCTGAGGACCCTAACGAGGACATCGTCGAGCGTAACATCCGTATCATC

GTCCCTCTCAACAACCGTGAGAACATCTCTGACCCTACCTCTCCTCTCC

GTACCCGTTTCGTCTACCACCTCTCTGACCTCTGCAAGAAGTGCGACCC

TACCGAGGTCGAGCTCGACAACCAGATCGTCACCGCTACCCAGTCTAAC

ATCTGCGACGAGGACTCTGCTACCGAGACCTGCTACACCTACGACCGTA

ACAAGTGCTACACCGCTGTCGTCCCTCTCGTCTACGGTGGTGAGACCAA

GATGGTCGAGACCGCTCTCACCCCTGACGCTTGCTACCCTGACGCAGAT

CTCCAATAA
```

VLP Helper Element/PgC2 Expression Cassettes.

A coat protein VP1 of human polyoma virus capable of self-assembling into VLPs and necessary for the inclusion of JC virus VP2 protein into the same VLP assembly ("component C2"), resulting in a component C2, was optimized for expression in plants. PgC2 design for Magnification and stable plant transformation is shown as follows.

A 1133 bp nucleic acid PgC2-2 (SEQ ID NO: 34) encoding the PgC2 protein (374 aa) for cloning in MagnICON expression vector or in pIV1.2/pIV1.3 Impact Vectors (Plant Research International, Wageningen, The Netherlands):

```
                                    (SEQ ID NO: 34)
CCATGGCCCCAACAAAGAGAAAAGGAGAAAGGAAGGACCCAGTGCAAGT

TCCAAAACTTCTCATAAGAGGAGGAGTAGAAGTTCTTGAAGTTAAAACT

GGAGTTGACTCAATTACAGAGGTAGAATGCTTCTTAACTCCAGAAATGG

GTGACCCAGATGAGCATCTTAGGGGTTTTAGTAAGTCAATATCTATATC

AGATACATTTGAAAGTGACTCCCCAAATAGGGACATGCTTCCTTGTTAC

AGTGTGGCCAGGATTCCACTACCTAATCTAAATGAGGATCTAACTTGTG

GAAATATACTCATGTGGGAGGCTGTGACATTAAAGACTGAGGTTATAGG

AGTGACAAGTTTGATGAATGTGCATTCTAATGGTCAAGCAACTCATGAC

AATGGTGCAGGTAAGCCAGTGCAGGGTACAAGTTTTCATTTCTTTTCTG

TTGGAGGTGAGGCTTTAGAATTACAGGGAGTGCTTTTTAATTACAGAAC
```

```
AAAGTACCCAGATGGAACAATTTTTCCAAAGAATGCCACAGTGCAATCT

CAAGTCATGAACACAGAGCATAAGGCGTACCTAGATAAGAACAAAGCAT

ATCCTGTTGAATGTTGGGTTCCTGATCCAACTAGAAATGAAAACACAAG

ATATTTTGGTACACTAACAGGAGGAGAAAATGTTCCTCCAGTTCTTCAT

ATAACAAACACTGCCACAACAGTGTTGCTTGATGAATTTGGTGTTGGAC

CACTTTGTAAAGGTGACAACTTATACTTGTCAGCTGTTGATGTCTGTGG

TATGTTTACAAACAGGTCTGGTTCCCAGCAGTGGAGAGGACTCTCCAGA

TATTTTAAGGTGCAGCTAAGGAAGAGGAGGGTTAAGAACCCATACCCAA

TTTCTTTCCTTCTTACTGATTTGATTAACAGAAGGACTCCTAGAGTTGA

TGGACAGCCTATGTATGGTATGGATGCTCAAGTAGAGGAGGTTAGAGTT

TTTGAGGGAACAGAGGAGCTTCCAGGAGACCCAGACATGATGAGATACG

TTGACAAATATGGACAGTTGCAGACAAAGATGCTGGCGGCCGCAGATCT

CCAAAAGCTTATTAGCGAGGAGGATCTTCATCACCATCACCATCACTAA

GAGCTC
```

PgB1, PgB2, and PgB2 Expression Cassettes.

Human IgG1, IgA1, and IgM Fc-fragment (components B1, B2, and B3) polypeptides were used as carrier proteins. B1, B2 and B3 constructs were optimized for transient and stable plant transformation/expression.

A 687 bp nucleic acid sequence of PgB1-1 (SEQ ID NO: 6) encoding the PgB1 polypeptide (229 aa) for cloning as a fusion with A1 or A2 Component in transient or stable plant transformation/expression vectors is as follows:

(SEQ ID NO: 6)

GATAAAACTCATACTTGTCCTCCTTGTCCTGCTCCTGAACTTCTTGGTG

GTCCTTCTGTTTTTCTTTTTCCTCCTAAACCTAAAGATACTCTTATGAT

TTCTCGTACTCCTGAAGTTACTTGTGTTGTTGTTGATGTTTCTCATGAA

GATCCTGAAGTTAAATTTAATTGGTATGTTGATGGTGTTGAAGTTCATA

ATGCTAAAACTAAACCTCGTGAAGAACAATATAATTCTACTTATCGTGT

TGTTTCTGTTCTTACTGTTCTTCATCAAGATTGGCTTAATGGTAAAGAA

TATAAATGTAAAGTTTCTAATAAAGCTCTTCCTGCTCCTATTGAAAAAA

CTATTTCTAAAGCTAAAGGTCAACCTCGTGAACCTCAAGTTTATACTCT

TCCTCCTTCTCGTGAAGAAATGACTAAAAATCAAGTTTCTCTTACTTGT

CTTGTTAAAGGTTTTTATCCTTCTGATATTGCTGTTGAATGGGAATCTA

ATGGTCAACCTGAAAATAATTATAAAACTACTCCTCCTGTTCTTGATTC

TGATGGTTCTTTTTTTCTTTATTCTAAACTTACTGTTGATAAATCTCGT

TGGCAACAAGGTAATGTTTTTTCTTGTTCTGTTATGCATGAAGCTCTTC

ATAATCATTATACTCAAAAATCTCTTTCTCTTTCTCCTGGTAAAGATCTT

A 774 bp nucleic acid sequence of PgB2-1 (SEQ ID NO: 7) encoding the PgB2 polypeptide (258 aa) for cloning as a fusion with A1 or A2 Component in transient or stable plant transformation/expression vectors is as follows:

(SEQ ID NO: 7)

GATGTTACTGTTCCTTGTCCTGTTCCTTCTACTCCTCCTACTCCTTCTC

CTTCTACTCCTCCTACTCCTTCTCCTTCTTGTTGTCATCCTCGTCTTTC

TCTTCATCGTCCTGCTCTTGAAGATCTTCTTCTTGGTTCTGAAGCTAA

TCTTACTTGTACTCTTACTGGTCTTCGTGATGCTTCTGGTGTTACTTTT

ACTTGGACTCCTTCTTCTGGTAAATCTGCTGTTCAAGGTCCTCCTGAAC

GTGATCTTTGTGGTTGTTATTCTGTTTCTTCTGTTCTTCCTGGTTGTGC

TGAACCTTGGAATCATGGTAAAACTTTTACTTGTACTGCTGCTTATCCT

GAATCTAAAACTCCTCTTACTGCTACTCTTTCTAAATCTGGTAATACTT

TTCGTCCTGAAGTTCATCTTCTTCCTCCTCCTTCTGAAGAACTTGCTCT

TAATGAACTTGTTACTCTTACTTGTCTTGCTCGTGGTTTTTCTCCTAAA

GATGTTCTTGTTCGTTGGCTTCAAGGTTCTCAAGAACTTCCTCGTGAAA

AATATCTTACTTGGGCTTCTCGTCAAGAACCTTCTCAAGGTACTACTAC

TTTTGCTGTTACTTCTATTCTTCGTGTTGCTGCTGAAGATTGGAAAAAA

GGTGATACTTTTTCTTGTATGGTTGGTCATGAAGCTCTTCCTCTTGCTT

TTACTCAAAAAACTATTGATCGTCTTGCTGGTAAACCTACTCATGTTAA

TGTTTCTGTTGTTATGGCTGAAGTTGATGGTACTTGTTAT

A 1059 bp nucleic acid sequence of PgB3-1 (SEQ ID NO: 8) encoding the PgB3 polypeptide (353 aa) for cloning as a fusion with A1 or A2 Component in transient or stable plant transformation/expression vectors is as follows:

(SEQ ID NO: 8)

GTTCCTCTTCCTGTTATTGCTGAACTTCCTCCTAAAGTTTCTGTTTTTG

TTCCTCCTCGTGATGGTTTTTTTGGTAATCCTCGTAAATCTAAACTTAT

TTGTCAAGCTACTGGTTTTTCTCCTCGTCAAATTCAAGTTTCTTGGCTT

CGTGAAGGTAAACAAGTTGGTTCTGGTGTTACTACTGATCAAGTTCAAG

CTGAAGCTAAAGAATCTGGTCCTACTACTTATAAAGTTACTTCTACTCT

TACTATTAAAGAATCTGATTGGCTTTCTCAATCTATGTTTACTTGTCGT

GTTGATCATCGTGGTCTTACTTTTCAACAAAATGCTTCTTCTATGTGTG

TTCCTGATCAAGATACTGCTATTCGTGTTTTTGCTATTCCTCCTTCTTT

TGCTTCTATTTTTCTTACTAAATCTACTAAACTTACTTGTCTTGTTACT

GATCTTACTACTTATGATTCTGTTACTATTTCTTGGACTCGTCAAAATG

GTGAAGCTGTTAAAACTCATACTAATATTTCTGGATGATTGGAATTCTG

GTGAACGTTTTACTTGTACTGTTACTCATACTGATCTTCCTTCTCCTCT

TAAACAAACTATTTCTCGTCCTAAAGGTGTTGCTCTTCATCGTCCTGAT

GTTTATCTTCTTCCTCCTGCTCGTGAACAACTTAATCTTCGTGAATCTG

CTACTATTACTTGTCTTGTTACTGGTTTTTCTCCTGCTGATGTTTTTGT

TCAATGGATGCAACGTGGTCAACCTCTTTCTCCTGAAAAATATGTTACT

TCTGCTCCTATGCCTGAACCTCAAGCTCCTGGTCGTTATTTTGCTCATT

CTATTCTTACTGTTTCTGAAGAAGAATGGAATACTGGTGAAACTTATAC

TTGTGTTGTTGCTCATGAAGCTCTTCCTAATCGTGTTACTGAACGTACT

-continued

GTTGATAAATCTACTGGTAAACCTACTCTTTATAATGTTTCTCTTGTTA

TGTCTGATACTGCTGGTACTTGTTAT

Table 2 lists and describes all sequences included herein.

| SEQ NAME | DESCRIPTION | SEQ ID NO |
|---|---|---|
| PgA1-1 construct | Extracellular domain of human CMG2 for transient expression (DNA) | 1 |
| PgA1-2 construct | Extracellular domain of human CMG2 for stable transformation (DNA) | 2 |
| PgA2-1 construct | PA-binding domain of Lethal factor LF for transient expression (DNA) | 3 |
| PgA2-2 construct | PA-binding domain of Lethal factor LF for stable transformation(DNA) | 4 |
| A2-3-PA-LF construct | Native PA-binding domain LF of *B. anthracis* lethal factor LF (DNA) Accession No: M29081.1 | 5 |
| PgB1-1 construct | Human Fc-IgG1 fragment optimized for medicinal plant (DNA) | 6 |
| PgB2-1 construct | Human Fc-IgA1 fragment optimized for medicinal plant (DNA) | 7 |
| PgB3-1 construct | Human Fc-IgM fragment optimized for medicinal plant (DNA) | 8 |
| PgB1-2 construct | Native Fc-IgG fragment (DNA) | 9 |
| PgB2-2 construct | Native Fc-IgA fragment (DNA) | 10 |
| PgB3-2 construct | Native Fc-IgM fragment (DNA) | 11 |
| PgB4-1 construct | Native VP2 coat protein of JC virus (DNA) | 12 |
| PgB5-construct | Native *A. thaliana* oleosin (DNA) | 13 |
| PgC1-1-construct | Native IgJ gene | 14 |
| C2-1-construct | Native VP1 coat protein of JC virus (DNA) | 15 |
| PgA1-3:B1-3 construct | sCMG2-IgG1(Fc) for transient expression (DNA) | 16 |
| PgA1-4:B1-4 construct | CMG2-IgG1(Fc) for stable transformation (DNA) | 17 |
| PgA1-3:B2-3 construct | sCMG2-IgA1 (Fc) for transient expression (DNA) | 18 |
| PgA1-4:B2-4 construct | sCMG2-IgA1 (Fc) for stable transformation (DNA) | 19 |
| PgA1-3:B3-3 construct | CMG2-IgM1 (Fc) for transient expression (DNA) | 20 |
| PgA1-4:B3-4 construct | sCMG2-IgM1 (Fc) for stable transformation (DNA) | 21 |
| PgA1-3:B4-2 construct | VP2 polyoma (JCvirus)-sCMG2 (DNA) | 22 |
| PgA1-3:B5-2 | *A. thaliana* oleosin (OLE)-sCMG2 (DNA) | 23 |
| A1-CMG2 protein | Native example of human CMG2 protein | 24 |
| A2-protein-PA-binding LF protein | Native example og PA binding domain of *B. anthracis* lethal factor LF protein | 25 |
| B1-protein | Native Fc-IgG protein Accession No. AY172957 | 26 |
| B2-protein | Native Fc-IgA protein Accession No. S71043 | 27 |
| B3-protein | Native Fc-IgM protein Accession No. X67301 S50847 | 28 |
| B4-protein | Native VP2 coat protein of JC virus Accession No. NC_001699 | 29 |
| B5-protein | Native *A. thaliana* oleosin Accession No. X62353 S38026 | 30 |
| PgA1-1:B1-1 protein | Amino acid sequence PgA1B1 | 31 |
| C1-2 construct | Human IgJ polypeptide (linker for IGgs Alpha and Mu) for transient expression | 32 |
| C1-3 construct | Human IgJ polypeptide (linker for Igs Alpha and Mu) for stable transformation (DNA) | 33 |
| C2-2 construct | A coat protein of human polyoma virus | 34 |
| C1-protein | IgJ protein Accession No. NM_144646 | 35 |
| C2-protein | VP1 coat protein of JC virus Accession No. NC_001699 | 36 |
| PgA2-4:B1-3 construct | PA-binding domain of lethal factor-Fc-IgG1 (DNA) | 37 |
| PgA1-5:B1-5 construct | sCMG2-hIgG1(Fc) gene optimized for expression in plants (DNA) | 38 |
| Kozak-like sequence | Regulatory element (DNA) | 39 |
| BGLII and SACI sites | Restriction sites | 40 |
| NOTI site | Restriction site | 41 |
| BAA targeting peptide | Targeting peptide | 42 |
| ABP1 targeting peptide | Targeting peptide | 43 |
| Flexible linker | Linker | 44 |
| Trombin cleavage peptide | Cleavage peptide | 45 |
| Factor Faa protease cleavage peptide | Cleavage peptide | 46 |
| PgA1-3 construct | Extracellular domain of human CMG2 (DNA) | 47 |
| PgB1-3 construct | Human Fc-IgG1 fragment (DNA) | 48 |
| PgA1-4 construct | Extracellular domain of human CMG2 (DNA) | 49 |
| PgB1-4 construct | Human Fc-IgG1 fragment (DNA) | 50 |

-continued

| SEQ NAME | DESCRIPTION | SEQ ID NO |
|---|---|---|
| PgB2-3 construct | Human Fc-IgA1 fragment (DNA) | 51 |
| PgB2-4 construct | Human Fc-IgA1 fragment (DNA) | 52 |
| PgB3-3 construct | Fc-IgM fragment (DNA) | 53 |
| PgB3-4 construct | Fc-IgM fragment (DNA) | 54 |
| PgB4-2 construct | VP2 coat protein of JC virus (DNA | 55 |
| PgB5-2 construct | A. thaliana oleosin (DNA) | 56 |
| PgA2-4 construct | Human Fc-IgA1 fragment (DNA) | 57 |
| PgA1-5 construct | Extracellular domain of human CMG2 (DNA) | 58 |
| PgB1-5 construct | Human Fc-IgG1 fragment DNA | 59 |
| PgA1-5 protein | Extracellular domain of human CMG2 protein | 60 |
| PgB1-5 protein | Human Fc-IgG1 fragment protein | 61 |
| NPTII forward primer | PCR primer | 62 |
| NPTII reverse primer | PCR primer | 63 |

Figure 3A:
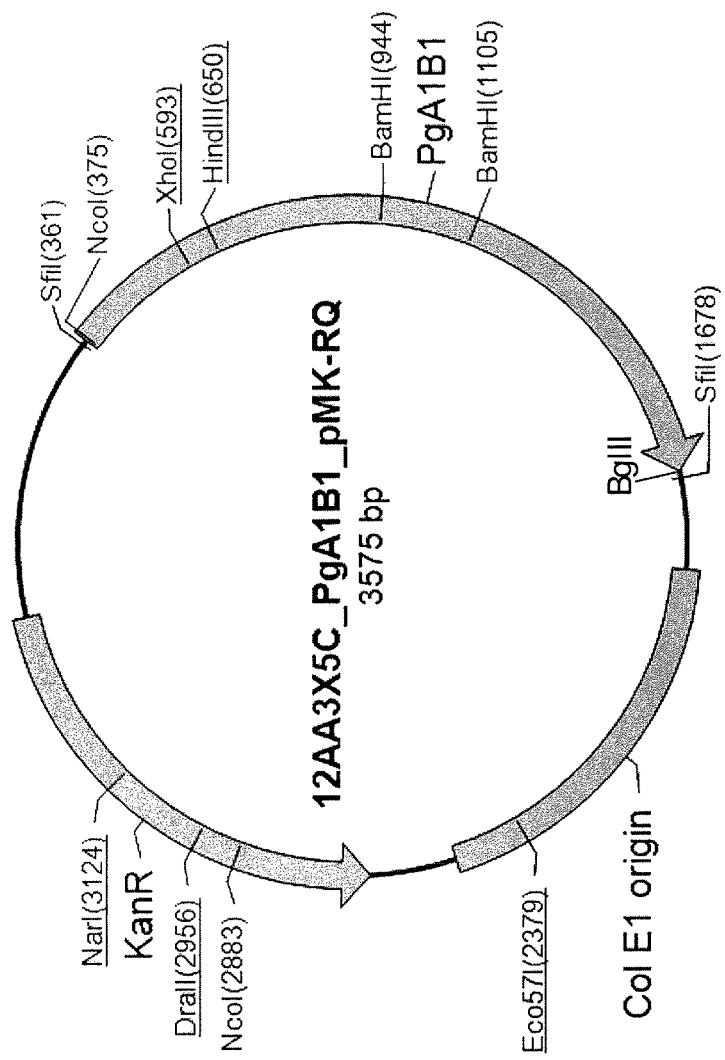
FIG. 3A illustrates a map of an intermediate plasmid that contains a nucleotide sequence encoding a synthetic gene PgA1B1.

Example 2. Construction of the Expression Cassette for Production of Recombinant ATR-FC Fusion Proteins in Plants A synthetic gene encoding PgA1B1 (SEQ ID NO: 38) was assembled from synthetic nucleotides and/or PCR products. The fragment was cloned into the pMK-RQ (KanR) plasmid using SfiI and SfiI cloning sites and resulted in a plasmid 12AA3X5C_PgA1B1_pMK-RQ (FIG. 3A). The plasmid includes an origin of replication Col E1, the restriction sites NarI, DraII, NcoI, Eco57I, and SfiI in the body of vector pMK-RQ, and the restriction sites NcoI, XhoI, HindIII, and BamHI in the 1297 bp synthetic PgA1B1 gene (SEQ ID NO: 39). The plasmid DNA was purified from transformed bacteria and concentration determined with UV spectroscopy. The final construct was verified by sequencing. The sequence congruence within the used restriction sites was 100%.

Figure 3B:
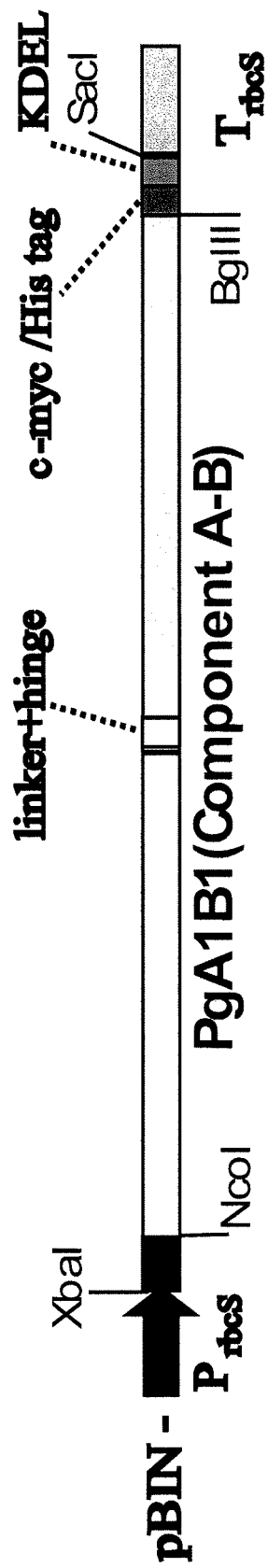
FIG. 3B illustrates a schematic drawing of an expression cassette included in the pBIN vector.

The sequence encoding PgA1B1 (SEQ ID NO: 38) was then cloned into an expression cassette using NcoI and BglII cloning sites. The expression cassette also included nucleic acid sequence encoding the human IgG1 Fc fragment, $P_{rbcS}$ promoter and $T_{rbcS}$ termination signals (FIG. 3B). The expression cassette also included the restriction sites XbaI, NcoI, BglII, and SacI for cloning of the expression cassette into the plant vector. The expression cassette includes PgA1B1, a synthetic nucleotide sequence encoding a soluble recombinant protein (component A1-B1) capable of binding an anthrax toxin PA protein. The recombinant protein includes ATR, which is covalently linked to the Fc fragment of an immunoglobulin G (Fc-IgG) using a short flexible polypeptide linker or hinge. The expression cassette also includes c-myc and His, peptide tags for easy purification of the recombinant protein. The cassette includes the KDEL (SEQ ID NO: 65) short signal peptide directing the expressed recombinant protein to a specific compartment of a plant cell. The expression cassette was than cloned into the pBI121 binary vector (based on the pBIN19 vector) using XbaI and SacI cloning sites (Bevan, M. 1984, Nucl Acids Res 12: 8711-8721).

Figure 4A:
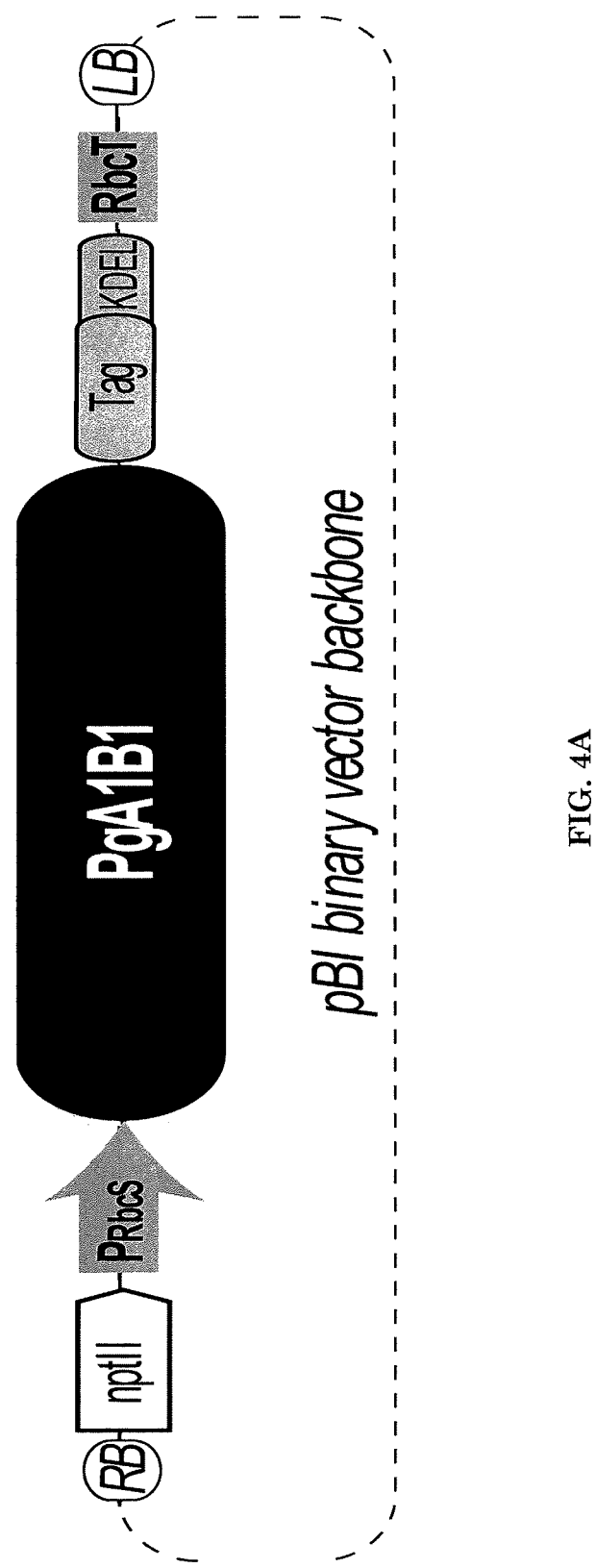
FIGS. 4A-4B illustrate a pBI binary vector that including the TBL-Fc expression cassette (FIG. 4A) and steps for production of the recombinant TBL protein in plants (FIG. 4B).
Figure 4B:
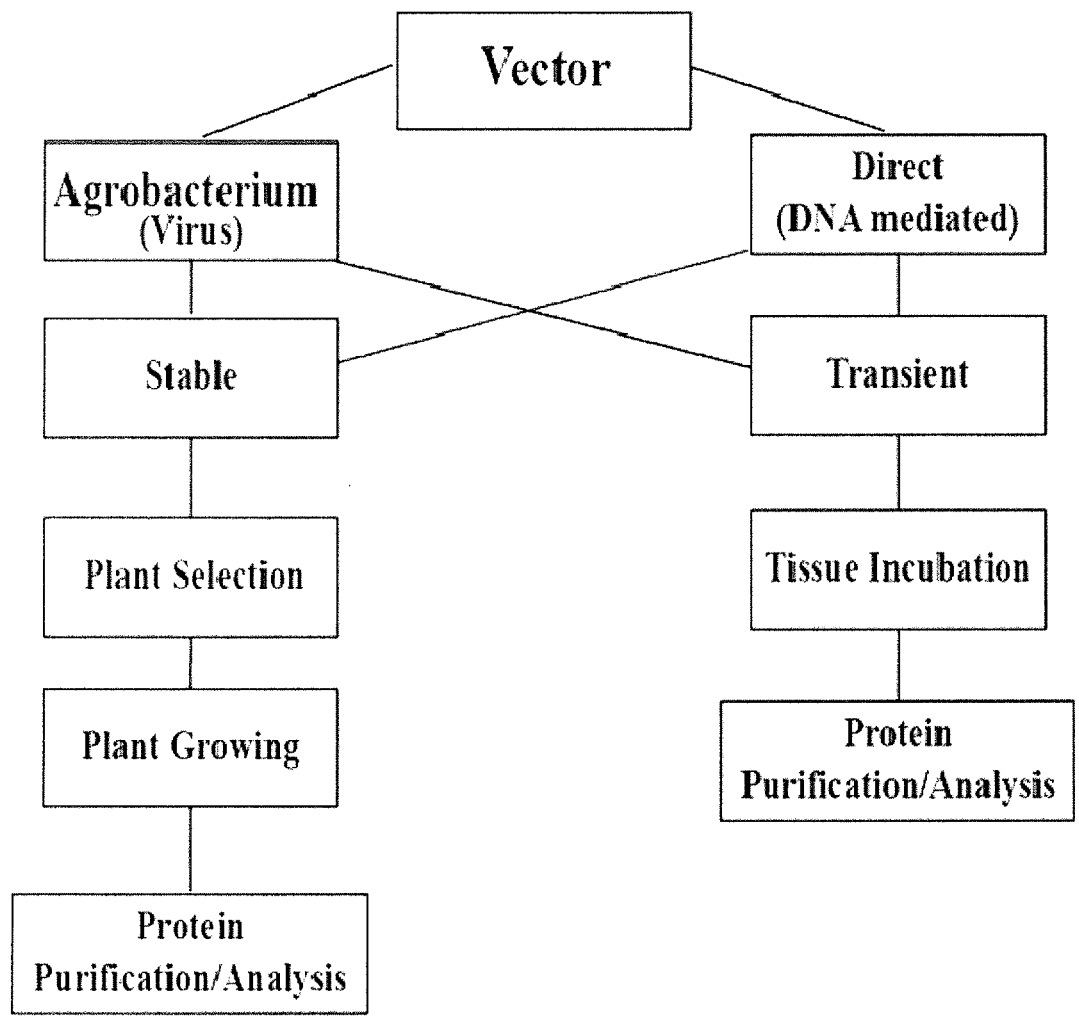

FIG. 4A schematically shows a plant expression vector. As shown, the vector includes a backbone derived from a conventional pBI binary vector covalently linked to the T-DNA surrounded by the right border, RB, and the left border, LB. The T-DNA includes the nptII gene for kanamycin selection. The nptII gene is linked to the expression cassette that includes the Rubisco promoter, $P_{rbcS}$; the recombinant protein PgA1B1; the purification tag, Tag; the endoplasmic reticulum compartment sorting signal, KDEL (SEQ ID NO: 65); and the translation termination signal of the Rubisco gene, RbcT. FIG. 4B is a diagram illustrating ways of using vectors for production of PgA1B1 recombinant proteins in plant. DNA of the expression vectors can be introduced into plant cells either by using Agrobacterium, or by direct DNA transfer. This figure shows that the plant expression vector can be used for stable or transient transformation of plants. In the transient system, plant expression vectors are not integrated into the genomes of the transformed plants. In this system, the recombinant proteins can be produced after a short period of tissue incubation with the vectors. In the stable transformation system, only plant cells with the T-DNAs of the expression vectors integrated into the plant genomes are selected. Such transgenic plants can transfer the T-DNAs to the progeny which may also produce the recombinant proteins.

Example 3. Plants Transformation

Stable Transformation of Tobacco Plants

Figure 5A:
FIGS. 5A-5F illustrate in vitro selection of transgenic tobacco plants engineered to express a recombinant TBL protein.
Figure 5B:
Figure 5C:
Figure 5D:

Stable transformation of tobacco was performed as described in Golovkin et al., 2007, which is incorporated herein by reference in entirety. Tobacco (Nicotiana tabacum cv Wisconsin 38) were used for all experiments. Tobacco seeds were surface sterilized and incubated on the solidified with 0.7% agar Murashige-Skoog medium (Physiol. Plant, 1962, 15:473) supplemented with 1% sucrose, pH 5.8 at 24° C., with 16/8 h light/dark photoperiod. 2-3 weeks old seedlings were excised and transferred to flasks containing the MS medium supplemented with 0.7% agar and 3% sucrose. Sterile leaf explants were transformed by using the described above kanamycin-resistant construct encoding recombinant ATR-Fc protein in the Agrobacterium tumefaciens strain LB4404. Leaves of 5-6 week-old aseptically grown plants were cut into segments 0.5 to 0.7 cm in size and inoculated for 10 minutes with the Agrobacterium cell suspension diluted to $OD_{600\,nm}$ 0.5. Inoculated leaf explants were blotted dry and plated onto Petri dishes with solidified MS medium supplemented with 3% sucrose and 0.7% agar. After 2 days of co-cultivation at 24° C. in the dark, plant explants were transferred to the selection/regeneration MS medium supplemented with 3% sucrose, 1 mg/l BAP, 0.1 mg/l NAA, 100 mg/l kanamycin, 300 mg/l timentin, 0.7% agar and incubated at 24° C. and 16/8 h light/dark photoperiod. After 5-6 weeks of selection, the putative transgenic green shoots were formed (FIGS. 5A-5B). These shoots were excised and transferred to Magenta boxes containing MS medium supplemented with 100 mg/l kanamycin, 3% sucrose, 0.7% agar and 200 mg/l timentin for rooting, FIG. 5C, where transgenic shoots were developing on the medium supplemented with kanamycin. Control wild type tobacco plants failed to grow under similar conditions (FIG. 5A). Plants that rooted in the presence of 100 mg/l kanamycin were tested for expression of recombinant products. The best transgenic lines were chosen for root induction and then were transferred to soil to mature and set seeds (FIG. 5D). Plants were grown in 10-15 cm pot in the greenhouse at 25° C. and 16/8 day/night period.

Figure 5E:

Selected transgenic lines were screened by a PCR reaction for the T-DNA integration based on the detection of the nptII marker encoding resistance to kanamycin (FIG. 4A) linked to recombinant PgA1B1 gene. The nptII-specific primers were as follows: 5-' TGAATGAACTGCAGGACGA-3' (forward; SEQ ID NO: 62) and 5'-AGCCAACGTATGTCCT-GAT-3' (reverse; SEQ ID NO:63). The PCR reaction condition included 30 cycles of polymerization at the annealing temperature 56° C. using Taq polymerase protocol from Promega. As shown on FIG. 5E, over 50% tested plants were positive as they produced PCR products of expected molecular size of approximately 500 bp.

Figure 5F:
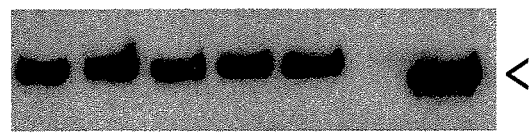

Transgenic plants were further screened with Western blotting for the presence of the ATR-Fc protein fused with the c-myc tag (FIG. 3B). A total crude protein extracts of selected tobacco lines were separated on SDS-PACE and tested by Western blot analysis using the c-myc monoclonal antibody mAb (ATCC, Manassas) and the goat anti-mouse horse radish conjugated antibody (Ab) (Upstate NY) (FIG. 5F). As shown on FIG. 5F, the recombinant product of the expected size of approximately 50 kDa was detected as a single band in all but one tested samples containing a total soluble protein (TSP). The correct molecular weights were verified by pre-stained Universal Kaleidoscope protein marker (BioRad).

Transformation of Echinacea Plants

Plant Material.

Seeds of Echinacea plants were obtained from Horizon Herbs Co. (Williams, Oreg.). Seeds were sterilized with 70% ethanol for 1 min and 25% commercial bleach solution for 10 min. After washing with sterile distilled water, seeds were placed in the germination MS medium containing 10 g/L sucrose and 8 g/L agar. Efficient germination and in vitro culturing was carried out at 24° C. at 16 h-light/8 h-dark photoperiods and 40 µE/m2/S1 light intensity. Cotyledons and young leaves were used for transformation experiments.

Transformation.

Agrobacterium tumefaciens strain LBA4404 carrying the pBI binary vector for PgA1B1 protein expression was used for transformation. Cotyledons and young leaves were cut into 3-5 mm explants and incubated in Agrobacterium suspension ($OD_{600}$ nm 0.5) for 10 min. After blotting dry with sterile filter paper, explants were transferred to solid MS co-cultivation medium supplemented with 100 µM acetosyringone and incubated in the dark for 2 days at 24° C. After co-cultivation, explants were transferred to the first selection/regeneration MS medium supplemented with 30 g/L sucrose, 1 mg/L BAP, 1 mg/L thidiazuron, 0.3 mg/L NAA, 30 mg/L kanamycin, 300 mg/L timentin and 8 g/L agar. After 10 days, explants were transferred to the second selection/regeneration MS medium supplemented with 30 g/L sucrose, 1 mg/L BAP, 1 mg/L thidiazuron, 0.1 mg/L NAA, 50 mg/L kanamycin, 300 mg/L timentin and 8 g/L agar. After 4-5 weeks of culturing on the second selection medium, putatively transformed green shoots were formed (FIGS. 6A-6B and 6D). It was noticed that the cotyledon explants produced 2.5 times more putative transgenic shoots than the leaf explants. Healthy green shoots that reached 1-2 cm in height were excised and transferred to the MS medium supplemented with 30 g/L sucrose, 8 g/L agar, 300 mg/L timentin and 50 mg/L kanamycin for rooting. Putative transgenic shoots produced roots after 1-2 weeks of cultivation and showed good growth on the selection medium (FIG. 6C).

Figure 6E:
FIGS. 6A-6E illustrate in vitro selection of transgenic *Echinaceia angustifolia* plants engineered to express a recombinant TBL protein.
Figure 6B:
Figure 6D:
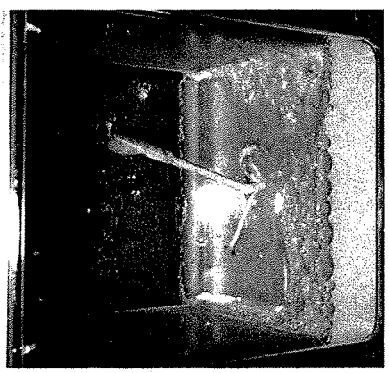
Figure 6A:
Figure 6C:
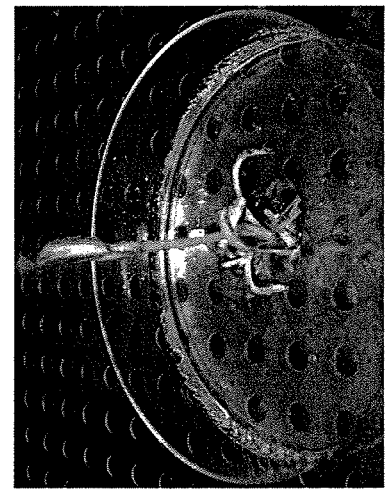

Transgenic plants were further screened with Western blotting for the presence of the PgA1B1-c-myc fusions using the c-myc monoclonal antibody mAb (ATCC, Manassas) and the goat anti-mouse horse radish conjugated antibody (Ab) (Upstate NY) (FIG. 6E). As shown on FIG. 6E, the recombinant product of the expected size of approximately 50 kDa was detected in many samples.

Transformation of Kalanchoe Plants.

Plant material. Fresh leaves of Kalanchoe pinnata were obtained from Tropilab Inc. (St. Petersburg, Fla.) and surface sterilized by immersion in 70% ethanol for 1 min, followed by soaking in 25% of bleach solution for 8 min. After rinsing 3 times in sterile distilled water, and blotting dry with sterile filter paper, leaf segments (1×1 cm) were cultured on MS basal medium supplemented with 30 g/l sucrose, 1 mg/l BAP, 0.1 mg/l NAA and 7 g/l agar. Explants were cultivated at 24° C. at 16 h-light/8 h-dark photoperiods and 40 µE/m2/S1 light intensity. Explants developed shoots after 5-6 weeks in culture. Shoots were excised and transferred to the Magenta boxes containing basal MS medium supplemented with 30 g/L sucrose and 7 g/L agar. Shoots formed roots and produced whole plants within 3-5 weeks. For propagation of plant material stem segments with axillary buds were transferred to the fresh MS medium supplemented with 30 g/L sucrose and 7 g/L agar.

Transformation.

Agrobacterium tumefaciens strain LBA4404 containing the pBI-PgA1B1 construct was used for transformation experiments. Agrobacteria were grown at 28° C. on solid LB plates supplemented with 50 mg/L kanamycin and 20 mg/L rifampicin. A single colony was used to inoculate 20 mL of LB liquid medium with the same antibiotics. Agrobacterium culture was incubated 1-2 days at 150 rpm on a shaker. The suspension of Agrobacterium was diluted with a liquid MS medium to obtain $OD_{600}$ 0.5.

Figure 7C:
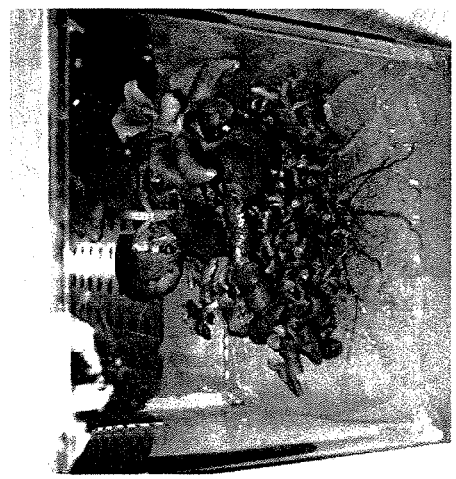
FIGS. 7A-7C illustrate in vitro selection of transgenic *Kalanchoe pinnata* plants engineered to express a recombinant TBL protein
Figure 7B:
Figure 7A:

For transformation experiments leaves of aseptically propagated 2 moths-old plants were cut into 0.6 to 0.7 cm pieces and inoculated with Agrobacterium suspensions for 10 min. After blotting dry with sterile filter paper, explants were transferred to the co-cultivation MS medium supplemented with 100 µM acetosyringone and incubated in the dark for 2 days at 24° C. After co-cultivation, explants were transferred to the selection regeneration MS basal medium supplemented with 2 mg/L BAP, 0.1 mg/L NAA, 50 mg/L kanamycin and 300 mg/L timentin. All explants were subcultured every 2-3 weeks onto the fresh medium with the same combination of plant hormones and antibiotics. After 5-6 weeks, explants produced shoots on the selection medium (FIG. 7A). FIG. 7A shows the transformed explant developing shoots (left) and the non-transformed explant bleaching on the selection medium containing 50 mg/L of kanamycin. Putative transgenic green regenerants were transferred to MS medium supplemented with 50 mg/L kanamycin and 300 mg/L timentin for rooting (FIG. 7B). In the presence of 50 mg/L kanamycin transgenic kalanchoe shoots showed good growth and development of roots compare to the non-transgenic shoots that did not produce roots and eventually died. FIG. 7C shows the transgenic kalanhoe plant rooted on the selection medium. Transgenic kalanchoe plants had showed no morphological abnormalities and resembled non-transgenic plants of the same age.

FIG. 8 is a schematic drawing explaining the process of production of plant-derived composition. As shown in this figure, vectors that include the expression constructs encoding recombinant ATR proteins are introduced into either crop or medicinal plants. The recombinant ATR proteins are extracted and may be used in plant-derived therapeutic compositions either alone or in combination with enhancers and adjuvants.

Example 4. Analysis of Activity of Synthetic Recombinant Proteins

Extraction of Soluble Protein from Transgenic Tobacco Plants.

Figure 9A:
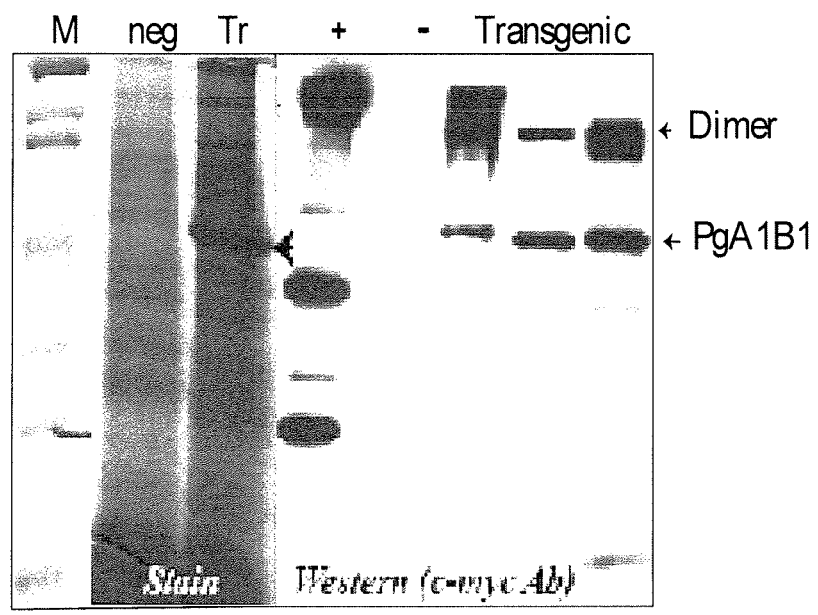
FIGS. 9A-9C illustrate analyses of the PgA1-B1 proteins produced in plants.

Total and soluble plant proteins were extracted from transgenic tobacco and medicinal plants as described by Golovkin et al., 2007. Plant tissue sample were collected, immediately frozen in liquid nitrogen and stored at −80° C. until extraction. Recombinant product was extracted from frozen plant tissues directly using equal amount (V/W) of Laemmli loading buffer for the total/insoluble extract or soluble buffer containing 0.1M Na phosphate pH7.4, 0.3M NaCl, 3% Glycerol, 0.1 mM EDTA, 2 mM β-ME and 0.05% of plant protease inhibitors cocktail (Sigma) for a total soluble protein, concentrated and brought into an equal volume of loading buffer. Protein was extracted from the transgenic tobacco line shown on was used for further analysis (FIG. 9A).

Extraction of Protein from Transgenic Echinacea Plants.

Total plant protein was extracted from transgenic Echinacea plants using similar protocol as in Golovkin et al., 2007. Plant tissue sample were collected, immediately frozen in liquid nitrogen and store at −80° C. until extraction. Recombinant product was extracted from frozen plant tissues directly with equal amount (V/W) of Laemmli loading buffer and further used for Western blot analysis (FIG. 6E).

Purification of Soluble Recombinant Proteins

About 200 g of frozen leaf material was grounded in 5 volumes of the extraction buffer containing 50-100 mM Na Phosphate, pH7.4, 0.3M NaCl, 0.2% Tween-20, 1.5 mM β-Mercaptoethanol, 0.05% Plant Protein Inhibitors Cocktail (Sigma) using Brinkman Polytron Homogenizer at 27,000 rpm. Insoluble parts were pelleted (Beckman) at 16,000 rpm for 20 min at 4° C. Following the flow-filtering through Miracloth (Calbiochem), the PgA1B1 protein was purified in a single-step protocol, using protein A agarose as described earlier (Spitsin et al., 2009; Andrianov et al., 2010). FIG. 9C illustrates extraction of the plant PgA1B1 recombinant protein from tobacco leaf tissue and purification of the recombinant protein on the protein-A agarose column. In this figure, "M" is a protein molecular weight marker, "IgG" is a purified conventional IgG antibody with the heavy ("H") and light ("L") chains eluted from the protein-A agarose column and used as a standard. "Total" stands for a total plant protein extract before purification. "FT" indicates flow through the fraction from the column. "Eluate" marks the final purified plant-derived PgA1B1 product identified as the "PgA1B1" 48 kDa band monomer of the PgA1B1 protein and the upper "dimer" band.

In vitro characterization and quantification of protein expression was performed with ELISA and Western blot analysis (FIG. 9A) essentially as described by Golovkin et al., 2007. FIG. 9A shows a total protein extracted from the transgenic tobacco plant on PAAG gel (left panel) and immunodetection of PgA1B1 protein expressed in plants using Western blotting (right panel). In this figure, "M" is a protein molecular weight marker, "neg" is an extract of untransformed plant, "Tr" marks total proteins from PgA1B1-expressing transgenic plants, "+" is a positive control from bacteria, "−" is a total protein extract from a wild type plant, "Transgenic" refers to protein extracts from different transgenic tobacco lines. "PgA1B1" indicates the position of the 48 kDa TBL-Fc fusion protein and upper band represents the corresponding "dimer".

Figure 9B:
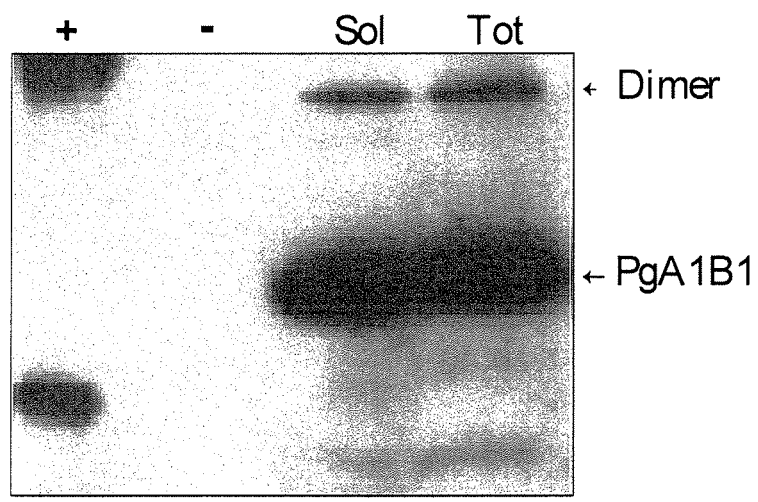
Figure 9C:
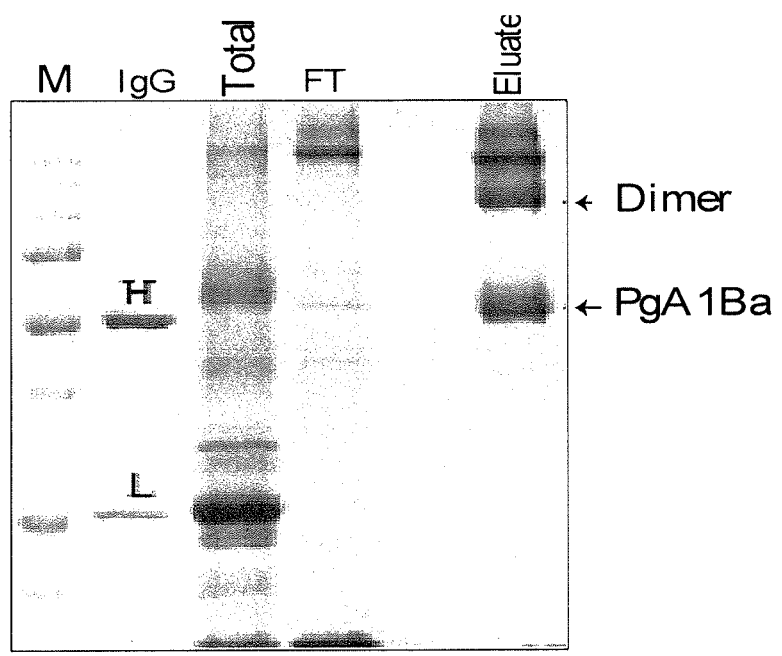

FIG. 9B demonstrates comparison of a total and soluble PgA1B1 protein in transgenic tobacco plants using Western blot analysis. In this figure, "+" is a positive control, "−" is a negative control from wild type plants, "Sol" and "Tot" stands for soluble and total protein fractions, respectively. Analysis as shown in FIG. 9B confirmed that almost all fusion proteins are expressed as soluble proteins in plants. Highly pure preparations of plant-derived PgA1B1 protein were extracted from plant tissue minimal concentration of 1.5 mg/ml and yield of at least 3 mg per Kg of raw plant tissue weight.

Example 5. Affinity Binding of the Anthrax Toxin by Plant-Derived Toxin Binding Ligand As shown earlier by VWA/I domain of the native CMG2 protein may bind PA in a divalent cation-dependent manner (Bradley et al., 2001; Lacy et al., 2004; Scobie et al. 2003). The ability of plant-derived PgAB fusion protein to bind PA was confirmed by two kinds of experiments.

Affinity Pulls Down Assay of PA Protein from Solution

Affinity of the PA protein to the plant-derived PgA1B1 protein was demonstrated by using protein A agarose beads. Specific binding of 0.5 µg of commercial anthrax PA protein (List Laboratories, Campbell, Calif.) was mixed with 5 µl (=7.25 µg) of purified PgA1B1 protein was done in 100 µl of TBS buffer containing 0.05 Tween-20 (TBST5), 3% BSA, and 1 mM $MgCl_2$ by incubating it at 4° C. overnight with gentle shaking. A positive control, 2 µl (aprox. 8-10 µg) of commercial anti-PA goat antiserum (List Laboratories, Campbell, Calif.) was used instead of PgA1B1 protein. Bound protein complexes were rescued from the solution using MagnaBind Protein A Beads (Pierce, Rockford, Ill.). The beads were eluted and analyzed by Western immunoassay using anti-PA mAbs (Biodesign, Saco, Me.). Both anti-PA mAbs and plant-derived PgA1B1 were shown to efficiently bind PA protein. Under experimental conditions, a plant-derived PgA1B1 recombinant protein was more efficient in binding anthrax toxin PA component then the control commercial antibody.

Detection of Binding PA Protein to Plant-Derived TBL by ELISA

Figure 10A:
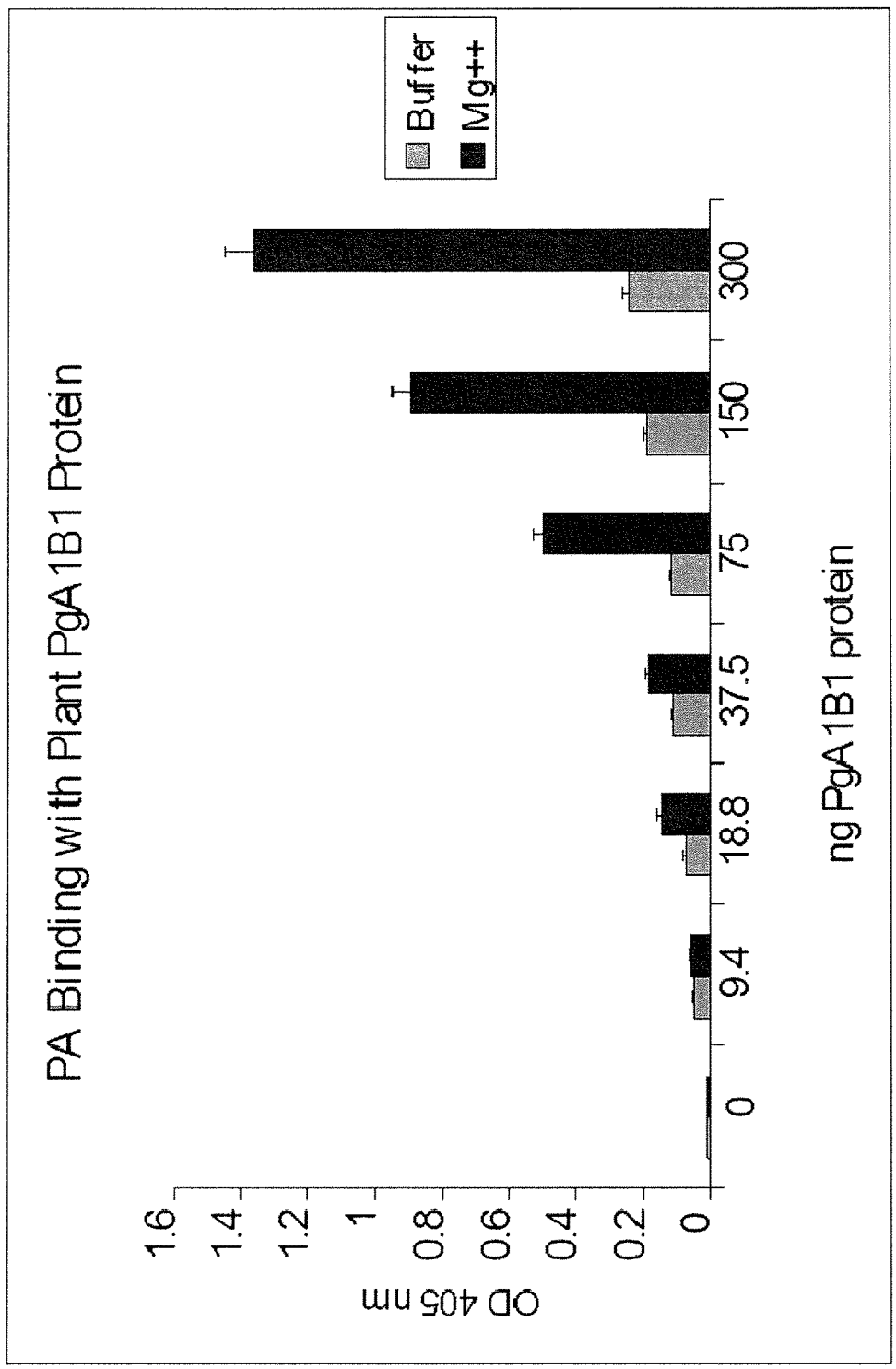
FIGS. 10A-10B illustrate the ability of the recombinant protein PgA1-B1 to protect cells against the anthrax toxin.

FIG. 10A illustrates an analysis of the PA binding by the recombinant PgA1B1 protein. Concentration dependency of the plant-derived PgA1B1 binding to the surface-immobilized of PA protein was detected by sandwich ELISA. ELISA was performed in a 96-well plate coated with 0.3 µg/well of the PA protein (List Laboratories, Campbell, Calif.) preparation in 50 µl TBS per well at 4° C. overnight followed by blocking with TBS containing 0.025% Tween (TBST2.5) and 3% BSA. The PA protein preparation was incubated with increasing concentrations of plant PgA1B1 in the presence (dark bars) of or without magnesium ions ($Mg^{2+}$) (light bars). Bound PgA1B1 was detected using c-myc-specific mAbs. Dilutions of PgA1B1 protein starting at 300 ng/well in 50 µl TBST2.5 with 1 mM $MgCl_2$ were added and incubated 1 h to set up binding, then washed 2×5' in TBST2.5. Primary c-myc specific antibody (Invitrogen, Carlsbad, Calif.) were applied at 1/1000-1/2000 dilution for an hour washed vigorously in TBST2.5. After incubation with secondary AP-anti-mouse conjugate (Sigma, Saint Louis, Mo.) at 1/2000 dilution, plates were developed by using pNPP Substrate (Sigma, Saint Louis, Mo.) as recommended by manufacturer and $OD_{405}$ nm determined. Strong affinity of PgA1B1 to PA was demonstrated in the presence of $Mg^{2+}$ ions, which is characteristic to a native ATR/sCMG2 protein (Scobie et al. 2003).

In Vitro Protection of Macrophage Cells Against Anthrax Toxin with Plant ATR.

Figure 10B:
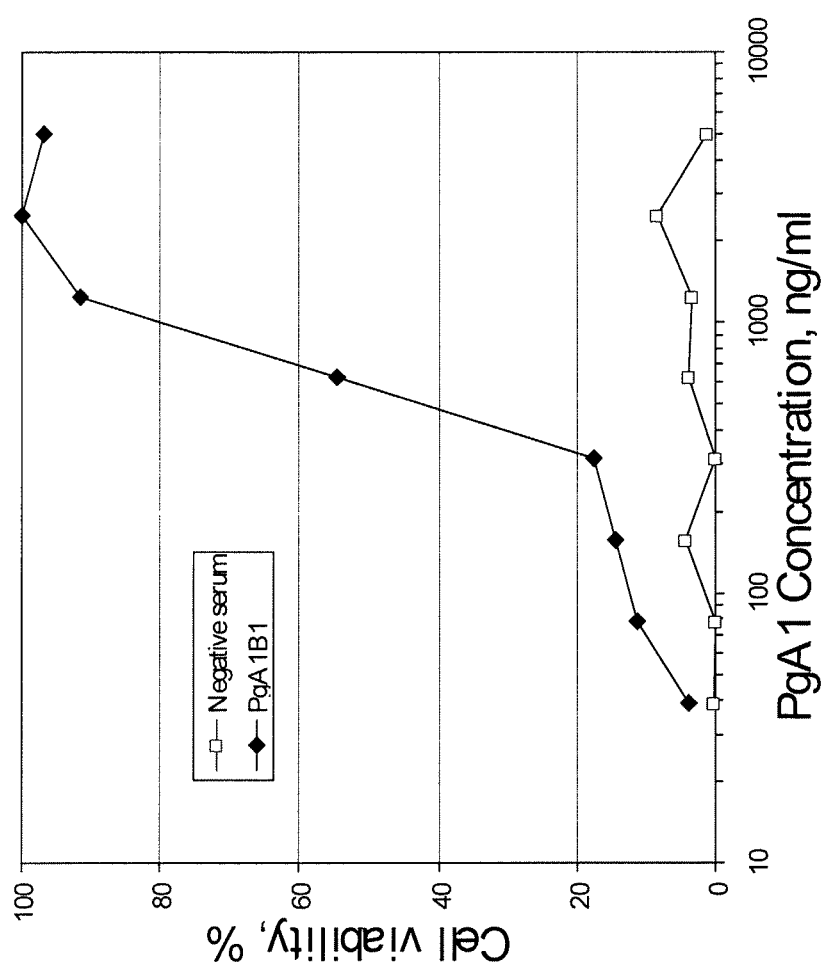

Referring to FIG. 10B neutralizing-antibody activity was determined in host monocyte-macrophages cells J774A.1 (American Type Culture Collection, Manassas, Va.) essentially as described by Little et al., 1990. Various concentrations of purified plant PgA1B1 (diamonds) or an irrelevant serum from mice immunized with PBS buffer (Negative serum, squares) were premixed with the anthrax lethal toxin before addition to the monocyte-macrophage J774A.1 cells. Cells were incubated with lethal concentrations of the PA-LF toxin in the presence of different concentrations of either the recombinant PgA1B1 protein or sera from mice immunized with PBS buffer (Negative serum). Lactate dehydrogenase activity was measured by a Cytotoxicity Detection Kit (Roche, Indianapolis, Ind.). Cell viability was calculated as a percentage of surviving cells to the complete lysis achieved with 1% Triton X-100. Data points represent the deviation of mean values in triplicate samples. PA and LF components of the anthrax toxin (at 0.1 µg/ml) were combined with plant purified PgA1B1 and negative serum. The antiserum-toxin mixtures were added to J774A.1 at $4 \times 10^4$ cells per well. Lactate dehydrogenase activity was measured by the Cytotoxicity Detection kit (Roche, Indianapolis, Ind.). The percentage of cell lysis was calculated as the mean of "$A_{490}$ of serum/PA toxin/target cell mix" minus "$A_{490}$ of target cell control" divided by "$A_{490}$ of cells treated with 2% Triton X-100" minus "A490 of cells incubated with medium." Neutralization of anthrax toxin was observed for purified plant-derived PgA1B1 at working concentration of 0.6 µg/ml where 50% cells survived confirming its capability to protect cells against the anthrax toxin. That is in a good agreement with previously described result for native sCMG2 protein (Scobie et al., 2005; Vuyisich et al., 2008; Wycoff et al., 2011; Thomas et al., 2012). No neutralization activity was detected in negative control serum.

Example 6. Administration of Antitoxin Composition to a Subject

Administration of a therapeutic antitoxin composition into bloodstream of animal subjects could be done with the help of commercial needle-free technique developed by Apogee Technologies (Norwood, Mass.), based on using micro needle patches for transdermal administration of protein-based therapeuticals. Up to 1.5 µg/cm² of c-myc tagged PgA1B1 plant-derived protein, produced as described in Example 1, was loaded onto the micro-needle patch in a formulation recommended by manufacturer. The patches containing micro-needle array are then manually applied on the skin and released upon a pressure applied on the center of the patch for 1 min to facilitate micro-needle insertion. After 30 min the amount of intramuscular recombinant protein could be estimated histologically using c-myc-specific antibody demonstrating complete dissolution of the formulation in the animal.

REFERENCES

Andrianov V., Brodzik R., Spitsin S., Bandurska K., McManus H., Koprowski H., Golovkin M. Production of recombinant anthrax toxin receptor (ATR/CMG2) fused with human Fc in planta. *Protein Expression and Purification* 70:158-162 (2010).

Bradley K. A., Mogridge J., Mourez M., Collier R. J., Young J. A. Identification of the cellular receptor for anthrax toxin. *Nature* 414:225-229 (2001).

Golovkin M., Spitsin S., Andrianov V., et al., Smallpox subunit vaccine produced in planta confers protection in mice. *Proc. Natl. Acad. Sci.*, 104:6864-6869 (2007).

Golovkin M. Production of recombinant pharmaceuticals using plant biotechnology. In: Bioprocess Science and Technology, Series Biochemistry Research Trends Ed. Min-Tze Liong. Nova Sci. Publ., Inc., USA. ISBN:978-1-61122-950-9 (2011).

Golovkin M. Plant-Derived vaccines: Plant biotechnology for production of recombinant pharmaceuticals, *Human Vaccines* 7(3), Landes Bioscience (2011).

Lacy D. B., Wigelsworth D. J., Scobie H. M., Young J. A. and Collier R. J. Crystal structure of the von Willebrand factor A domain of human capillary morphogenesis protein 2: an anthrax toxin receptor. *Proc Natl Acad Sci USA*, 101: 6367-6372 (2004).

Manayani D. J., Thomas D., Dryden K. A., Reddy V., Siladi M. E., Marlett J. M., Rainey G. J. A., Pique M. E., Scobie H. M., Yeager M., Young J. A. T. A viral nanoparticle with dual function as an anthrax antitoxin and vaccine. *PLoS Pathog* 3:e142 (2007).

Rainey G. J. A., Young J. A. T. Antitoxins: novel strategies to target agents of bioterrorism. *Nat. Rev. Microbiol.*, 2: 721-726 (2004).

Scobie H. M., et al. Human capillary morphogenesis protein 2 functions as an anthrax toxin receptor. *Proc Natl Acad Sci USA*, 100: 5170-74 (2003).

Scobie H. M., et al. A soluble receptor decoy protects rats against anthrax lethal toxin challenge. *The Journal of Infectious Diseases*, 192: 1047-51 (2005).

Spitsin S., Andrianov V., Pogrebnyak N. et al., Immunological assessment of plant-derived avian flu H5/HA1 variants. *Vaccine*, 27:1289-1292 (2009).

Thomas D., Naughton J., Cote C., Welkos S., Manchester M., Young J. A. T. Delayed toxicity associated with soluble anthrax toxin receptor decoy-Ig fusion protein treatment. *PLoS ONE*, 7:e34611 (2012).

Vuyisich M., Gnanakaran S., Lovchik J. A., Lyons C. R., Gupta G. A dual-purpose protein ligand for effective therapy and sensitive diagnosis of anthrax. *Protein J* 27:292-302 (2008).

Wycoff K. L., Belle A., Deppe D., Schaefer L, Maclean J. M., Haase S., Trilling A. K., Liu S., Leppla S. H., Geren I. N., Pawlik J., Peterson J. W. Recombinant Anthrax Toxin Receptor-Fc Fusion Proteins Produced in Plants Protect Rabbits against Inhalational Anthrax. *Antimicrobial Agents and Chemotherapy* 55:132-139 (2011).

Young J. A., Collier R. J. Anthrax Toxin: Receptor Binding, Internalization, Pore Formation, and Translocation. *Annu. Rev. Biochem.* 76:243-265 (2007).

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

The invention claimed is:

1. A genetic construct comprising a first polynucleotide, a second polynucleotide, and a third polynucleotide, wherein the first polynucleotide comprises SEQ ID NO: 2 which encodes a toxin binding ligand, the second polynucleotide comprises SEQ ID NO: 6 which encodes Fc-IgG, and the third polynucleotide comprises SEQ ID NO: 14 which encodes a helper element, and wherein the genetic construct further comprises nucleotide sequence encoding a flexible linker and a short peptide between said first and second polynucleotide, wherein the flexible linker comprises the amino acid sequence of SEQ ID NO: 44 and the short peptide comprises the amino acid sequence of SEQ ID NOS: 45, 46, or both.

2. A recombinant protein produced by the genetic construct of claim 1.

3. A transgenic plant comprising the genetic construct of claim 1.

4. The transgenic plant of claim 3, wherein the plant is a crop plant selected from the group consisting of: tomato, tobacco, pepper, eggplant, lettuce, oilseed rape, broccoli, cauliflower, cabbage crops, cucumber, melon, pumpkin, squash, peanut, soybeans, corn, rice, barley, buckwheat, sugar cane, cotton, beans, cassava, potatoes, sweet potatoes, and okra.

5. The transgenic plant of claim 3, wherein the plant is a medicinal plant selected from the group consisting of: *Caragana sinica, Codonopsis pilosulae, Hedyotis diffusa, Houttuynia cordata, Lonicera japonica, Morinda officinalis, Oenothera odorata, Kalanchoe pinnata, Echinacea angustifolia, Calendula officinalis*, and *Arthemis nobilis*.

6. A method of producing a recombinant protein in a plant, said method comprising: contacting a plant with the genetic construct of claim 1 and obtaining a plant comprising the genetic construct and the recombinant protein, wherein the recombinant protein is encoded by the genetic construct.

7. The method of claim 6, said method further comprising isolating and purifying the recombinant protein from the plant.

8. A method of preparing a composition effective for treating or preventing an anthrax infection in a subject, said method comprising providing the recombinant protein produced by the method of claim 6.

9. The method of claim 8, said method further comprising providing a pharmaceutically acceptable carrier.

10. The method of claim 8, said method further comprising an adjuvant.

11. A method of protecting a subject against an anthrax infection, said method comprising: providing a composition that includes the recombinant protein of claim 2, wherein the composition is effective in preventing or reducing at least one symptom of an anthrax infection in a subject, and administering the composition to a subject in need thereof.

12. The method of claim 11, wherein the subject is a mammal.

13. The method of claim 12, wherein the mammal is selected from the group consisting of: an agricultural animal, an equine, a zoo animal, a research animal, and a human.

14. The method of claim 11, wherein administering includes a route selected from the group consisting of: intravenous, intramuscular, intraperitoneal, intradermal, mucosal, cutaneous and subcutaneous.

15. The method of claim 11, wherein administering is intranasal.

16. The method of claim 11, wherein intranasal administering is provided in the form of inhalation or nasal drops.

* * * * *

SEQUENCE LISTING

<160> NUMBER OF SEQ ID NOS: 65

<210> SEQ ID NO 1
<211> LENGTH: 581
<212> TYPE: DNA
<213> ORGANISM: Artificial Sequence
<220> FEATURE:
<223> OTHER INFORMATION: Synthetic construct, PgA1-1 construct

<400> SEQUENCE: 1

| | | |
|---|---|---|
| ccatggaaca accttcttgt cgtcgagctt ttgatcttta ttttgttctt gataaatctg | 60 | |
| gttctgttgc taataattgg attgaaattt ataattttgt tcaacaactt gctgaaagat | 120 | |
| ttgtttctcc tgaaatgaga ctttctttta ttgtttttc ttctcaagct actattattc | 180 | |
| ttcctcttac tggtgataga ggaaaaattt ctaaaggact tgaggatttg aaaagagttt | 240 | |
| ctcctgttgg tgaaacttat attcatgagg gacttaaact tgctaatgaa caaattcaaa | 300 | |
| aagctggtgg tcttaaaact tcttctatta ttattgctct tactgatgga aaacttgatg | 360 | |
| gtcttgttcc ttcttatgct gaaaagaag ctaaaatttc aagatcactt ggtgcttctg | 420 | |
| tttattgtgt tggtgttctt gattttgaac aagctcaact tgaaagaatt gctgattcta | 480 | |
| aagaacaagt ttttcctgtt aagggtggat ttcaagctct taaggaatt attaattcta | 540 | |
| ttcttgctca atcttgtact gaagatctcc aataagagct c | 581 | |

<210> SEQ ID NO 2
<211> LENGTH: 575
<212> TYPE: DNA
<213> ORGANISM: Artificial Sequence
<220> FEATURE:
<223> OTHER INFORMATION: Synthetic construct, PgA1-2 construct

<400> SEQUENCE: 2

| | | |
|---|---|---|
| ccatggaaca accttcttgt cgtcgagctt ttgatcttta ttttgttctt gataaatctg | 60 | |
| gttctgttgc taataattgg attgaaattt ataattttgt tcaacaactt gctgaaagat | 120 | |
| ttgtttctcc tgaaatgaga ctttctttta ttgtttttc ttctcaagct actattattc | 180 | |
| ttcctcttac tggtgataga ggaaaaattt ctaaaggact tgaggatttg aaaagagttt | 240 | |
| ctcctgttgg tgaaacttat attcatgagg gacttaaact tgctaatgaa caaattcaaa | 300 | |
| aagctggtgg tcttaaaact tcttctatta ttattgctct tactgatgga aaacttgatg | 360 | |
| gtcttgttcc ttcttatgct gaaaagaag ctaaaatttc aagatcactt ggtgcttctg | 420 | |
| tttattgtgt tggtgttctt gattttgaac aagctcaact tgaaagaatt gctgattcta | 480 | |
| aagaacaagt ttttcctgtt aagggtggat ttcaagctct taaggaatt attaattcta | 540 | |
| ttcttgctca atcttgtact gaagatctcc aataa | 575 | |

<210> SEQ ID NO 3
<211> LENGTH: 722
<212> TYPE: DNA
<213> ORGANISM: Artificial Sequence
<220> FEATURE:
<223> OTHER INFORMATION: Synthetic construct, PgA2-1 construct

<400> SEQUENCE: 3

| | | |
|---|---|---|
| ccatgggtga cgtcggtatg cacgtcaagg agaaggagaa gaacaaggac gagaacaagc | 60 | |
| gtaaggacga ggagcgtaac aagacccagg aggagcacct caaggagatc atgaagcaca | 120 | |
| tcgtcaagat cgaggtcaag ggtgaggagg ctgtcaagaa ggaggctgct gagaagctcc | 180 | |
| tcgagaaggt cccttctgac gtcctcgaga tgtacaaggc tatcggtggt aagatctaca | 240 | |

```
tcgtcgacgg tgacatcacc aagcacatct ctctcgaggc tctctctgag gacaagaaga      300
agatcaagga catctacggt aaggacgctc tcctccacga gcactacgtc tacgctaagg      360
agggttacga gcctgtcctc gtcatccagt cttctgagga ctacgtcgag aacaccgaga      420
aggctctcaa cgtctactac gagatcggta agatcctctc tcgtgacatc ctctctaaga      480
tcaaccagcc ttaccagaag ttcctcgacg tcctcaacac catcaagaac gcttctgact      540
ctgacggtca ggacctcctc ttcaccaacc agctcaagga gcaccctacc gacttctctg      600
tcgagttcct cgagcagaac tctaacgagg tccaggaggt cttcgctaag gctttcgctt      660
actacatcga gcctcagcac cgtgacgtcc tccagctcta cgctcctgag gcttaagagc      720
tc                                                                    722

<210> SEQ ID NO 4
<211> LENGTH: 728
<212> TYPE: DNA
<213> ORGANISM: Artificial Sequence
<220> FEATURE:
<223> OTHER INFORMATION: Synthetic construct, PgA2-2 construct

<400> SEQUENCE: 4
ccatgggtga cgtcggtatg cacgtcaagg agaaggagaa gaacaaggac gagaacaagc       60
gtaaggacga ggagcgtaac aagacccagg aggagcacct caaggagatc atgaagcaca      120
tcgtcaagat cgaggtcaag ggtgaggagg ctgtcaagaa ggaggctgct gagaagctcc      180
tcgagaaggt cccttctgac gtcctcgaga tgtacaaggc tatcggtggt aagatctaca      240
tcgtcgacgg tgacatcacc aagcacatct ctctcgaggc tctctctgag gacaagaaga      300
agatcaagga catctacggt aaggacgctc tcctccacga gcactacgtc tacgctaagg      360
agggttacga gcctgtcctc gtcatccagt cttctgagga ctacgtcgag aacaccgaga      420
aggctctcaa cgtctactac gagatcggta agatcctctc tcgtgacatc ctctctaaga      480
tcaaccagcc ttaccagaag ttcctcgacg tcctcaacac catcaagaac gcttctgact      540
ctgacggtca ggacctcctc ttcaccaacc agctcaagga gcaccctacc gacttctctg      600
tcgagttcct cgagcagaac tctaacgagg tccaggaggt cttcgctaag gctttcgctt      660
actacatcga gcctcagcac cgtgacgtcc tccagctcta cgctcctgag gctggagatc      720
tccaataa                                                              728

<210> SEQ ID NO 5
<211> LENGTH: 732
<212> TYPE: DNA
<213> ORGANISM: Bacillus anthracis
<220> FEATURE:
<221> NAME/KEY: misc_feature
<222> LOCATION: (1)..(732)
<223> OTHER INFORMATION: PgA2-3, DNA encoding PA-binding domain LFn

<400> SEQUENCE: 5
gagaataaga gaaaagatga agaacgaaat aaaacacagg aagagcattt aaaggaaatc       60
atgaaacaca ttgtaaaaat agaagtaaaa ggggaggaag ctgttaaaaa agaggcagca      120
gaaaagctac ttgagaaagt accatctgat gttttagaga tgtataaagc aattggagga      180
aagatatata ttgtggatgg tgatattaca aaacatatat ctttagaagc attatctgaa      240
gataagaaaa aaataaaaga catttatggg aagatgcttt attcatgacattatgta        300 tatgcaaaag aaggatatga acccgtactt gtaatccaat cttcggaaga ttatgtgaa      360
```

```
aatactgaaa aggcactgaa cgtttattat gaaataggta agatattatc aagggatatt    420
ttaagtaaaa ttaatcaacc atatcagaaa tttttagatg tattaaatac cattaaaaat    480
gcatctgatt cagatggaca agatctttta tttactaatc agcttaagga acatcccaca    540
gacttttctg tagaattctt ggaacaaaat agcaatgagg tacaagaagt atttgcgaaa    600
gcttttgcat attatatcga gccacagcat cgtgatgttt tacagcttta tgcaccggaa    660
gcttttaatt acatggataa atttaacgaa caagaaataa atctatcctt ggaagaactt    720
aaagatcaac gg                                                       732

<210> SEQ ID NO 6
<211> LENGTH: 687
<212> TYPE: DNA
<213> ORGANISM: Artificial Sequence
<220> FEATURE:
<223> OTHER INFORMATION: Synthetic construct, PgB1-1 construct

<400> SEQUENCE: 6
gataaaactc atacttgtcc tccttgtcct gctcctgaac ttcttggtgg tccttctgtt     60 tttcttttc ctcctaaacc taaagatact cttatgattt ctcgtactcc tgaagttact    120
tgtgttgttg ttgatgtttc tcatgaagat cctgaagtta aatttaattg gtatgttgat    180
ggtgttgaag ttcataatgc taaaactaaa cctcgtgaag aacaatataa ttctacttat    240
cgtgttgttt ctgttcttac tgttcttcat caagattggc ttaatggtaa agaatataaa    300
tgtaaagttt ctaataaagc tcttcctgct cctattgaaa aaactatttc taaagctaaa    360
ggtcaacctc gtgaacctca agtttatact cttcctcctt ctcgtgaaga atgactaaa    420 aatcaagttt ctcttacttg tcttgttaaa ggttttatc cttctgatat tgctgttgaa    480
tgggaatcta atggtcaacc tgaaaataat tataaaacta ctcctcctgt tcttgattct    540
gatggttctt ttttttcttta ttctaaactt actgttgata aatctcgttg gcaacaaggt    600
aatgtttttt cttgttctgt tatgcatgaa gctcttcata atcattatac tcaaaaatct    660
ctttctcttt ctcctggtaa agatctt                                       687

<210> SEQ ID NO 7
<211> LENGTH: 774
<212> TYPE: DNA
<213> ORGANISM: Artificial Sequence
<220> FEATURE:
<223> OTHER INFORMATION: Synthetic construct, PgB2-1 construct

<400> SEQUENCE: 7
gatgttactg ttccttgtcc tgttccttct actcctccta ctccttctcc ttctactcct     60
cctactcctt ctccttcttg ttgtcatcct cgtctttctc ttcatcgtcc tgctcttgaa    120
gatcttcttc ttggttctga agctaatctt acttgtactc ttactggtct tcgtgatgct    180
tctggtgtta cttttacttg gactccttct tctggtaaat ctgctgttca aggtcctcct    240
gaacgtgatc tttgtggttg ttattctgtt tcttctgttc ttcctggttg tgctgaacct    300
tggaatcatg gtaaaacttt tacttgtact gctgcttatc ctgaatctaa aactcctctt    360
actgctactc tttctaaatc tggtaatact tttcgtcctg aagttcatct tcttcctcct    420
ccttctgaag aacttgctct taatgaactt gttactctta cttgtcttgc tcgtggtttt    480
tctcctaaag atgttcttgt tcgttggctt caaggttctc aagaacttcc tcgtgaaaaa    540
tatcttactt gggcttctcg tcaagaacct tctcaaggta ctactacttt tgctgttact    600
tctattcttc gtgttgctgc tgaagattgg aaaaaaggtg atactttttc ttgtatggtt    660
```

```
ggtcatgaag ctcttcctct tgcttttact caaaaaacta ttgatcgtct tgctggtaaa    720
cctactcatg ttaatgtttc tgttgttatg gctgaagttg atggtacttg ttat          774
```

<210> SEQ ID NO 8
<211> LENGTH: 1006
<212> TYPE: DNA
<213> ORGANISM: Artificial Sequence
<220> FEATURE:
<223> OTHER INFORMATION: Synthetic construct, PgB3-1 construct

<400> SEQUENCE: 8

```
gttcctcttc ctgttattgc tgaacttcct cctaaagttt ctgtttttgt tcctcctcgt     60
gatggttttt ttggtaatcc tcgtaaatct aaacttattt gtcaagctac tggttttttct   120 cctcgtcaaa ttcaagtttc ttggcttcgt gaaggtaaac aagttggttc tggtgttact   180
actgatcaag ttcaagctga agctaaagaa tctggtccta ctacttataa agttacttct   240
actcttacta ttaaagaatc tgattggctt tctcaatcta tgtttacttg tcgtgttgat   300
catcgtggtc ttacttttca acaaaatgct tcttctatgt gtgttcctga tcaagatact   360
gctattcgtg tttttgctat tcctccttct tttgcttcta tttttcttac taaatctact   420
aaacttactt gtcttgttac tgatcttact acttatgatt ctgttactat tcttggact    480 cgtcaaaatg gtgaagctgt taaaactcat actaatattt ctggatgatt ggaattctgg   540
tgaacgtttt acttgtactg ttactcatac tgatcttcct tctcctctta acaaactat    600 ttctcgtcct aaaggtgttg ctcttcatcg tcctgatgtt tatcttcttc ctcctgctcg   660
tgaacaactt aatcttcgtg aatctgctac tattacttgt cttgttactg gttttctcc    720 tgctgatgtt tttgttcaat ggatgcaacg tggtcaacct ctttctcctg aaaaatatgt   780
tacttctgct cctatgcctg aacctcaagc tcctggtcgt tattttgctc attctattct   840
tactgtttct gaagaagaat ggaatactgg tgaaacttat acttgtgttg ttgctcatga   900
agctcttcct aatcgtgtta ctgaacgtac tgttgataaa tctactggta aacctactct   960
ttataatgtt tctcttgtta tgtctgatac tgctggtact tgttat                  1006
```

<210> SEQ ID NO 9
<211> LENGTH: 1431
<212> TYPE: DNA
<213> ORGANISM: Artificial Sequence
<220> FEATURE:
<223> OTHER INFORMATION: Synthetic construct, PgB1-2 construct

<400> SEQUENCE: 9

```
atggactgga cctggaggtt cctctttgtg gtggcagcag ctacaggtgt ccagtcccag     60
gtgcagctgg tgcagtctgg ggctgaggtg aagaagcctg gtcctcggt gaaggtctcc    120 tgcaaggctt ctggaggcac cttcaacagg tatactgtca actgggtgcg acaggcccct   180
ggacaagggc ttgagtggat gggaggcatc atccctatct ttggtacagc aaactacgca   240
cagaggttcc agggcagact caccattacc gcggacgaat ccacgagcac agcctacatg   300
gagctgagca gcctgagatc tgatgacacg gccgtgtatt tctgtgcgag agagaatctc   360
gataattcgg ggacttatta ttatttctca ggctggttcg accctggggg ccagggaacc   420
ctggtcaccg tctcctcagc ctccaccaag ggcccatcgg tcttcccct ggcaccctcc    480 tccaagagca cctctggggg cacagcggcc ctgggctgcc tggtcaagga ctacttcccc   540
gaaccggtga cggtgtcgtg gaactcaggc gccctgacca gcggcgtgca caccttcccg   600
```

| | |
|---|---:|
| gctgtcctac agtcctcagg actctactcc ctcagcagcg tggtgaccgt gccctccagc | 660 |
| agcttgggca cccagaccta catctgcaac gtgaatcaca agcccagcaa caccaaggtg | 720 |
| gacaagagag ttgagcccaa atcttgtgac aaaactcaca catgcccacc gtgcccagca | 780 |
| cctgaactcc tggggggacc gtcagtcttc ctcttccccc caaaacccaa ggacaccctc | 840 |
| atgatctccc ggacccctga ggtcacatgc gtggtggtgg acgtgagcca cgaagaccct | 900 |
| gaggtcaagt tcaactggta cgtggacggc gtggaggtgc ataatgccaa gacaaagccg | 960 |
| cgggaggagc agtacaacag cacgtaccgt gtggtcagcg tcctcaccgt cctgcaccag | 1020 |
| gactggctga atggcaagga gtacaagtgc aaggtctcca acaaagccct cccagccccc | 1080 |
| atcgagaaaa ccatctccaa agccaagggg cagccccgag aaccacaggt gtacaccctg | 1140 |
| cccccatccc gggaggagat gaccaagaac caggtcagcc tgacctgcct ggtcaaaggc | 1200 |
| ttctatccca gcgacatcgc cgtggagtgg gagagcaatg ggcagccgga gaacaactac | 1260 |
| aagaccacgc ctcccgtgct ggactccgac ggctccttct tcctctatag caagctcacc | 1320 |
| gtggacaaga gcaggtggca gcaggggaac gtcttctcat gctccgtgat gcatgaggct | 1380 |
| ctgcacaacc actacacgca gaagagcctc tccctgtccc cgggtaaatg a | 1431 |

<210> SEQ ID NO 10
<211> LENGTH: 1799
<212> TYPE: DNA
<213> ORGANISM: Artificial Sequence
<220> FEATURE:
<223> OTHER INFORMATION: Synthetic construct, PgB2-2 construct

<400> SEQUENCE: 10

| | |
|---|---:|
| cctctctgtg ctgggttcct ccagtgtaga ggagaggcag gtacagcctg tcctcctggg | 60 |
| gacatggcat gagggccgcg tcctcacagc gcattctgtg ttccagcatc cccgaccagc | 120 |
| cccaaggtct tcccgctgag cctcgacagc accccccaag atgggaacgt ggtcgtcgca | 180 |
| tgcctggtcc agggcttctt cccccaggag ccactcagtg tgacctggag cgaaagcgga | 240 |
| cagaacgtga ccgccagaaa cttcccacct agccaggatg cctccgggga cctgtacacc | 300 |
| acgagcagcc agctgaccct gccggccaca cagtgcccag acggcaagtc cgtgacatgc | 360 |
| cacgtgaagc actacacgaa ttccagccag gatgtgactg tgccctgccg aggtcagagg | 420 |
| gcaggctggg gagtggggcg gggccacccc gtcctgccct gacactgcgc ctgcacccgt | 480 |
| gttccccaca gggagccgcc ccttcactca caccagagtg gaccgcgggc cgagccccag | 540 |
| gaggtggtgg tggacaggcc aggaggggcg aggcggggc acggggaagg gcgttctgac | 600 |
| cagctcaggc catctctcca ctccagttcc cccacctccc ccatgctgcc accccgact | 660 |
| gtcgctgcac cgaccggccc tcgaggacct gctcttaggt tcagaagcga acctcacgtg | 720 |
| cacactgacc ggcctgagag atgcctctgg tgccaccttc acctggacgc cctcaagtgg | 780 |
| gaagagcgct gttcaaggac cacctgagcg tgacctctgt ggctgctaca gcgtgtccag | 840 |
| tgtcctgcct ggctgtgccc agccatggaa ccatggggag accttcacct gcactgctgc | 900 |
| ccaccccgag ttgaagaccc cactaaccgc caacatcaca aaatccggtg gtccagacc | 960 |
| ctgctcgggg ccctgctcag tgctctggtt tgcaaagcat attcccggcc tgcctcctcc | 1020 |
| ctcccaatcc tgggctccag tgctcatgcc aagtacagag ggaaactgag gcaggctgag | 1080 |
| gggccaggac acagcccagg gtgcccacca gagcagaggg gctctctcat cccctgccca | 1140 |
| gcccctgac ctggctctct accctccagg aaacacattc cggcccgagg tccacctgct | 1200 |
| gccgccgccg tcggaggagc tggccctgaa cgagctggtg acgctgacgt gcctggcacg | 1260 |

```
tggcttcagc cccaaggatg tgctggttcg ctggctgcag gggtcacagg agctgccccg     1320
cgagaagtac ctgacttggg catcccggca ggagcccagc cagggcacca ccaccttcgc     1380
tgtgaccagc atactgcgcg tggcagccga ggactggaag aaggggggaca ccttctcctg    1440 catggtgggc cacgaggccc tgccgctggc cttcacacag aagaccatcg accgcttggc     1500
gggtaaaccc acccatgtca atgtgtctgt tgtcatggcg gaggtggacg gcacctgcta    1560
ctgagccgcc cgcctgtccc cacccctgaa taaactccat gctcccccaa gcagccccac    1620
gcttccatcc ggcgcctgtc tgtccatcct cagggtctca gcacttggga aagggccagg    1680
gcatggacag ggaagaatac cccctgccct gagcctcggg gggcccctgg cacccccatg    1740
agactttcca ccctggtgtg agtgtgagtt gtgagtgtga gagtgtgtgg tgcaggagg     1799
```

<210> SEQ ID NO 11  
<211> LENGTH: 1453  
<212> TYPE: DNA  
<213> ORGANISM: Artificial Sequence  
<220> FEATURE:  
<223> OTHER INFORMATION: Synthetic construct, PgB3-2 construct

<400> SEQUENCE: 11

```
gggagtgcat ccgccccaac ccttttcccc ctcgtctcct gtgagaattc cccgtcggat       60
acgagcagcg tggccgttgg ctgcctcgca caggacttcc ttcccgactc catcactttc      120
tcctggaaat acaagaacaa ctctgacatc agcagcaccc ggggcttccc atcagtcctg      180 agaggggca agtacgcagc cacctcacag gtgctgctgc cttccaagga cgtcatgcag       240
ggcacagacg aacacgtggt gtgcaaagtc agcaccccca cggcaacaa agaaaagaac       300 gtgcctcttc cagtgattgc cgagctgcct cccaaagtga gcgtcttcgt cccaccccgc      360
gacggcttct tcggcaaccc ccgcaagtcc aagctcatct gccaggccac gggtttcagt      420
cccccggaga ttcaggtgtc ctggctgcgc gaggggaagc aggtgggtc tggcgtcacc       480 acggaccagg tgcaggctga ggccaaagag tctgggccca cgacctacaa ggtgaccagc      540
acactgacca tcaaagagag cgactggctc agccagagca tgttcacctg ccgcgtggat      600
cacaggggcc tgaccttcca gcagaatgcg tcctccatgt gtgtccccga tcaagacaca     660
gccatccggg tcttcgccat ccccccatcc tttgccagca tcttcctcac caagtccacc      720
aagttgacct gcctggtcac agacctgacc acctatgaca cgtgaccat ctcctggacc       780 cgccagaatg gcgaagctgt gaaaacccac accaacatct ccgagagcca ccccaatgcc     840
actttcagcg ccgtgggtga ggccagcatc tgcgaggatg actggaattc cggggagagg    900
ttcacgtgca ccgtgaccca cacagacctg ccctcgccac tgaagcagac catctcccgg     960
cccaaggggg tggccctgca caggcccgat gtctacttgc tgccaccagc ccgggagcag    1020
ctgaacctgc gggagtcggc caccatcacg tgcctggtga cgggcttctc tccgcggac     1080 gtcttcgtgc agtggatgca gagggggcag cccttgtccc cggagaagta tgtgaccagc    1140
gccccaatgc ctgagcccca ggcccaggc cggtacttcg cccacagcat cctgaccgtg     1200
tccgaagagg aatggaacac gggggagacc tacacctgcg tggtgcccca tgaggccctg    1260
cccaacaggg tcaccgagag gaccgtggac aagtccaccg gtaaacccac cctgtacaac    1320
gtgtccctgg tcatgtccga cacagctggc acctgctact gaccctgctg gcctgcccac     1380
aggctcgggg cggctggccg ctctgtgtgt gcatgcaaac taacccgtgt caacggggtg    1440
agatgttgca tct                                                        1453
```

<210> SEQ ID NO 12
<211> LENGTH: 1035
<212> TYPE: DNA
<213> ORGANISM: Artificial Sequence
<220> FEATURE:
<223> OTHER INFORMATION: Synthetic construct, PgB4-1 construct

<400> SEQUENCE: 12

```
atgggtgccg cacttgcact tttgggggac ctagttgcta ctgtttctga ggctgctgct      60
gccacaggat tttcagtagc tgaaattgct gctggagagg ctgctgctac tatagaagtt     120
gaaattgcat cccttgctac tgtagagggg attacaagta cctctgaggc tatagctgct     180
ataggcctta ctcctgaaac atatgctgta ataactggag ctccgggggc tgtagctggg     240
tttgctgcat ggttcaaac tgtaactggt ggtagtgcta ttgctcagtt gggatataga      300
ttttttgctg actgggatca taaagtttca acagttgggc tttttcagca gccagctatg     360
gctttacaat tatttaatcc agaagactac tatgatattt tatttcctgg agtgaatgcc     420
tttgttaaca atattcacta tttagatcct agacattggg gcccgtcctt gttctccaca     480
atctcccagg ctttttggaa tcttgttaga gatgatttgc cagccttaac ctctcaggaa     540
attcagagaa gaacccaaaa actatttgtt gaaagtttag caaggttttt ggaagaaact     600
acttgggcaa tagttaattc accagctaac ttatataatt atatttcaga ctattattct     660
agattgtctc cagttaggcc ctctatggta aggcaagttg cccaaaggga gggaacctat     720
atttcttttg gccactcata cacccaaagt atagatgatg cagacagcat tcaagaagtt     780
acccaaaggc tagattttaa aaccccaaat gtgcaatctg tgaatttat agaaagaagt      840
attgcaccag gaggtgcaaa tcaaagatct gctcctcaat ggatgttgcc tttacttta      900
gggttgtacg ggactgtaac acctgctctt gaagcatatg aagatggccc caacaaaaag     960
aaaaggagaa aggaaggacc ccgtgcaagt tccaaaactt cttataagag gaggagtaga    1020
agttctagaa gttaa                                                     1035
```

<210> SEQ ID NO 13
<211> LENGTH: 1800
<212> TYPE: DNA
<213> ORGANISM: Arabidopsis thaliana
<220> FEATURE:
<221> NAME/KEY: misc_feature
<222> LOCATION: (1)..(1800)
<223> OTHER INFORMATION: PgB5-1 construct

<400> SEQUENCE: 13

```
ccatggctat acccaacctc ggtcttggtc acaccaggaa ctctctggta agctagctcc      60
actccccaga acaaccggc gccaaattgc cggaattgct gacctgaaga cggaacatca     120
tcgtcgggtc cttgggcgat tgcggcggaa gatgggtcag cttgggcttg aggacgagac     180
ccgaatcgag tctgttgaaa ggttgttcat tgggatttgt atacggagat tggtcgtcga     240
gaggtttgag ggaaaggaca aatgggttg gctctggaga aagagagtgc ggctttagag      300
agagaattga gaggtttaga gagagatgcg gcggcgatga cgggaggaga gacgacgagg     360
acctgcatta tcaaagcagt gacgtggtga aatttggaac ttttaagagg cagatagatt     420
tattatttgt atccattttc ttcattgttc tagaatgtcg cggaacaaat tttaaaacta     480
aatcctaaat ttttctaatt ttgttgccaa tagtggatat gtgggccgta tagaaggaat     540
ctattgaagg cccaaaccca tactgacgag cccaaaggtt cgttttgcgt tttatgtttc     600
ggttcgatgc caacgccaca ttctgagcta ggcaaaaaac aaacgtgtct ttgaatagac     660
```

```
tcctctcgtt aacacatgca gcggctgcat ggtgacgcca ttaacacgtg gcctacaatt      720
gcatgatgtc tccattgaca cgtgacttct cgtctccttt cttaatatat ctaacaaaca      780
ctcctacctc ttccaaaata tatacacatc tttttgatca atctctcatt caaaatctca      840
ttctctctag taaacaagaa caaaaaaatg gcggatacag ctagaggaac ccatcacgat      900
atcatcggca gagaccagta cccgatgatg ggccgagacc gagaccagta ccagatgtcc      960
ggacgaggat ctgactactc caagtctagg cagattgcta aagctgcaac tgctgtcaca     1020
gctggtggtt ccctccttgt tctctccagc cttacccttg ttggaactgt catagctttg     1080
actgttgcaa cacctctgct cgttatcttc agcccaatcc ttgtcccggc tctcatcaca     1140
gttgcactcc tcatcaccgg ttttctttcc tctggagggt ttggcattgc cgctataacc     1200
gttttctctt ggatttacaa gtaagcacac atttatcatc ttacttcata attttgtgca     1260
atatgtgcat gcatgtgttg agccagtagc tttggatcaa ttttttttggt cgaataacaa     1320 atgtaacaat aagaaattgc aaattctagg gaacatttgg ttaactaaat acgaaatttg     1380
acctagctag cttgaatgtg tctgtgtata tcatctatat aggtaaaatg cttggtatga     1440
tacctattga ttgtgaatag gtacgcaacg ggagagcacc cacagggatc agacaagttg     1500
gacagtgcaa ggatgaagtt gggaagcaaa gctcaggatc tgaaagacag agctcagtac     1560
tacggacagc aacatactgg tggggaacat gaccgtgacc gtactcgtgg tggccagcac     1620
actacttaag ttaccccact gatgtcatcg tcatagtcca ataactccaa tgtcggggag     1680
ttagtttatg aggaataaag tgtttagaat ttgatcaggg ggagataata aaagccgagt     1740
ttgaatcttt ttgttataag taatgtttat gtgtgtttct atatgttgtc aaatggtacc     1800
```

<210> SEQ ID NO 14
<211> LENGTH: 1413
<212> TYPE: DNA
<213> ORGANISM: Artificial Sequence
<220> FEATURE:
<223> OTHER INFORMATION: Synthetic construct, PgC1-1 construct

<400> SEQUENCE: 14

```
ttgtgattgt ttttagtttg ttagctgcct ggagtgttat tttaagaaag cagaagcacc       60
atcatttgca cactccttat agatcacaca ccttaacccct gacttttttt gctccagttt      120
ttcagaagaa gtgaagtcaa gatgaagaac catttgcttt tctggggagt cctggcggtt      180
tttattaagg ctgttcatgt gaaagcccaa gaagatgaaa ggattgttct tgttgacaac      240
aaatgtaagt gtgcccggat tacttccagg atcatccgtt cttccgaaga tcctaatgag      300
gacattgtgg agagaaacat ccgaattatt gttcctctga caacaggga gaatatctct      360 gatcccacct caccattgag aaccagattt gtgtaccatt tgtctgacct ctgtaaaaaa      420
tgtgatccta cagaagtgga gctggataat cagatagtta ctgctaccca gagcaatatc      480
tgtgatgaag acagtgctac agagacctgc tacacttatg acagaaacaa gtgctacaca      540
gctgtggtcc cactcgtata tggtggtgag accaaaatgg tggaaacagc cttaacccca      600
gatgcctgct atcctgacta atttaagtca ttgctgactg catagctctt tttcttgaga      660
ggctctccat tttgattcag aaagttagca tatttattac caatgaattt gaaaccaggg      720 ctttttttttt tttttgggtg atgtaaaacc aactccctgc caccaaaata attaaaatag      780
tcacattgtt atctttatta ggtaatcact tcttaattat atgttcatac tctaagtatc      840
aaaatcttcc aattatcatg ctcacctgaa agaggtatgc tctcttagga atacagtttc      900
```

| | |
|---|---|
| tagcattaaa caaataaaca aggggagaaa ataaaactca aggactgaaa atcaggaggt | 960 |
| gtaataaaat gttcctcgca ttccccccg cttttttttt tttttttgac tttgccttgg | 1020 |
| agagccagag cttccgcatt ttctttacta ttcttttaa aaaaagtttc actgtgtaga | 1080 |
| gaacatatat gcataaacat aggtcaatta tatgtctcca ttagaaaaat aataattgga | 1140 |
| aaacatgttc tagaactagt tacaaaaata atttaaggtg aaatctctaa tatttataaa | 1200 |
| agtagcaaaa taaatgcata attaaaatat atttggacat aacagacttg aagcagatg | 1260 |
| atacagactt cttttttttca taatcaggtt agtgtaagaa attgccattt gaaacaatcc | 1320 |
| attttgtaac tgaaccttat gaaatatatg tatttcatgg tacgtattct ctagcacagt | 1380 |
| ctgagcaatt aaatagattc ataagcataa aaa | 1413 |

<210> SEQ ID NO 15
<211> LENGTH: 1065
<212> TYPE: DNA
<213> ORGANISM: Artificial Sequence
<220> FEATURE:
<223> OTHER INFORMATION: Synthetic construct, PgC2-1 construct

<400> SEQUENCE: 15

| | |
|---|---|
| atggccccaa caaaaagaaa aggagaaagg aaggaccccg tgcaagttcc aaaacttctt | 60 |
| ataagaggag gagtagaagt tctagaagtt aaaactgggg ttgactcaat tacagaggta | 120 |
| gaatgctttt taactccaga aatgggtgac ccagatgagc atcttagggg ttttagtaag | 180 |
| tcaatatcta tatcagatac atttgaaagt gactccccaa atagggacat gcttccttgt | 240 |
| tacagtgtgg ccagaattcc actacccaat ctaaatgagg atctaacctg tggaaaatata | 300 |
| ctcatgtggg aggctgtgac cttaaaaact gaggttatag gggtgacaag tttgatgaat | 360 |
| gtgcactcta atgggcaagc aactcatgac aatggtgcag ggaagccagt gcagggcacc | 420 |
| agctttcatt ttttttctgt tggggggag gctttagaat tacaggggt gcttttaat | 480 |
| tacagaacaa agtacccaga tggaacaatt tttccaaaga atgccacagt gcaatctcaa | 540 |
| gtcatgaaca cagagcacaa ggcgtaccta gataagaaca aagcatatcc tgttgaatgt | 600 |
| tgggttcctg atcccaccag aaatgaaaac acaagatatt tgggacact aacaggagga | 660 |
| gaaaatgttc ctccagttct tcatataaca aacactgcca caacagtgtt gcttgatgaa | 720 |
| tttggtgttg ggccactttg caaaggtgac aacttatact tgtcagctgt tgatgtctgt | 780 |
| ggcatgttta caaacaggtc tggttcccag cagtggagag gactctccag atattttaag | 840 |
| gtgcagctaa ggaaaaggag ggttaaaaac ccctacccaa tttcttttcct tcttactgat | 900 |
| ttaattaaca gaaggactcc tagagttgat gggcagccta tgtatggcat ggatgctcaa | 960 |
| gtagaggagg ttagagtttt tgagggaaca gaggagcttc caggggaccc agacatgatg | 1020 |
| agatacgttg acaaatatgg acagttgcag acaaaaatgc tgtaa | 1065 |

<210> SEQ ID NO 16
<211> LENGTH: 1286
<212> TYPE: DNA
<213> ORGANISM: Artificial Sequence
<220> FEATURE:
<223> OTHER INFORMATION: Synthetic construct, PgA1-3:B1-3 contsruct

<400> SEQUENCE: 16

| | |
|---|---|
| ccatggaaca accttcttgt cgtcgagctt ttgatcttta ttttgttctt gataaatctg | 60 |
| gttctgttgc taataattgg attgaaattt ataatttgt tcaacaactt gctgaaagat | 120 |
| ttgtttctcc tgaaatgaga ctttctttta ttgttttttc ttctcaagct actattattc | 180 |

```
ttcctcttac tggtgataga ggaaaaattt ctaaaggact tgaggatttg aaaagagttt      240
ctcctgttgg tgaaacttat attcatgagg gacttaaact tgctaatgaa caaattcaaa      300
aagctggtgg tcttaaaact tcttctatta ttattgctct tactgatgga aaacttgatg      360
gtcttgttcc ttcttatgct gaaaagaag ctaaaatttc aagatcactt ggtgcttctg       420
tttattgtgt tggtgttctt gattttgaac aagctcaact tgaaagaatt gctgattcta      480
aagaacaagt ttttcctgtt aagggtggat ttcaagctct taaggaatt attaattcta       540 ttcttgctca atcttgtact gcggccgcag gaggtggatc tggaaattct gacaagaccc      600
acacctgccc tccttgccct gctcctgagc tcctcggtgg tccttctgtc ttcctcttcc      660
ctcctaagcc taaggacacc ctcatgatct ctcgtacccc tgaggtcacc tgcgtcgtcg      720
tcgacgtctc tcacgaggac cctgaggtca agttcaactg gtacgtcgac ggtgtcgagg      780
tccacaacgc taagaccaag cctcgtgagg agcagtacaa ctctacctac cgtgtcgtct      840
ctgtcctcac cgtcctccac caggactggc tcaacggtaa ggagtacaag tgcaaggtct      900
ctaacaaggc tctccctgct cctatcgaga agaccatctc taaggctaag ggtcagcctc      960
gtgagcctca ggtctacacc ctccctcctt ctcgtgagga gatgaccaag aaccaggtct     1020
ctctcacctg cctcgtcaag ggtttctacc cttctgacat cgctgtcgag tgggagtcta     1080
acggtcagcc tgagaacaac tacaagacca cccctcctgt cctcgactct gacggttctt     1140
tcttcctcta ctctaagctc accgtcgaca gtctcgttg gcagcagggt aacgtcttct      1200
cttgctctgt catgcacgag gctctccaca accactacac ccagaagtct ctctctctct     1260
ctcctggtaa ggacctctaa gagctc                                           1286

<210> SEQ ID NO 17
<211> LENGTH: 1337
<212> TYPE: DNA
<213> ORGANISM: Artificial Sequence
<220> FEATURE:
<223> OTHER INFORMATION: Synthetic construct, PgA1-4:B1-4 construct

<400> SEQUENCE: 17
ccatggaaca accttcttgt cgtcgagctt ttgatcttta ttttgttctt gataaatctg       60
gttctgttgc taataattgg attgaaattt ataattttgt tcaacaactt gctgaaagat      120
ttgtttctcc tgaaatgaga ctttcttta ttgtttttc ttctcaagct actattattc        180
ttcctcttac tggtgataga ggaaaaattt ctaaaggact tgaggatttg aaaagagttt      240
ctcctgttgg tgaaacttat attcatgagg gacttaaact tgctaatgaa caaattcaaa      300
aagctggtgg tcttaaaact tcttctatta ttattgctct tactgatgga aaacttgatg      360
gtcttgttcc ttcttatgct gaaaagaag ctaaaatttc aagatcactt ggtgcttctg       420
tttattgtgt tggtgttctt gattttgaac aagctcaact tgaaagaatt gctgattcta      480
aagaacaagt ttttcctgtt aagggtggat ttcaagctct taaggaatt attaattcta       540 ttcttgctca atcttgtact gcggccgcag gaggtggatc tggaaattct gacaagaccc      600
acacctgccc tccttgccct gctcctgagc tcctcggtgg tccttctgtc ttcctcttcc      660
ctcctaagcc taaggacacc ctcatgatct ctcgtacccc tgaggtcacc tgcgtcgtcg      720
tcgacgtctc tcacgaggac cctgaggtca agttcaactg gtacgtcgac ggtgtcgagg      780
tccacaacgc taagaccaag cctcgtgagg agcagtacaa ctctacctac cgtgtcgtct      840
ctgtcctcac cgtcctccac caggactggc tcaacggtaa ggagtacaag tgcaaggtct      900
```

```
ctaacaaggc tctccctgct cctatcgaga agaccatctc taaggctaag ggtcagcctc    960
gtgagcctca ggtctacacc ctccctcctt ctcgtgagga gatgaccaag aaccaggtct   1020
ctctcacctg cctcgtcaag ggtttctacc cttctgacat cgctgtcgag tgggagtcta   1080
acggtcagcc tgagaacaac tacaagacca cccctcctgt cctcgactct gacggttctt   1140
tcttcctcta ctctaagctc accgtcgaca agtctcgttg gcagcagggt aacgtcttct   1200
cttgctctgt catgcacgag gctctccaca accactacac ccagaagtct ctctctctct   1260
ctcctggtaa ggacctcgat ctccaaaagc ttattagcga ggaggatctt catcaccatc   1320
accatcacta agagctc                                                   1337
```

<210> SEQ ID NO 18
<211> LENGTH: 1377
<212> TYPE: DNA
<213> ORGANISM: Artificial Sequence
<220> FEATURE:
<223> OTHER INFORMATION: Synthetic construct, PgA1-3:B2-3 construct

<400> SEQUENCE: 18

```
ccatggaaca accttcttgt cgtcgagctt ttgatctttta ttttgttctt gataaatctg     60
gttctgttgc taataattgg attgaaattt ataattttgt tcaacaactt gctgaaagat    120
ttgtttctcc tgaaatgaga ctttcttttta ttgtttttttc ttctcaagct actattattc    180
ttcctcttac tggtgataga ggaaaaattt ctaaaggact tgaggatttg aaaagagttt    240
ctcctgttgg tgaaacttat attcatgagg gacttaaact tgctaatgaa caaattcaaa    300
aagctggtgg tcttaaaact tcttctatta ttattgctct tactgatgga aaacttgatg    360
gtcttgttcc ttcttatgct gaaaagaag ctaaaatttc aagatcactt ggtgcttctg    420
tttattgtgt tggtgttctt gattttgaac aagctcaact tgaaagaatt gctgattcta    480
aagaacaagt ttttcctgtt aagggtggat ttcaagctct taaggaatt attaattcta    540 ttcttgctca atcttgtact gcggccgcag gaggtggatc tggaaattct gacgtcaccg    600
tcccttgccc tgtccttcc accctccta ccccttctcc ttctacccct cctacccctt     660
ctccttcttg ctgccaccct cgtctctctc tccaccgtcc tgctctcgag gacctcctcc    720
tcggttctga ggctaaccte acctgcaccc tcaccggtct ccgtgacgct tctggtgtca    780
ccttcacctg gaccccttct tctggtaagt ctgctgtcca gggtcctcct gagcgtgacc    840
tctgcggttg ctactctgtc tcttctgtcc tccctggttg cgctgagcct tggaaccacg    900
gtaagacctt cacctgcacc gctgcttacc ctgagtctaa gaccccctctc accgctaccc    960 tctctaagtc tggtaacacc ttccgtcctg aggtccacct cctcctcct ccttctgagg   1020 agctcgctct caacgagctc gtcaccctca cctgcctcgc tcgtggttc tctcctaagg   1080 acgtcctcgt ccgttggctc cagggttctc aggagctccc tcgtgagaag tacctcacct   1140
gggcttctcg tcaggagcct tctcaggta ccaccacctt cgctgtcacc tctatcctcc   1200
gtgtcgctgc tgaggactgg aagaaggtg acaccttctc ttgcatggtc ggtcacgagg   1260
ctctccctct cgctttcacc cagaagacca tcgaccgtct cgctggtaag cctacccacg   1320
tcaacgtctc tgtcgtcatg gctgaggtcg acggtacctg ctacccaata agagctc      1377
```

<210> SEQ ID NO 19
<211> LENGTH: 1373
<212> TYPE: DNA
<213> ORGANISM: Artificial Sequence
<220> FEATURE:
<223> OTHER INFORMATION: Synthetic construct, PgA1-4:B2-4 construct

<400> SEQUENCE: 19

```
ccatggaaca accttcttgt cgtcgagctt ttgatcttta ttttgttctt gataaatctg      60
gttctgttgc taataattgg attgaaattt ataattttgt tcaacaactt gctgaaagat     120
ttgtttctcc tgaaatgaga ctttctttta ttgttttttc ttctcaagct actattattc     180
ttcctcttac tggtgataga ggaaaaattt ctaaaggact tgaggatttg aaaagagttt     240
ctcctgttgg tgaaacttat attcatgagg gacttaaact tgctaatgaa caaattcaaa     300
aagctggtgg tcttaaaact tcttctatta ttattgctct tactgatgga aaacttgatg     360
gtcttgttcc ttcttatgct gaaaagaag ctaaaatttc aagatcactt ggtgcttctg      420
tttattgtgt tggtgttctt gattttgaac aagctcaact tgaagaatt gctgattcta      480
aagaacaagt tttcctgtt aagggtggat ttcaagctct taaggaatt attaattcta      540
ttcttgctca atcttgtact gcggccgcag gaggtggatc tggaaattct gacgtcaccg     600
tccctgccc tgtcccttct acccctccta cccttctcc ttctacccct cctacccctt      660
ctccttcttg ctgccaccct cgtctctctc tccaccgtcc tgctctcgag gacctcctcc     720
tcggttctga ggctaacctc acctgcaccc tcaccggtct ccgtgacgct tctggtgtca     780
ccttcacctg gaccccttct tctggtaagt ctgctgtcca gggtcctcct gagcgtgacc     840
tctgcggttg ctactctgtc tcttctgtcc tccctggttg cgctgagcct tggaaccacg     900
gtaagacctt cacctgcacc gctgcttacc ctgagtctaa gacccctctc accgctaccc     960
tctctaagtc tggtaacacc ttccgtcctg aggtccacct cctccctcct ccttctgagg    1020
agctcgctct caacgagctc gtcaccctca cctgcctcgc tcgtggtttc tctcctaagg    1080
acgtcctcgt ccgttggctc cagggttctc aggagctccc tcgtgagaag tacctcacct    1140
gggcttctcg tcaggagcct tctcagggta ccaccacctt cgctgtcacc tctatcctcc    1200
gtgtcgctgc tgaggactgg aagaagggtg acaccttctc ttgcatggtc ggtcacgagg    1260
ctctccctct cgctttcacc cagaagacca tcgaccgtct cgctggtaag cctacccacg    1320
tcaacgtctc tgtcgtcatg gctgaggtcg acggtacctg ctactaaaga tct            1373
```

<210> SEQ ID NO 20
<211> LENGTH: 1662
<212> TYPE: DNA
<213> ORGANISM: Artificial Sequence
<220> FEATURE:
<223> OTHER INFORMATION: Synthetic cosntruct, PgA1-3: B3-3 construct

<400> SEQUENCE: 20

```
ccatggaaca accttcttgt cgtcgagctt ttgatcttta ttttgttctt gataaatctg      60
gttctgttgc taataattgg attgaaattt ataattttgt tcaacaactt gctgaaagat     120
ttgtttctcc tgaaatgaga ctttctttta ttgttttttc ttctcaagct actattattc     180
ttcctcttac tggtgataga ggaaaaattt ctaaaggact tgaggatttg aaaagagttt     240
ctcctgttgg tgaaacttat attcatgagg gacttaaact tgctaatgaa caaattcaaa     300
aagctggtgg tcttaaaact tcttctatta ttattgctct tactgatgga aaacttgatg     360
gtcttgttcc ttcttatgct gaaaagaag ctaaaatttc aagatcactt ggtgcttctg      420
tttattgtgt tggtgttctt gattttgaac aagctcaact tgaagaatt gctgattcta      480
aagaacaagt tttcctgtt aagggtggat ttcaagctct taaggaatt attaattcta      540
ttcttgctca atcttgtact gcggccgcag gaggtggatc tggaaattct gtccctctcc     600
```

```
ctgtcatcgc tgagctccct cctaaggtct ctgtcttcgt ccctcctcgt gacggtttct      660
tcggtaaccc tcgtaagtct aagctcatct gccaggctac cggtttctct cctcgtcaga      720
tccaggtctc ttggctccgt gagggtaagc aggtcggttc tggtgtcacc accgaccagg      780
tccaggctga ggctaaggag tctggtccta ccacctacaa ggtcacctct accctcacca      840
tcaaggagtc tgactggctc tctcagtcta tgttcacctg ccgtgtcgac caccgtggtc      900
tcaccttcca gcagaacgct tcttctatgt gcgtccctga ccaggacacc gctatccgtg      960
tcttcgctat ccctccttct ttcgcttcta tcttcctcac caagtctacc aagctcacct     1020
gcctcgtcac cgacctcacc acctacgact ctgtcaccat ctcttggacc cgtcagaacg     1080
gtgaggctgt caagacccac accaacatct ctgagtctca ccctaacgct accttctctg     1140
ctgtcggtga ggcttctatc tgcgaggacg actggaactc tggtgagcgt ttcacctgca     1200
ccgtcaccca caccgacctc ccttctcctc tcaagcagac catctctcgt cctaagggtg     1260
tcgctctcca ccgtcctgac gtctacctcc tccctcctgc tcgtgagcag ctcaacctcc     1320
gtgagtctgc taccatcacc tgcctcgtca ccggtttctc tcctgctgac gtcttcgtcc     1380
agtggatgca gcgtggtcag cctctctctc ctgagaagta cgtcacctct gctcctatgc     1440
ctgagcctca ggctcctggt cgttacttcg ctcactctat cctcaccgtc tctgaggagg     1500
agtggaacac cggtgagacc tacacctgcg tcgtcgctca cgaggctctc cctaaccgtg     1560
tcaccgagcg taccgtcgac aagtctaccg gtaagcctac cctctacaac gtctctctcg     1620
tcatgtctga caccgctggt acctgctacc aataagagc tc                         1662

<210> SEQ ID NO 21
<211> LENGTH: 1658
<212> TYPE: DNA
<213> ORGANISM: Artificial Sequence
<220> FEATURE:
<223> OTHER INFORMATION: Synthetic construct, PgA1-2:B3-2 construct

<400> SEQUENCE: 21
ccatggaaca accttcttgt cgtcgagctt ttgatcttta ttttgttctt gataaatctg       60
gttctgttgc taataattgg attgaaattt ataattttgt tcaacaactt gctgaaagat      120
ttgtttctcc tgaaatgaga cttcttttta ttgttttttc ttctcaagct actattattc      180
ttcctcttac tggtgataga ggaaaaattt ctaaaggact tgaggatttg aaaagagttt      240
ctcctgttgg tgaaacttat attcatgagg gacttaaact tgctaatgaa caaattcaaa      300
aagctggtgg tcttaaaact tcttctatta ttattgctct tactgatgga aaacttgatg      360
gtcttgttcc ttcttatgct gaaaaagaag ctaaaatttc aagatcactt ggtgcttctg      420
tttattgtgt tggtgttctt gattttgaac aagctcaact tgaaagaatt gctgattcta      480
aagaacaagt ttttcctgtt aagggtggat ttcaagctct taaggaatt attaattcta      540 ttcttgctca atcttgtact gcggccgcag gaggtggatc tggaaattct gtccctctcc      600
ctgtcatcgc tgagctccct cctaaggtct ctgtcttcgt ccctcctcgt gacggtttct      660
tcggtaaccc tcgtaagtct aagctcatct gccaggctac cggtttctct cctcgtcaga      720
tccaggtctc ttggctccgt gagggtaagc aggtcggttc tggtgtcacc accgaccagg      780
tccaggctga ggctaaggag tctggtccta ccacctacaa ggtcacctct accctcacca      840
tcaaggagtc tgactggctc tctcagtcta tgttcacctg ccgtgtcgac caccgtggtc      900
tcaccttcca gcagaacgct tcttctatgt gcgtccctga ccaggacacc gctatccgtg      960
tcttcgctat ccctccttct ttcgcttcta tcttcctcac caagtctacc aagctcacct     1020
```

```
gcctcgtcac cgacctcacc acctacgact ctgtcaccat ctcttggacc cgtcagaacg    1080
gtgaggctgt caagacccac accaacatct ctgagtctca ccctaacgct accttctctg    1140
ctgtcggtga ggcttctatc tgcgaggacg actggaactc tggtgagcgt ttcacctgca    1200
ccgtcaccca caccgacctc ccttctcctc tcaagcagac catctctcgt cctaagggtg    1260
tcgctctcca ccgtcctgac gtctacctcc tccctcctgc tcgtgagcag ctcaacctcc    1320
gtgagtctgc taccatcacc tgcctcgtca ccggtttctc tcctgctgac gtcttcgtcc    1380
agtggatgca gcgtggtcag cctctctctc ctgagaagta cgtcacctct gctcctatgc    1440
ctgagcctca ggtcctggt cgttacttcg ctcactctat cctcaccgtc tctgaggagg     1500
agtggaacac cggtgagacc tacacctgcg tcgtcgctca cgaggctctc cctaaccgtg    1560
tcaccgagcg taccgtcgac aagtctaccg gtaagcctac cctctacaac gtctctctcg    1620
tcatgtctga caccgctggt acctgctact aaagatct                            1658

<210> SEQ ID NO 22
<211> LENGTH: 1064
<212> TYPE: DNA
<213> ORGANISM: Artificial Sequence
<220> FEATURE:
<223> OTHER INFORMATION: Synthetic construct: PgB4-2: A1-3construct

<400> SEQUENCE: 22
ccatgggtgc tgctctcgct ctcctcggtg acctcgtcgc taccgtctct gaggctgctg      60
ctgctaccgg tttctctgtc gctgagatcg ctgctggtga ggctgctgct accatcgagg     120
tcgagatcgc ttctctcgct accgtcgagg gtatcacctc tacctctgag gctatcgctg     180
ctatcggtct caccccctgag acctacgctg tcatcaccgg tgctcctggt gctgtcgctg    240
gtttcgctgc tctcgtccag accgtcaccg gtggttctgc tatcgctcag ctcggttacc     300
gtttcttcgc tgactgggac acaaggtctc ctaccgtcgg tctcttccag cagcctgcta     360
tggctctcca gctcttcaac cctgaggact actacgacat cctcttccct ggtgtcaacg     420
ctttcgtcaa caacatccac tacctcgacc ctcgtcactg gggtccttct ctcttctcta     480
ccatctctca ggctttctgg aacctcgtcc gtgacgacct ccctgctctc acctctcagg     540
agatccagcg tcgtacccag aagctcttcg tcgagtctct cgctcgtttc ctcgaggaga     600
ccacctgggc tatcgtcaac tctcctgcta acctctacaa ctacatctct gactactact     660
ctcgtctctc tcctgtccgt ccttctatgg tccgtcaggt cgctcagcgt gagggtacct     720
acatctcttt cggtcactct tacacccagt ctatcgacga cgctgactct atccaggagg     780
tcacccagcg tctcgacctc aagaccccta acgtccagtc tggtgagttc atcgagcgtt     840
ctatcgctcc tggtggtgct aaccagcgtt ctgctcctca gtggatgctc cctctcctcc     900
tcggtctcta cggtaccgtc accctgctc tcgaggctta cgaggacggt cctaacaaga     960
agaagcgtcg taaggagggt cctcgtgctt cttctaagac ctcttacaag cgtcgttctc    1020
gttcttctcg ttctggaggt ggatctggaa attctgcggc cgca                    1064

<210> SEQ ID NO 23
<211> LENGTH: 530
<212> TYPE: DNA
<213> ORGANISM: Artificial Sequence
<220> FEATURE:
<223> OTHER INFORMATION: Synthetic construct; PgA1-1:B5 construct

<400> SEQUENCE: 23
```

-continued

| | |
|---|---|
| ccatggccga cacggccagg ggcacgcacc acgacatcat cggcagggac cagtacccga | 60 |
| tgatgggcag ggacagggac cagtaccaga tgtccggcag gggctccgac tactccaagt | 120 |
| ccaggcagat cgccaaggcc gccacggccg tgacggccgg cggctccctc ctcgtgctct | 180 |
| cctccctcac gctcgtgggc acggtgatcg ccctcacggt ggccacgccg ctcctcgtga | 240 |
| tcttctcccc gatcctcgtg ccggccctca tcacggtggc cctcctcatc acgggcttcc | 300 |
| tctcctccgg cggcttcggc atcgccgcca tcacggtgtt ctcctggatc tacaagtacg | 360 |
| ccacgggcga gcacccgcag ggctccgaca agctcgactc cgccaggatg aagctcggct | 420 |
| ccaaggccca ggacctcaag gacagggccc agtactacgg ccagcagcac acgggcggcg | 480 |
| agcacgacag ggacaggacg aggggcggcc agcacacgac ggcggccgca | 530 |

<210> SEQ ID NO 24
<211> LENGTH: 186
<212> TYPE: PRT
<213> ORGANISM: Homo sapiens
<220> FEATURE:
<221> NAME/KEY: MISC_FEATURE
<222> LOCATION: (1)..(186)
<223> OTHER INFORMATION: A1-CMG2 protein

<400> SEQUENCE: 24

Glu Gln Pro Ser Cys Arg Arg Ala Phe Asp Leu Tyr Phe Val Leu Asp
1               5                   10                  15

Lys Ser Gly Ser Val Ala Asn Asn Trp Ile Glu Ile Tyr Asn Phe Val
            20                  25                  30

Gln Gln Leu Ala Glu Arg Phe Val Ser Pro Glu Met Arg Leu Ser Phe
        35                  40                  45

Ile Val Phe Ser Ser Gln Ala Thr Ile Ile Leu Pro Leu Thr Gly Asp
    50                  55                  60

Arg Gly Lys Ile Ser Lys Gly Leu Glu Asp Leu Lys Arg Val Ser Pro
65                  70                  75                  80

Val Gly Glu Thr Tyr Ile His Glu Gly Leu Lys Leu Ala Asn Glu Gln
                85                  90                  95

Ile Gln Lys Ala Gly Gly Leu Lys Thr Ser Ser Ile Ile Ile Ala Leu
            100                 105                 110

Thr Asp Gly Lys Leu Asp Gly Leu Val Pro Ser Tyr Ala Glu Lys Glu
        115                 120                 125

Ala Lys Ile Ser Arg Ser Leu Gly Ala Ser Val Tyr Cys Val Gly Val
    130                 135                 140

Leu Asp Phe Glu Gln Ala Gln Leu Glu Arg Ile Ala Asp Ser Lys Glu
145                 150                 155                 160

Gln Val Phe Pro Val Lys Gly Gly Phe Gln Ala Leu Lys Gly Ile Ile
                165                 170                 175

Asn Ser Ile Leu Ala Gln Ser Cys Thr Glu
            180                 185

<210> SEQ ID NO 25
<211> LENGTH: 244
<212> TYPE: PRT
<213> ORGANISM: Bacillus anthracis
<220> FEATURE:
<221> NAME/KEY: MISC_FEATURE
<222> LOCATION: (1)..(244)
<223> OTHER INFORMATION: A2-PA-LF protein

<400> SEQUENCE: 25

Glu Asn Lys Arg Lys Asp Glu Glu Arg Asn Lys Thr Gln Glu Glu His

```
                1               5                  10                 15
        Leu Lys Glu Ile Met Lys His Ile Val Lys Ile Glu Val Lys Gly Glu
                        20                 25                 30

Glu Ala Val Lys Lys Glu Ala Ala Glu Lys Leu Leu Glu Lys Val Pro
                        35                 40                 45

Ser Asp Val Leu Glu Met Tyr Lys Ala Ile Gly Gly Lys Ile Tyr Ile
         50                     55                 60

Val Asp Gly Asp Ile Thr Lys His Ile Ser Leu Glu Ala Leu Ser Glu
         65                     70                 75                 80

Asp Lys Lys Lys Ile Lys Asp Ile Tyr Gly Lys Asp Ala Leu Leu His
                        85                 90                 95

Glu His Tyr Val Tyr Ala Lys Glu Gly Tyr Glu Pro Val Leu Val Ile
                        100                105                110

Gln Ser Ser Glu Asp Tyr Val Glu Asn Thr Glu Lys Ala Leu Asn Val
                        115                120                125

Tyr Tyr Glu Ile Gly Lys Ile Leu Ser Arg Asp Ile Leu Ser Lys Ile
                        130                135                140

Asn Gln Pro Tyr Gln Lys Phe Leu Asp Val Leu Asn Thr Ile Lys Asn
        145                     150                155                160

Ala Ser Asp Ser Asp Gly Gln Asp Leu Leu Phe Thr Asn Gln Leu Lys
                        165                170                175

Glu His Pro Thr Asp Phe Ser Val Glu Phe Leu Glu Gln Asn Ser Asn
                        180                185                190

Glu Val Gln Glu Val Phe Ala Lys Ala Phe Ala Tyr Tyr Ile Glu Pro
                        195                200                205

Gln His Arg Asp Val Leu Gln Leu Tyr Ala Pro Glu Ala Phe Asn Tyr
                        210                215                220

Met Asp Lys Phe Asn Glu Gln Glu Ile Asn Leu Ser Leu Glu Glu Leu
        225                     230                235                240

Lys Asp Gln Arg

<210> SEQ ID NO 26
<211> LENGTH: 476
<212> TYPE: PRT
<213> ORGANISM: Homo sapiens
<220> FEATURE:
<221> NAME/KEY: MISC_FEATURE
<222> LOCATION: (1)..(476)
<223> OTHER INFORMATION: B1 protein

<400> SEQUENCE: 26

Met Asp Trp Thr Trp Arg Phe Leu Phe Val Val Ala Ala Ala Thr Gly
        1                       5                  10                 15

Val Gln Ser Gln Val Gln Leu Val Gln Ser Gly Ala Glu Val Lys Lys
                        20                 25                 30

Pro Gly Ser Ser Val Lys Val Ser Cys Lys Ala Ser Gly Gly Thr Phe
                        35                 40                 45

Asn Arg Tyr Thr Val Asn Trp Val Arg Gln Ala Pro Gly Gln Gly Leu
         50                     55                 60

Glu Trp Met Gly Gly Ile Ile Pro Ile Phe Gly Thr Ala Asn Tyr Ala
         65                     70                 75                 80

Gln Arg Phe Gln Gly Arg Leu Thr Ile Thr Ala Asp Glu Ser Thr Ser
                        85                 90                 95

Thr Ala Tyr Met Glu Leu Ser Ser Leu Arg Ser Asp Asp Thr Ala Val
                        100                105                110
```

```
Tyr Phe Cys Ala Arg Glu Asn Leu Asp Asn Ser Gly Thr Tyr Tyr Tyr
            115                 120                 125

Phe Ser Gly Trp Phe Asp Pro Trp Gly Gln Gly Thr Leu Val Thr Val
130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 27
<211> LENGTH: 340
<212> TYPE: PRT
<213> ORGANISM: Homo sapiens
<220> FEATURE:
<221> NAME/KEY: MISC_FEATURE
<222> LOCATION: (1)..(340)
<223> OTHER INFORMATION: B2 protein
```

<400> SEQUENCE: 27

| Ala | Ser | Pro | Thr | Ser | Pro | Lys | Val | Phe | Pro | Leu | Ser | Leu | Asp | Ser | Thr |
|---|---|---|---|---|---|---|---|---|---|---|---|---|---|---|---|
| 1 | | | | 5 | | | | | 10 | | | | | 15 | |
| Pro | Gln | Asp | Gly | Asn | Val | Val | Ala | Cys | Leu | Val | Gln | Gly | Phe | Phe | |
| | | | 20 | | | | 25 | | | | | 30 | | | |
| Pro | Gln | Glu | Pro | Leu | Ser | Val | Thr | Trp | Ser | Glu | Ser | Gly | Gln | Asn | Val |
| | | 35 | | | | | 40 | | | | 45 | | | | |
| Thr | Ala | Arg | Asn | Phe | Pro | Pro | Ser | Gln | Asp | Ala | Ser | Gly | Asp | Leu | Tyr |
| | 50 | | | | | 55 | | | | 60 | | | | | |
| Thr | Thr | Ser | Ser | Gln | Leu | Thr | Leu | Pro | Ala | Thr | Gln | Cys | Pro | Asp | Gly |
| 65 | | | | | 70 | | | | 75 | | | | | 80 | |
| Lys | Ser | Val | Thr | Cys | His | Val | Lys | His | Tyr | Thr | Asn | Ser | Ser | Gln | Asp |
| | | | | 85 | | | | 90 | | | | | 95 | | |
| Val | Thr | Val | Pro | Cys | Arg | Val | Pro | Pro | Pro | Pro | Cys | Cys | His | Pro | |
| | | | 100 | | | | 105 | | | | 110 | | | | |
| Arg | Leu | Ser | Leu | His | Arg | Pro | Ala | Leu | Glu | Asp | Leu | Leu | Leu | Gly | Ser |
| | | | 115 | | | | 120 | | | | 125 | | | | |
| Glu | Ala | Asn | Leu | Thr | Cys | Thr | Leu | Thr | Gly | Leu | Arg | Asp | Ala | Ser | Gly |
| | 130 | | | | | 135 | | | | 140 | | | | | |
| Ala | Thr | Phe | Thr | Trp | Thr | Pro | Ser | Ser | Gly | Lys | Ser | Ala | Val | Gln | Gly |
| 145 | | | | | 150 | | | | 155 | | | | | 160 | |
| Pro | Pro | Glu | Arg | Asp | Leu | Cys | Gly | Cys | Tyr | Ser | Val | Ser | Ser | Val | Leu |
| | | | 165 | | | | 170 | | | | 175 | | | | |
| Pro | Gly | Cys | Ala | Gln | Pro | Trp | Asn | His | Gly | Glu | Thr | Phe | Thr | Cys | Thr |
| | | | 180 | | | | 185 | | | | 190 | | | | |
| Ala | Ala | His | Pro | Glu | Leu | Lys | Thr | Pro | Leu | Thr | Ala | Asn | Ile | Thr | Lys |
| | | 195 | | | | 200 | | | | 205 | | | | | |
| Ser | Gly | Asn | Thr | Phe | Arg | Pro | Glu | Val | His | Leu | Leu | Pro | Pro | Pro | Ser |
| | 210 | | | | | 215 | | | | 220 | | | | | |
| Glu | Glu | Leu | Ala | Leu | Asn | Glu | Leu | Val | Thr | Leu | Thr | Cys | Leu | Ala | Arg |
| 225 | | | | 230 | | | | | 235 | | | | | 240 | |
| Gly | Phe | Ser | Pro | Lys | Asp | Val | Leu | Val | Arg | Trp | Leu | Gln | Gly | Ser | Gln |
| | | | 245 | | | | 250 | | | | 255 | | | | |
| Glu | Leu | Pro | Arg | Glu | Lys | Tyr | Leu | Thr | Trp | Ala | Ser | Arg | Gln | Glu | Pro |
| | | 260 | | | | 265 | | | | 270 | | | | | |
| Ser | Gln | Gly | Thr | Thr | Thr | Phe | Ala | Val | Thr | Ser | Ile | Leu | Arg | Val | Ala |
| | | 275 | | | | 280 | | | | 285 | | | | | |
| Ala | Glu | Asp | Trp | Lys | Lys | Gly | Asp | Thr | Phe | Ser | Cys | Met | Val | Gly | His |
| | 290 | | | | 295 | | | | 300 | | | | | | |
| Glu | Ala | Leu | Pro | Leu | Ala | Phe | Thr | Gln | Lys | Thr | Ile | Asp | Arg | Leu | Ala |
| 305 | | | | 310 | | | | 315 | | | | | | 320 | |
| Gly | Lys | Pro | Thr | His | Val | Asn | Val | Ser | Val | Val | Met | Ala | Glu | Val | Asp |
| | | | | 325 | | | | 330 | | | | | 335 | | |
| Gly | Thr | Cys | Tyr | | | | | | | | | | | | |
| | | | 340 | | | | | | | | | | | | |

<210> SEQ ID NO 28
<211> LENGTH: 353
<212> TYPE: PRT
<213> ORGANISM: Homo sapiens
<220> FEATURE:
<221> NAME/KEY: MISC_FEATURE
<222> LOCATION: (1)..(353)
<223> OTHER INFORMATION: B3 protein

<400> SEQUENCE: 28

```
Val Pro Leu Pro Val Ile Ala Glu Leu Pro Lys Val Ser Val Phe
1               5                   10                  15

Val Pro Pro Arg Asp Gly Phe Phe Gly Asn Pro Arg Lys Ser Lys Leu
            20                  25                  30

Ile Cys Gln Ala Thr Gly Phe Ser Pro Arg Gln Ile Gln Val Ser Trp
            35                  40                  45

Leu Arg Glu Gly Lys Gln Val Gly Ser Gly Val Thr Thr Asp Gln Val
50                  55                  60

Gln Ala Glu Ala Lys Glu Ser Gly Pro Thr Thr Tyr Lys Val Thr Ser
65                  70                  75                  80

Thr Leu Thr Ile Lys Glu Ser Asp Trp Leu Ser Gln Ser Met Phe Thr
                85                  90                  95

Cys Arg Val Asp His Arg Gly Leu Thr Phe Gln Gln Asn Ala Ser Ser
                100                 105                 110

Met Cys Val Pro Asp Gln Asp Thr Ala Ile Arg Val Phe Ala Ile Pro
                115                 120                 125

Pro Ser Phe Ala Ser Ile Phe Leu Thr Lys Ser Thr Lys Leu Thr Cys
130                 135                 140

Leu Val Thr Asp Leu Thr Thr Tyr Asp Ser Val Thr Ile Ser Trp Thr
145                 150                 155                 160

Arg Gln Asn Gly Glu Ala Val Lys Thr His Thr Asn Ile Ser Glu Ser
                165                 170                 175

His Pro Asn Ala Thr Phe Ser Ala Val Gly Glu Ala Ser Ile Cys Glu
                180                 185                 190

Asp Asp Trp Asn Ser Gly Glu Arg Phe Thr Cys Thr Val Thr His Thr
                195                 200                 205

Asp Leu Pro Ser Pro Leu Lys Gln Thr Ile Ser Arg Pro Lys Gly Val
                210                 215                 220

Ala Leu His Arg Pro Asp Val Tyr Leu Leu Pro Pro Ala Arg Glu Gln
225                 230                 235                 240

Leu Asn Leu Arg Glu Ser Ala Thr Ile Thr Cys Leu Val Thr Gly Phe
                245                 250                 255

Ser Pro Ala Asp Val Phe Val Gln Trp Met Gln Arg Gly Gln Pro Leu
                260                 265                 270

Ser Pro Glu Lys Tyr Val Thr Ser Ala Pro Met Pro Glu Pro Gln Ala
                275                 280                 285

Pro Gly Arg Tyr Phe Ala His Ser Ile Leu Thr Val Ser Glu Glu Glu
                290                 295                 300

Trp Asn Thr Gly Glu Thr Tyr Thr Cys Val Val Ala His Glu Ala Leu
305                 310                 315                 320

Pro Asn Arg Val Thr Glu Arg Thr Val Asp Lys Ser Thr Gly Lys Pro
                325                 330                 335

Thr Leu Tyr Asn Val Ser Leu Val Met Ser Asp Thr Ala Gly Thr Cys
                340                 345                 350

Tyr
```

<210> SEQ ID NO 29
<211> LENGTH: 344
<212> TYPE: PRT
<213> ORGANISM: JC virus
<220> FEATURE:
<221> NAME/KEY: MISC_FEATURE
<222> LOCATION: (1)..(344)
<223> OTHER INFORMATION: B4 VP coat protein

<400> SEQUENCE: 29

```
Met Gly Ala Ala Leu Ala Leu Leu Gly Asp Leu Val Ala Thr Val Ser
1               5                   10                  15

Glu Ala Ala Ala Thr Gly Phe Ser Val Ala Glu Ile Ala Ala Gly
            20                  25                  30

Glu Ala Ala Thr Ile Glu Val Glu Ile Ala Ser Leu Ala Thr Val
        35                  40                  45

Glu Gly Ile Thr Ser Thr Ser Glu Ala Ile Ala Ala Ile Gly Leu Thr
    50                  55                  60

Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
                85                  90                  95

Leu Gly Tyr Arg Phe Phe Ala Asp Trp Asp His Lys Val Ser Thr Val
            100                 105                 110

Gly Leu Phe Gln Gln Pro Ala Met Ala Leu Gln Leu Phe Asn Pro Glu
        115                 120                 125

Asp Tyr Tyr Asp Ile Leu Phe Pro Gly Val Asn Ala Phe Val Asn Asn
130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ala Leu
                165                 170                 175

Thr Ser Gln Glu Ile Gln Arg Arg Thr Gln Lys Leu Phe Val Glu Ser
            180                 185                 190

Leu Ala Arg Phe Leu Glu Glu Thr Thr Trp Ala Ile Val Asn Ser Pro
        195                 200                 205

Ala Asn Leu Tyr Asn Tyr Ile Ser Asp Tyr Tyr Ser Arg Leu Ser Pro
    210                 215                 220

Val Arg Pro Ser Met Val Arg Gln Val Ala Gln Arg Glu Gly Thr Tyr
225                 230                 235                 240

Ile Ser Phe Gly His Ser Tyr Thr Gln Ser Ile Asp Asp Ala Asp Ser
                245                 250                 255

Ile Gln Glu Val Thr Gln Arg Leu Asp Leu Lys Thr Pro Asn Val Gln
            260                 265                 270

Ser Gly Glu Phe Ile Glu Arg Ser Ile Ala Pro Gly Gly Ala Asn Gln
        275                 280                 285

Arg Ser Ala Pro Gln Trp Met Leu Pro Leu Leu Gly Leu Tyr Gly
    290                 295                 300

Thr Val Thr Pro Ala Leu Glu Ala Tyr Glu Asp Gly Pro Asn Lys Lys
305                 310                 315                 320

Lys Arg Arg Lys Glu Gly Pro Arg Ala Ser Ser Lys Thr Ser Tyr Lys
                325                 330                 335

Arg Arg Ser Arg Ser Ser Arg Ser
            340
```

<210> SEQ ID NO 30
<211> LENGTH: 173
<212> TYPE: PRT
<213> ORGANISM: Arabidopsis thaliana
<220> FEATURE:
<221> NAME/KEY: MISC_FEATURE
<222> LOCATION: (1)..(173)
<223> OTHER INFORMATION: B5 oleosin protein

<400> SEQUENCE: 30

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170
```

<210> SEQ ID NO 31
<211> LENGTH: 427
<212> TYPE: PRT
<213> ORGANISM: Artificial Sequence
<220> FEATURE:
<223> OTHER INFORMATION: Synthetic construct, Pg A1-5:B1-5 protein

<400> SEQUENCE: 31

```
Met Glu Gln Pro Ser Cys Arg Arg Ala Phe Asp Leu Tyr Phe Val Leu
1               5                   10                  15

Asp Lys Ser Gly Ser Val Ala Asn Asn Trp Ile Glu Ile Tyr Asn Phe
            20                  25                  30

Val Gln Gln Leu Ala Glu Arg Phe Val Ser Pro Glu Met Arg Leu Ser
        35                  40                  45

Phe Ile Val Phe Ser Ser Gln Ala Thr Ile Ile Leu Pro Leu Thr Gly
    50                  55                  60

Asp Arg Gly Lys Ile Ser Lys Gly Leu Glu Asp Leu Lys Arg Val Ser
65                  70                  75                  80

Pro Val Gly Glu Thr Tyr Ile His Glu Gly Leu Lys Leu Ala Asn Glu
                85                  90                  95

Gln Ile Gln Lys Ala Gly Gly Leu Lys Thr Ser Ser Ile Ile Ile Ala
            100                 105                 110

Leu Thr Asp Gly Lys Leu Asp Gly Leu Val Pro Ser Tyr Ala Glu Lys
        115                 120                 125

Glu Ala Lys Ile Ser Arg Ser Leu Gly Ala Ser Val Tyr Cys Val Gly
    130                 135                 140

Val Leu Asp Phe Glu Gln Ala Gln Leu Glu Arg Ile Ala Asp Ser Lys
145                 150                 155                 160

Glu Gln Val Phe Pro Val Lys Gly Gly Phe Gln Ala Leu Lys Gly Ile
                165                 170                 175

Ile Asn Ser Ile Leu Ala Gln Ser Cys Thr Glu Gly Gly Gly Ser Gly
            180                 185                 190
```

Asn Ser Asp Lys Thr His Thr Cys Pro Pro Cys Pro Ala Pro Glu Leu
            195                 200                 205

Leu Gly Gly Pro Ser Val Phe Leu Phe Pro Pro Lys Pro Lys Asp Thr
        210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr Asn Ser
            260                 265                 270

Thr Tyr Arg Val Val Ser Val Leu Thr Val Leu His Gln Asp Trp Leu
        275                 280                 285

Asn Gly Lys Glu Tyr Lys Cys Lys Val Ser Asn Lys Ala Leu Pro Ala
    290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Glu Glu Met Thr Lys Asn Gln
                325                 330                 335

Val Ser Leu Thr Cys Leu Val Lys Gly Phe Tyr Pro Ser Asp Ile Ala
            340                 345                 350

Val Glu Trp Glu Ser Asn Gly Gln Pro Glu Asn Asn Tyr Lys Thr Thr
        355                 360                 365

Pro Pro Val Leu Asp Ser Asp Gly Ser Phe Phe Leu Tyr Ser Lys Leu
    370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys Asp Leu Ile Glu Gly Arg
            420                 425

<210> SEQ ID NO 32
<211> LENGTH: 395
<212> TYPE: DNA
<213> ORGANISM: Homo sapiens
<220> FEATURE:
<221> NAME/KEY: misc_feature
<222> LOCATION: (1)..(395)
<223> OTHER INFORMATION: C1-2 construct

<400> SEQUENCE: 32
ccatgggaaa gtgcaagtgc gctcgtatca cctctcgtat catccgttct tctgaggacc    60
ctaacgagga catcgtcgag cgtaacatcc gtatcatcgt ccctctcaac aaccgtgaga   120
acatctctga ccctacctct cctctccgta cccgtttcgt ctaccacctc tctgacctct   180
gcaagaagtg cgaccctacc gaggtcgagc tcgacaacca gatcgtcacc gctacccagt   240
ctaacatctg cgacgaggac tctgctaccg agacctgcta cacctacgac cgtaacaagt   300
gctacaccgc tgtcgtccct ctcgtctacg tggtgagac caagatggtc gagaccgctc   360 tcaccccctga cgcttgctac cctgactaag agctc   395

<210> SEQ ID NO 33
<211> LENGTH: 401
<212> TYPE: DNA
<213> ORGANISM: homo sapiens
<220> FEATURE:
<221> NAME/KEY: misc_feature
<222> LOCATION: (1)..(401)
<223> OTHER INFORMATION: C1-3 construct

<400> SEQUENCE: 33

```
ccatgggaaa gtgcaagtgc gctcgtatca cctctcgtat catccgttct tctgaggacc      60
ctaacgagga catcgtcgag cgtaacatcc gtatcatcgt ccctctcaac aaccgtgaga     120
acatctctga ccctacctct cctctccgta cccgtttcgt ctaccacctc tctgacctct     180
gcaagaagtg cgaccctacc gaggtcgagc tcgacaacca gatcgtcacc gctacccagt     240
ctaacatctg cgacgaggac tctgctaccg agacctgcta cacctacgac cgtaacaagt     300
gctacaccgc tgtcgtccct ctcgtctacg gtggtgagac caagatggtc gagaccgctc     360
tcaccccctga cgcttgctac cctgacgcag atctccaata a                        401
```

<210> SEQ ID NO 34
<211> LENGTH: 1133
<212> TYPE: DNA
<213> ORGANISM: Artificial Sequence
<220> FEATURE:
<223> OTHER INFORMATION: Synthetic construct, C2-2 construct

<400> SEQUENCE: 34

```
ccatggcccc aacaaagaga aaggagaaa ggaaggaccc agtgcaagtt ccaaaacttc       60
tcataagagg aggagtagaa gttcttgaag ttaaaactgg agttgactca attacagagg    120
tagaatgctt cttaactcca gaaatgggtg acccagatga gcatcttagg ggttttagta    180
agtcaatatc tatatcagat acatttgaaa gtgactcccc aaatagggac atgcttcctt    240
gttacagtgt ggccaggatt ccactaccta atctaaatga ggatctaact tgtggaaata    300
tactcatgtg ggaggctgtg acattaaaga ctgaggttat aggagtgaca gtttgatga    360
atgtgcattc taatggtcaa gcaactcatg acaatggtgc aggtaagcca gtgcagggta    420
caagttttca tttcttttct gttggaggtg aggcttaga attacaggga gtgcttttta    480
attacagaac aaagtaccca gatggaacaa tttttccaaa gaatgccaca gtgcaatctc    540
aagtcatgaa cacagagcat aaggcgtacc tagataagaa caaagcatat cctgttgaat    600
gttgggttcc tgatccaact agaaatgaaa acacaagata ttttggtaca ctaacaggag    660
gagaaaatgt tcctccagtt cttcatataa caaacactgc cacaacagtg ttgcttgatg    720
aatttggtgt tggaccactt tgtaaaggtg acaacttata cttgtcagct gttgatgtct    780
gtggtatgtt tacaaacagg tctggttccc agcagtggag aggactctcc agatatttta    840
aggtgcagct aaggaagagg agggttaaga acccataccc aatttctttc cttcttactg    900
atttgattaa cagaaggact cctagagttg atggacagcc tatgtatggt atggatgctc    960
aagtagagga ggttagagtt tttgagggaa cagaggagct tccaggagac ccagacatga   1020
tgagatacgt tgacaaatat ggacagttgc agacaaagat gctggcggcc gcagatctcc   1080
aaaagcttat tagcgaggag gatcttcatc accatcacca tcactaagag ctc          1133
```

<210> SEQ ID NO 35
<211> LENGTH: 159
<212> TYPE: PRT
<213> ORGANISM: Homo sapiens
<220> FEATURE:
<221> NAME/KEY: MISC_FEATURE
<222> LOCATION: (1)..(159)
<223> OTHER INFORMATION: C-1-protein

<400> SEQUENCE: 35

```
Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
            115                 120                 125

Asn Lys Cys Tyr Thr Ala Val Val Pro Leu Val Tyr Gly Gly Glu Thr
            130                 135                 140

Lys Met Val Glu Thr Ala Leu Thr Pro Asp Ala Cys Tyr Pro Asp
145                 150                 155

<210> SEQ ID NO 36
<211> LENGTH: 354
<212> TYPE: PRT
<213> ORGANISM: JC virus
<220> FEATURE:
<221> NAME/KEY: MISC_FEATURE
<222> LOCATION: (1)..(354)
<223> OTHER INFORMATION: C2 protein

<400> SEQUENCE: 36

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
            115                 120                 125

His Asp Asn Gly Ala Gly Lys Pro Val Gln Gly Thr Ser Phe His Phe
            130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
```

```
                195                 200                 205
Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
            340                 345                 350

Met Leu

<210> SEQ ID NO 37
<211> LENGTH: 721
<212> TYPE: DNA
<213> ORGANISM: Artificial Sequence
<220> FEATURE:
<223> OTHER INFORMATION: Synthetic construct, PgA2-4:B1-3 construct

<400> SEQUENCE: 37
ccatgggtga cgtcggtatg cacgtcaagg agaaggagaa gaacaaggac gagaacaagc      60
gtaaggacga ggagcgtaac aagacccagg aggagcacct caaggagatc atgaagcaca     120
tcgtcaagat cgaggtcaag ggtgaggagg ctgtcaagaa ggaggctgct gagaagctcc     180
tcgagaaggt cccttctgac gtcctcgaga tgtacaaggc tatcggtggt aagatctaca     240
tcgtcgacgg tgacatcacc aagcacatct ctctcgaggc tctctctgag gacaagaaga     300
agatcaagga catctacggt aaggacgctc tcctccacga gcactacgtc tacgctaagg     360
agggttacga gcctgtcctc gtcatccagt ctttctgagga ctacgtcgag aacaccgaga     420
aggctctcaa cgtctactac gagatcggta agatcctctc tcgtgacatc ctctctaaga     480
tcaaccagcc ttaccagaag ttcctcgacg tcctcaacac catcaagaac gcttctgact     540
ctgacggtca ggacctcctc ttcaccaacc agctcaagga gcaccctacc gacttctctg     600
tcgagttcct cgagcagaac tctaacgagg tccaggaggt cttcgctaag gctttcgctt     660
actacatcga gcctcagcac cgtgacgtcc tccagctcta cgctcctgag gctgcggccg     720
c                                                                    721

<210> SEQ ID NO 38
<211> LENGTH: 1297
<212> TYPE: DNA
<213> ORGANISM: Artificial Sequence
<220> FEATURE:
<223> OTHER INFORMATION: Synthetic construct, Pg1-1:B1-1-1 construct

<400> SEQUENCE: 38
agtcccatgg aacaaccatc ttgccgtagg gctttcgatc tctacttcgt gctcgataag      60
```

```
tccggctctg ttgctaacaa ctggatcgaa atctacaact tcgtgcagca gctcgctgag    120
agattcgttt ctccagagat gaggctctcc ttcatcgtgt tctcttcaca ggctactatc    180 atcctccac tcactggtga taggggcaag atttctaagg gactcgagga tctcaagagg     240
gtgtcaccag ttggagagac ttacattcac gagggactca agcttgctaa cgagcagatt    300
caaaaggctg gcggcctcaa gacttcctcc attattatcg ctctcactga tggcaagctc    360
gatggacttg ttccatccta cgctgagaaa gaggctaaga tcagtcgttc ccttggcgct    420
tctgtttact gcgttggagt gcttgatttc gagcaggctc agcttgagag gatcgctgat    480
tccaaagagc aggttttccc agttaagggc ggattccaag ctctcaaggg catcatcaac    540
tccatccttg ctcagtcttg tactgagggt ggtggatccg gaaactccga taagactcat    600
acttgtccac catgcccagc tccagaactt cttggaggac catctgtgtt cttgttccca    660
ccaaagccaa aggatactct catgatctcc aggactccag aggttacatg cgttgtggtt    720
gatgtgtctc acgaggatcc agaggtgaag ttcaactggt atgtggatgg tgttgaggtg    780
cacaacgcta agactaagcc acgtgaggaa cagtacaact ccacttacag ggtggtgtct    840
gtgcttactg tgcttcacca ggattggctc aacggcaaag agtacaagtg caaggtgtcc    900
aacaaggctc tcccagctcc aatcgaaaag actatctcca aggctaaggg acagccaagg    960
gaaccacagg tttacactct tccaccatcc agggaagaga tgactaagaa ccaggtgtcc   1020
cttacttgcc tcgtgaaggg attctaccca tccgatattg ctgttgagtg ggagtctaat   1080
ggccagccag agaacaacta caagactact ccaccagtgc tcgattccga tggctcattc   1140
ttcttgtact ccaagctcac tgtggataag tccaggtggc agcagggaaa cgttttctct   1200
tgctctgtta tgcacgaggc tctccacaac cactacactc agaagtcctt gtccttgtcc   1260
ccaggcaagg atcttattga gggaagaaga tctccaa                            1297
```

<210> SEQ ID NO 39
<211> LENGTH: 10
<212> TYPE: DNA
<213> ORGANISM: Artificial Sequence
<220> FEATURE:
<223> OTHER INFORMATION: Synthetic construct, Kozak-like sequence

<400> SEQUENCE: 39
gacaccatgg                                                              10

<210> SEQ ID NO 40
<211> LENGTH: 19
<212> TYPE: DNA
<213> ORGANISM: Artificial Sequence
<220> FEATURE:
<223> OTHER INFORMATION: Synthetic construct, BglII and Sac sites

<400> SEQUENCE: 40
agatctccaa taagagctc                                                    19

<210> SEQ ID NO 41
<211> LENGTH: 16
<212> TYPE: DNA
<213> ORGANISM: Artificial Sequence
<220> FEATURE:
<223> OTHER INFORMATION: Synthetic construct, NotI site

<400> SEQUENCE: 41
tcttgcggcc gcagga                                                       16

```
<210> SEQ ID NO 42
<211> LENGTH: 24
<212> TYPE: PRT
<213> ORGANISM: Artificial Sequence
<220> FEATURE:
<223> OTHER INFORMATION: Synthetic construct, BAA targeting peptide

<400> SEQUENCE: 42

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 43
<211> LENGTH: 33
<212> TYPE: PRT
<213> ORGANISM: Artificial Sequence
<220> FEATURE:
<223> OTHER INFORMATION: Synthetic construct, APBP1 targeting peptide

<400> SEQUENCE: 43

Met Ile Val Leu Ser Val Gly Ser Ala Ser Ser Pro Ile Val Val
1               5                   10                  15

Val Phe Ser Val Ala Leu Leu Leu Phe Tyr Phe Ser Glu Thr Ser Leu
            20                  25                  30

Gly

<210> SEQ ID NO 44
<211> LENGTH: 7
<212> TYPE: PRT
<213> ORGANISM: Artificial Sequence
<220> FEATURE:
<223> OTHER INFORMATION: Synthetic construct, flexible linker

<400> SEQUENCE: 44

Gly Gly Gly Ser Gly Asn Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Syntehtic construct, Thrombin cleavage factor

<400> SEQUENCE: 45

Leu Val Pro Arg Gly Ser
1               5

<210> SEQ ID NO 46
<211> LENGTH: 4
<212> TYPE: PRT
<213> ORGANISM: Artificial Sequence
<220> FEATURE:
<223> OTHER INFORMATION: Synthetic construct, factor Xa protease
      cleavage peptide

<400> SEQUENCE: 46

Ile Glu Gly Arg
1

<210> SEQ ID NO 47
<211> LENGTH: 558
<212> TYPE: DNA
<213> ORGANISM: Artificial Sequence
<220> FEATURE:
```

<223> OTHER INFORMATION: Synthetic construct, PgA1-3 construct

<400> SEQUENCE: 47

| | | | | |
|---|---|---|---|---|
| atggaacaac | cttcttgtcg | tcgagctttt | gatctttatt | ttgttcttga taaatctggt | 60 |
| tctgttgcta | ataattggat | tgaaatttat | aattttgttc | aacaacttgc tgaaagattt | 120 |
| gtttctcctg | aaatgagact | ttcttttatt | gttttttctt | ctcaagctac tattattctt | 180 |
| cctcttactg | gtgatagagg | aaaaatttct | aaaggacttg | aggatttgaa aagagtttct | 240 |
| cctgttggtg | aaacttatat | tcatgaggga | cttaaacttg | ctaatgaaca aattcaaaaa | 300 |
| gctggtggtc | ttaaaacttc | ttctattatt | attgctctta | ctgatggaaa acttgatggt | 360 |
| cttgttcctt | cttatgctga | aaaagaagct | aaaatttcaa | gatcacttgg tgcttctgtt | 420 |
| tattgtgttg | gtgttcttga | ttttgaacaa | gctcaacttg | aaagaattgc tgattctaaa | 480 |
| gaacaagttt | ttcctgttaa | gggtggattt | caagctctta | aggaattat taattctatt | 540 |
| cttgctcaat | cttgtact | | | | 558 |

<210> SEQ ID NO 48
<211> LENGTH: 690
<212> TYPE: DNA
<213> ORGANISM: Artificial Sequence
<220> FEATURE:
<223> OTHER INFORMATION: Synthetic construct, PgB1-3 construct

<400> SEQUENCE: 48

| | | | | |
|---|---|---|---|---|
| gacaagaccc | acacctgccc | tccttgccct | gctcctgagc | tcctcggtgg tccttctgtc | 60 |
| ttcctcttcc | ctcctaagcc | taaggacacc | ctcatgatct | ctcgtacccc tgaggtcacc | 120 |
| tgcgtcgtcg | tcgacgtctc | tcacgaggac | cctgaggtca | agttcaactg gtacgtcgac | 180 |
| ggtgtcgagg | tccacaacgc | taagaccaag | cctcgtgagg | agcagtacaa ctctacctac | 240 |
| cgtgtcgtct | ctgtcctcac | cgtcctccac | caggactggc | tcaacggtaa ggagtacaag | 300 |
| tgcaaggtct | ctaacaaggc | tctccctgct | cctatcgaga | agaccatctc taaggctaag | 360 |
| ggtcagcctc | gtgagcctca | ggtctacacc | ctccctcctt | ctcgtgagga tgaccaag | 420 |
| aaccaggtct | ctctcacctg | cctcgtcaag | ggtttctacc | cttctgacat cgctgtcgag | 480 |
| tgggagtcta | acggtcagcc | tgagaacaac | tacaagacca | cccctcctgt cctcgactct | 540 |
| gacggttctt | tcttcctcta | ctctaagctc | accgtcgaca | gtctcgttg gcagcagggt | 600 |
| aacgtcttct | cttgctctgt | catgcacgag | gctctccaca | ccactacac ccagaagtct | 660 |
| ctctctctct | ctcctggtaa | ggacctctaa | | | 690 |

<210> SEQ ID NO 49
<211> LENGTH: 588
<212> TYPE: DNA
<213> ORGANISM: Artificial Sequence
<220> FEATURE:
<223> OTHER INFORMATION: Synthetic construct, PgA1-4 construct

<400> SEQUENCE: 49

| | | | | |
|---|---|---|---|---|
| atggaacaac | cttcttgtcg | tcgagctttt | gatctttatt | ttgttcttga taaatctggt | 60 |
| tctgttgcta | ataattggat | tgaaatttat | aattttgttc | aacaacttgc tgaaagattt | 120 |
| gtttctcctg | aaatgagact | ttcttttatt | gttttttctt | ctcaagctac tattattctt | 180 |
| cctcttactg | gtgatagagg | aaaaatttct | aaaggacttg | aggatttgaa aagagtttct | 240 |
| cctgttggtg | aaacttatat | tcatgaggga | cttaaacttg | ctaatgaaca aattcaaaaa | 300 |
| gctggtggtc | ttaaaacttc | ttctattatt | attgctctta | ctgatggaaa acttgatggt | 360 |

```
cttgttcctt cttatgctga aaaagaagct aaaatttcaa gatcacttgg tgcttctgtt    420
tattgtgttg gtgttcttga ttttgaacaa gctcaacttg aaagaattgc tgattctaaa    480
gaacaagttt ttcctgttaa gggtggattt caagctctta aaggaattat taattctatt    540
cttgctcaat cttgtactgc ggccgcagga ggtggatctg gaaattct                 588

<210> SEQ ID NO 50
<211> LENGTH: 680
<212> TYPE: DNA
<213> ORGANISM: Artificial Sequence
<220> FEATURE:
<223> OTHER INFORMATION: Synthetic construct, PgB1-4 construct

<400> SEQUENCE: 50
gacaagaccc acacctgccc tccttgccct gctcctgagc tcctcggtgg tccttctgtc     60
ttcctcttcc ctcctaagcc taaggacacc ctcatgatct ctcgtacccc tgaggtcacc    120
tgcgtcgtcg tcgacgtctc tcacgaggac cctgaggtca agttcaactg gtacgtcgac    180
ggtgtcgagg tccacaacgc taagaccaag cctcgtgagg agcagtacaa ctctacctac    240
cgtgtcgtct ctgtcctcac cgtcctccac caggactggc tcaacggtaa ggagtacaag    300
tgcaaggtct ctaacaaggc tctccctgct cctatcgaga agaccatctc taaggctaag    360
ggtcagcctc gtgagcctca ggtctacacc ctccctcctt ctcgtgagga tgaccaag     420 aaccaggtct ctctcacctg cctcgtcaag ggtttctacc cttctgacat cgctgtcgag    480
tgggagtcta acggtcagcc tgagaacaac tacaagacca cccctcctgt cctcgactct    540
gacggttctt tcttcctcta ctctaagctc accgtcgaca gtctcgttg gcagcagggt    600 aacgtcttct cttgctctgt catgcacgag gctctccaca ccactacac ccagaagtct    660 ctctctctct ctcctggtaa                                                680

<210> SEQ ID NO 51
<211> LENGTH: 790
<212> TYPE: DNA
<213> ORGANISM: Artificial Sequence
<220> FEATURE:
<223> OTHER INFORMATION: Synthetic construct, PgB2-3 construct

<400> SEQUENCE: 51
ggaaattctg acgtcaccgt cccttgccct gtcccttcta cccctcctac cccttctcct     60
tctaccccct ctaccccttc tccttcttgc tgccacccctc gtctctctct ccaccgtcct   120
gctctcgagg acctcctcct cggttctgag gctaacctca cctgcaccct caccggtctc    180
cgtgacgctt ctggtgtcac cttcacctgg accccttctt ctggtaagtc tgctgtccag    240
ggtcctcctg agcgtgacct ctgcggttgc tactctgtct cttctgtcct ccctggttgc    300
gctgagcctt ggaaccacgg taagaccttc acctgcaccg ctgcttaccc tgagtctaag    360
acccctctca ccgctaccct ctctaagtct ggtaacacct tccgtcctga ggtccacctc    420
ctccctcctc cttctgagga gctcgctctc aacgagctcg tcaccctcac ctgcctcgct    480
cgtggtttct ctcctaagga cgtcctcgtc cgttggctcc agggttctca ggagctccct    540
cgtgagaagt acctcacctg ggcttctcgt caggagcctt ctcagggtac caccaccttc    600
gctgtcacct ctatcctccg tgtcgctgct gaggactgga gaagggtga caccttctct    660 tgcatggtcg gtcacgaggc tctccctctc gctttcaccc agaagaccat cgaccgtctc    720
gctggtaagc ctacccacgt caacgtctct gtcgtcatgg ctgaggtcga cggtacctgc    780
```
tacccaataa                                                              790

<210> SEQ ID NO 52
<211> LENGTH: 777
<212> TYPE: DNA
<213> ORGANISM: Artificial Sequence
<220> FEATURE:
<223> OTHER INFORMATION: Synthetic construct, PgB2-4 construct

<400> SEQUENCE: 52
gacgtcaccg tcccttgccc tgtcccttct acccctccta ccccttctcc ttctacccct      60
cctacccctt ctccttcttg ctgccaccct cgtctctctc tccaccgtcc tgctctcgag     120
gacctcctcc tcggttctga ggctaacctc acctgcaccc tcaccggtct ccgtgacgct     180
tctggtgtca ccttcacctg gacccctct tctggtaagt ctgctgtcca gggtcctcct     240
gagcgtgacc tctgcggttg ctactctgtc tcttctgtcc tccctggttg cgctgagcct     300
tggaaccacg gtaagacctt cacctgcacc gctgcttacc ctgagtctaa gaccctctc     360
accgctaccc tctctaagtc tggtaacacc ttccgtcctg aggtccacct cctccctcct     420
ccttctgagg agctcgctct caacgagctc gtcaccctca cctgcctcgc tcgtggtttc     480
tctcctaagg acgtcctcgt ccgttggctc cagggttctc aggagctccc tcgtgagaag     540
tacctcacct gggcttctcg tcaggagcct tctcagggta ccaccacctt cgctgtcacc     600
tctatcctcc gtgtcgctgc tgaggactgg aagaagggtg acaccttctc ttgcatggtc     660
ggtcacgagg ctctccctct cgctttcacc cagaagacca tcgaccgtct cgctggtaag     720
cctacccacg tcaacgtctc tgtcgtcatg gctgaggtcg acggtacctg ctactaa       777

<210> SEQ ID NO 53
<211> LENGTH: 1066
<212> TYPE: DNA
<213> ORGANISM: Artificial Sequence
<220> FEATURE:
<223> OTHER INFORMATION: Synthetic construct, PgB3-3 construct

<400> SEQUENCE: 53
gtccctctcc ctgtcatcgc tgagctccct cctaaggtct ctgtcttcgt ccctcctcgt      60
gacggtttct tcggtaaccc tcgtaagtct aagctcatct gccaggctac cggtttctct     120
cctcgtcaga tccaggtctc ttggctccgt gagggtaagc aggtcggttc tggtgtcacc     180
accgaccagg tccaggctga ggctaaggag tctggtccta ccacctacaa ggtcacctct     240
accctcacca tcaaggagtc tgactggctc tctcagtcta tgttcacctg ccgtgtcgac     300
caccgtggtc tcaccttcca gcagaacgct tcttctatgt gcgtccctga ccaggacacc     360
gctatccgtg tcttcgctat ccctccttct ttcgcttcta tcttcctcac caagtctacc     420
aagctcacct gcctcgtcac cgacctcacc acctacgact ctgtcaccat ctcttggacc     480
cgtcagaacg gtgaggctgt caagacccac accaacatct ctgagtctca ccctaacgct     540
accttctctg ctgtcggtga ggcttctatc tgcgaggacg actggaactc tggtgagcgt     600
ttcacctgca ccgtcaccca caccgacctc ccttctcctc tcaagcagac catctctcgt     660
cctaagggtg tcgctctcca ccgtcctgac gtctacctcc tccctcctgc tgtgagcag     720
ctcaacctcc gtgagtctgc taccatcacc tgcctcgtca ccggtttctc tcctgctgac     780
gtcttcgtcc agtggatgca gcgtggtcag cctctctctc ctgagaagta cgtcacctct     840
gctcctatgc ctgagcctca ggctcctggt cgttacttcg ctcactctat cctcaccgtc     900
tctgaggagg agtggaacac cggtgagacc tacacctgcg tcgtcgctca cgaggctctc     960

```
cctaaccgtg tcaccgagcg taccgtcgac aagtctaccg gtaagcctac cctctacaac    1020
gtctctctcg tcatgtctga caccgctggt acctgctacc caataa                  1066

<210> SEQ ID NO 54
<211> LENGTH: 1062
<212> TYPE: DNA
<213> ORGANISM: Artificial Sequence
<220> FEATURE:
<223> OTHER INFORMATION: Synthetic cosntruct, PgB3-4 construct

<400> SEQUENCE: 54
gtccctctcc ctgtcatcgc tgagctccct cctaaggtct ctgtcttcgt ccctcctcgt      60
gacggtttct tcggtaaccc tcgtaagtct aagctcatct gccaggctac cggtttctct     120
cctcgtcaga tccaggtctc ttggctccgt gagggtaagc aggtcggttc tggtgtcacc     180
accgaccagg tccaggctga ggctaaggag tctggtccta ccacctacaa ggtcacctct     240
accctcacca tcaaggagtc tgactggctc tctcagtcta tgttcacctg ccgtgtcgac     300
caccgtggtc tcaccttcca gcagaacgct tcttctatgt gcgtccctga ccaggacacc     360
gctatccgtg tcttcgctat ccctccttct ttcgcttcta tcttcctcac caagtctacc     420
aagctcacct gcctcgtcac cgacctcacc acctacgact ctgtcaccat ctcttggacc     480
cgtcagaacg gtgaggctgt caagacccac accaacatct ctgagtctca ccctaacgct     540
accttctctg ctgtcggtga ggcttctatc tgcgaggacg actggaactc tggtgagcgt     600
ttcacctgca ccgtcaccca caccgacctc ccttctcctc tcaagcagac catctctcgt     660
cctaagggtg tcgctctcca ccgtcctgac gtctacctcc tccctcctgc tcgtgagcag     720
ctcaacctcc gtgagtctgc taccatcacc tgcctcgtca ccggtttctc tcctgctgac     780
gtcttcgtcc agtggatgca gcgtggtcag cctctctctc tgagaagta cgtcacctct     840 gctcctatgc ctgagcctca ggctcctggt cgttacttcg ctcactctat cctcaccgtc     900
tctgaggagg agtggaacac cggtgagacc tacacctgcg tcgtcgctca cgaggctctc     960
cctaaccgtg tcaccgagcg taccgtcgac aagtctaccg gtaagcctac cctctacaac    1020
gtctctctcg tcatgtctga caccgctggt acctgctact aa                      1062

<210> SEQ ID NO 55
<211> LENGTH: 1032
<212> TYPE: DNA
<213> ORGANISM: Artificial Sequence
<220> FEATURE:
<223> OTHER INFORMATION: Synthetic construct, PgB4-2 construct

<400> SEQUENCE: 55
atgggtgctg ctctcgctct cctcggtgac ctcgtcgcta ccgtctctga ggctgctgct      60
gctaccggtt tctctgtcgc tgagatcgct gctggtgagg ctgctgctac catcgaggtc     120
gagatcgctt ctctcgctac cgtcgagggt atcacctcta cctctgaggc tatcgctgct     180
atcggtctca cccctgagac ctacgctgtc atcaccggtg ctcctggtgc tgtcgctggt     240
ttcgctgctc tcgtccagac cgtcaccggt ggttctgcta tcgctcagct cggttaccgt     300
ttcttcgctg actgggacca aggtctctct accgtcggtc tcttccagca gcctgctatg     360
gctctccagc tcttcaaccc tgaggactac tacgacatcc tcttccctgg tgtcaacgct     420
ttcgtcaaca acatccacta cctcgaccct cgtcactggg gtccttctct cttctctacc     480
atctctcagg ctttctggaa cctcgtccgt gacgacctcc ctgctctcac ctctcaggag     540
```

```
atccagcgtc gtacccagaa gctcttcgtc gagtctctcg ctcgtttcct cgaggagacc    600
acctgggcta tcgtcaactc tcctgctaac ctctacaact acatctctga ctactactct    660
cgtctctctc ctgtccgtcc ttctatggtc cgtcaggtcg ctcagcgtga gggtacctac    720
atctctttcg gtcactctta cacccagtct atcgacgacg ctgactctat ccaggaggtc    780
acccagcgtc tcgacctcaa gacccctaac gtccagtctg gtgagttcat cgagcgttct    840
atcgctcctg gtggtgctaa ccagcgttct gctcctcagt ggatgctccc tctcctcctc    900
ggtctctacg gtaccgtcac ccctgctctc gaggcttacg aggacggtcc taacaagaag    960
aagcgtcgta aggagggtcc tcgtgcttct tctaagacct cttacaagcg tcgttctcgt   1020
tcttctcgtt ct                                                      1032

<210> SEQ ID NO 56
<211> LENGTH: 519
<212> TYPE: DNA
<213> ORGANISM: Artificial Sequence
<220> FEATURE:
<223> OTHER INFORMATION: Synthetic construct, PgB5-2 construct

<400> SEQUENCE: 56
atggccgaca cggccagggg cacgcaccac gacatcatcg gcagggacca gtacccgatg     60
atgggcaggg acaggggacca gtaccagatg tccggcaggg gctccgacta ctccaagtcc   120
aggcagatcg ccaaggccgc cacggccgtg acggccggcg gctccctcct cgtgctctcc   180
tccctcacgc tcgtgggcac ggtgatcgcc ctcacggtgg ccacgccgct cctcgtgatc   240
ttctccccga tcctcgtgcc ggccctcatc acggtggccc tcctcatcac gggcttcctc   300
tcctccggcg gcttcggcat cgccgccatc acggtgttct cctggatcta caagtacgcc   360
acgggcgagc acccgcaggg ctccgacaag ctcgactccg ccaggatgaa gctcggctcc   420
aaggcccagg acctcaagga cagggcccag tactacggcc agcagcacac gggcggcgag   480
cacgacaggg acaggacgag gggcggccag cacacgacg                          519

<210> SEQ ID NO 57
<211> LENGTH: 711
<212> TYPE: DNA
<213> ORGANISM: Artificial Sequence
<220> FEATURE:
<223> OTHER INFORMATION: Synthetic construct, PgA2-4 construct

<400> SEQUENCE: 57
atgggtgacg tcggtatgca cgtcaaggag aaggagaaga acaaggacga gaacaagcgt     60
aaggacgagg agcgtaacaa gacccaggag gagcacctca aggagatcat gaagcacatc    120
gtcaagatcg aggtcaaggg tgaggaggct gtcaagaagg aggctgctga gaagctcctc    180
gagaaggtcc cttctgacgt cctcgagatg tacaaggcta tcggtggtaa gatctacatc    240
gtcgacggtg acatcaccaa gcacatctct ctcgaggctc tctctgagga caagaagaag    300
atcaaggaca tctacggtaa ggacgctctc ctccacgagc actacgtcta cgctaaggag    360
ggttacgagc ctgtcctcgt catccagtct tctgaggact acgtcgagaa caccgagaag    420
gctctcaacg tctactacga gatcggtaag atcctctctc gtgacatcct ctctaagatc    480
aaccagcctt accagaagtt cctcgacgtc ctcaacacca tcaagaacgc ttctgactct    540
gacggtcagg acctcctctt caccaaccag ctcaaggagc ccctaccga cttctctgtc    600 gagttcctcg agcagaactc taacgaggtc caggaggtct cgctaaggc tttcgcttac    660 tacatcgagc ctcagcaccg tgacgtcctc cagctctacg ctcctgaggc t            711
```

<210> SEQ ID NO 58
<211> LENGTH: 560
<212> TYPE: DNA
<213> ORGANISM: Artificial Sequence
<220> FEATURE:
<223> OTHER INFORMATION: Synthetic construct, PgA1-5 construct

<400> SEQUENCE: 58

```
atggaacaac catcttgccg tagggctttc gatctctact tcgtgctcga taagtccggc      60
ctgttgctaa caactggatc gaaatctaca acttcgtgca gcagctcgct gagagattcg     120
tttctccaga gatgaggctc tccttcatcg tgttctcttc acaggctact atcatccctcc    180
cactcactgg tgatagggc aagatttcta agggactcga ggatctcaag agggtgtcac      240
cagttggaga gacttacatt cacgagggac tcaagcttgc taacgagcag attcaaaagg    300
ctggcggcct caagacttcc tccattatta tcgctctcac tgatggcaag ctcgatggac    360
ttgttccatc ctacgctgag aaagaggcta agatcagtcg ttcccttggc gcttctgttt    420
actgcgttgg agtgcttgat tcgagcagg ctcagcttga gaggatcgct gattccaaag     480
agcaggtttt cccagttaag ggcggattcc aagctctcaa gggcatcatc aactccatcc    540
ttgctcagtc ttgtactgag                                                 560
```

<210> SEQ ID NO 59
<211> LENGTH: 690
<212> TYPE: DNA
<213> ORGANISM: Artificial Sequence
<220> FEATURE:
<223> OTHER INFORMATION: Synthetic construct, PgB1-5 construct

<400> SEQUENCE: 59

```
gataagactc atacttgtcc accatgccca gctccagaac ttcttggagg accatctgtg      60
ttcttgttcc caccaaagcc aaaggatact ctcatgatct ccaggactcc agaggttaca    120
tgcgttgtgg ttgatgtgtc tcacgaggat ccagaggtga agttcaactg gtatgtggat    180
ggtgttgagg tgcacaacgc taagactaag ccacgtgagg aacagtacaa ctccacttac    240
agggtggtgt ctgtgcttac tgtgcttcac caggattggc tcaacggcaa agagtacaag    300
tgcaaggtgt ccaacaaggc tctcccagct ccaatcgaaa agactatctc caaggctaag    360
ggacagccaa gggaaccaca ggtttacact cttccaccat ccagggaaga gatgactaag    420
aaccaggtgt cccttacttg cctcgtgaag ggattctacc catccgatat tgctgttgag    480
tgggagtcta atggccagcc agagaacaac tacaagacta ctccaccagt gctcgattcc    540
gatggctcat tcttcttgta ctccaagctc actgtggata agtccaggtg gcagcaggga    600
aacgttttct cttgctctgt tatgcacgag gctctcccaca accactacac tcagaagtcc    660
ttgtccttgt ccccaggcaa ggatcttatt                                      690
```

<210> SEQ ID NO 60
<211> LENGTH: 187
<212> TYPE: PRT
<213> ORGANISM: Artificial Sequence
<220> FEATURE:
<223> OTHER INFORMATION: Synthetic construct, PgA1-5 protein

<400> SEQUENCE: 60

```
Met Glu Gln Pro Ser Cys Arg Arg Ala Phe Asp Leu Tyr Phe Val Leu
1               5                   10                  15

Asp Lys Ser Gly Ser Val Ala Asn Asn Trp Ile Glu Ile Tyr Asn Phe
```

```
                20              25              30
Val Gln Gln Leu Ala Glu Arg Phe Val Ser Pro Glu Met Arg Leu Ser
            35                  40                  45
Phe Ile Val Phe Ser Ser Gln Ala Thr Ile Ile Leu Pro Leu Thr Gly
        50                  55                  60
Asp Arg Gly Lys Ile Ser Lys Gly Leu Glu Asp Leu Lys Arg Val Ser
65                  70                  75                  80
Pro Val Gly Glu Thr Tyr Ile His Glu Gly Leu Lys Leu Ala Asn Glu
                85                  90                  95
Gln Ile Gln Lys Ala Gly Gly Leu Lys Thr Ser Ser Ile Ile Ile Ala
            100                 105                 110
Leu Thr Asp Gly Lys Leu Asp Gly Leu Val Pro Ser Tyr Ala Glu Lys
        115                 120                 125
Glu Ala Lys Ile Ser Arg Ser Leu Gly Ala Ser Val Tyr Cys Val Gly
    130                 135                 140
Val Leu Asp Phe Glu Gln Ala Gln Leu Glu Arg Ile Ala Asp Ser Lys
145                 150                 155                 160
Glu Gln Val Phe Pro Val Lys Gly Gly Phe Gln Ala Leu Lys Gly Ile
                165                 170                 175
Ile Asn Ser Ile Leu Ala Gln Ser Cys Thr Glu
            180                 185

<210> SEQ ID NO 61
<211> LENGTH: 229
<212> TYPE: PRT
<213> ORGANISM: Artificial Sequence
<220> FEATURE:
<223> OTHER INFORMATION: Synthetic construct, PgB1-5 protein

<400> SEQUENCE: 61

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
```

```
                195                 200                 205
His Glu Ala Leu His Asn His Tyr Thr Gln Lys Ser Leu Ser Leu Ser
        210                 215                 220

Pro Gly Lys Asp Leu
225

<210> SEQ ID NO 62
<211> LENGTH: 19
<212> TYPE: DNA
<213> ORGANISM: Artificial Sequence
<220> FEATURE:
<223> OTHER INFORMATION: Syntehtic construct, NPTII forward primer

<400> SEQUENCE: 62
tgaatgaact gcaggacga                                              19

<210> SEQ ID NO 63
<211> LENGTH: 19
<212> TYPE: DNA
<213> ORGANISM: Artificial Sequence
<220> FEATURE:
<223> OTHER INFORMATION: Synthetic construct, NPTII  reverse primer

<400> SEQUENCE: 63
agccaacgta tgtcctgat                                              19

<210> SEQ ID NO 64
<211> LENGTH: 4
<212> TYPE: PRT
<213> ORGANISM: Artificial Sequence
<220> FEATURE:
<223> OTHER INFORMATION: Synthetic construct, HDEL peptide

<400> SEQUENCE: 64

His Asp Glu Leu
1

<210> SEQ ID NO 65
<211> LENGTH: 4
<212> TYPE: PRT
<213> ORGANISM: Artificial Sequence
<220> FEATURE:
<223> OTHER INFORMATION: Synthetic construct, KDEL peptide

<400> SEQUENCE: 65

Lys Asp Glu Leu
1
```